United States Patent
Gunn

(10) Patent No.: US 9,320,788 B2
(45) Date of Patent: Apr. 26, 2016

(54) TISSUE TARGETED ANTIGENIC ACTIVATION OF THE IMMUNE RESPONSE TO TREAT CANCERS

(71) Applicant: Qu Biologics Inc., Vancouver (CA)

(72) Inventor: Harold David Gunn, Vancouver (CA)

(73) Assignee: Qu Biologics Inc., Vancouver (CA)

( * ) Notice: Subject to any disclaimer, the term of this patent is extended or adjusted under 35 U.S.C. 154(b) by 261 days.

(21) Appl. No.: 13/923,211

(22) Filed: Jun. 20, 2013

(65) Prior Publication Data

US 2014/0010844 A1    Jan. 9, 2014

Related U.S. Application Data

(63) Continuation of application No. 13/894,343, filed on May 14, 2013, which is a continuation of application No. 12/843,296, filed on Jul. 26, 2010, now Pat. No. 8,501,198, which is a continuation-in-part of application No. 12/234,569, filed on Sep. 19, 2008, now Pat. No. 8,034,359, which is a continuation-in-part of application No. 11/553,972, filed on Oct. 27, 2006, now abandoned, which is a continuation-in-part of application No. PCT/CA2005/000812, filed on May 30, 2005, said application No. 12/234,569 is a continuation-in-part of application No. PCT/CA2007/001915, filed on Oct. 25, 2007.

(60) Provisional application No. 60/577,206, filed on Jun. 7, 2004.

(51) Int. Cl.
| | |
|---|---|
| *A61K 39/108* | (2006.01) |
| *A61K 39/00* | (2006.01) |
| *A61K 45/06* | (2006.01) |
| *G01N 33/50* | (2006.01) |

(52) U.S. Cl.
CPC ......... *A61K 39/0258* (2013.01); *A61K 39/0011* (2013.01); *A61K 45/06* (2013.01); *G01N 33/5011* (2013.01); *G01N 33/5047* (2013.01); *G01N 33/5082* (2013.01); *A61K 2039/521* (2013.01); *A61K 2039/5252* (2013.01); *G01N 2333/24* (2013.01); *G01N 2333/31* (2013.01)

(58) Field of Classification Search
None
See application file for complete search history.

(56) References Cited

U.S. PATENT DOCUMENTS

| | | | |
|---|---|---|---|
| 3,928,565 | A | 12/1975 | Homma et al. |
| 4,329,452 | A | 5/1982 | Maruyama |
| 4,880,626 | A | 11/1989 | McMichael |
| 5,652,332 | A | 7/1997 | Little, II |
| 5,869,057 | A | 2/1999 | Rock |
| 6,348,586 | B1 | 2/2002 | Chang et al. |
| 6,447,777 | B1 | 9/2002 | Terman et al. |
| 6,902,743 | B1 | 6/2005 | Setterstrom et al. |
| 7,018,629 | B2 | 3/2006 | Jacob et al. |
| 2002/0044948 | A1 | 4/2002 | Khleif et al. |
| 2003/0059400 | A1 | 3/2003 | Szalay |
| 2003/0073628 | A1 | 4/2003 | Shailubhai et al. |
| 2004/0014661 | A1 | 1/2004 | Goetsch et al. |
| 2005/0070463 | A1 | 3/2005 | Libon et al. |
| 2006/0147477 | A1 | 7/2006 | Cabezon Siliva et al. |
| 2007/0134264 | A1 | 6/2007 | Marshall |
| 2009/0074816 | A1 | 3/2009 | Gunn |
| 2010/0099600 | A1 | 4/2010 | Ny et al. |
| 2011/0020401 | A1 | 1/2011 | Gunn |

FOREIGN PATENT DOCUMENTS

| | | |
|---|---|---|
| CA | 2571805 A1 | 4/2008 |
| EP | 1415655 A | 5/2004 |
| JP | 54129117 | 10/1979 |
| JP | 56108716 | 8/1981 |
| JP | S58-39624 A | 3/1983 |
| JP | 6012071 | 1/1985 |
| JP | 2006-524703 A | 11/2006 |
| JP | 2009-537547 A | 10/2009 |
| WO | WO9323079 | 11/1993 |
| WO | WO 95/26742 A | 10/1995 |
| WO | WO 01/56387 A1 | 8/2001 |
| WO | WO 02/023994 A1 | 3/2002 |
| WO | WO 03/009859 A1 | 2/2003 |
| WO | WO 03/049751 A | 6/2003 |
| WO | WO 03/049752 A2 | 6/2003 |

(Continued)

OTHER PUBLICATIONS

Jibu et al., Clin. Expl. Metastasis, 1991,9(6): 529-540.*
Sarmiento et al., Current Gastroenterology Reports, 2003, 5:117-124.*
Critchley et al., Discovery Medicine, Aug. 2004, 22(4): 194-197.*
Kovats et al., Vaccine treatment in some hospital infections, Acta Physiol Hung (1991), 77(3-4):225-230.
Boudeau et al. "Invasive Ability of an *Escherichia coli* Strain Isolated from the Ileal Mucosa of a Patient with Crohn's Disease" Infection and Immunity, 1999, vol. 67(9):4499-4509.
Caugant et al., "Genetic Diversity and Temporal Variation in the *E. coli* Population of a Human Host" Genetics, 1981, vol. 98:467-496.
Connor "Sequelae of Traveler's Diarrhea: Focus on Postinfectious Irritable Bowel Syndrome" CID, 2005, vol. 2005:41, supplement 8: S557-S586.

(Continued)

*Primary Examiner* — Hong Sang
(74) *Attorney, Agent, or Firm* — Bret E. Field; Shweta Chandra; Bozicevic, Field & Francis LLP

(57) ABSTRACT

The invention provides in part methods of treating cancers of a specific organ or tissue by administering a composition that is antigenically specific for one or more microbes that are pathogenic in the specific organ or tissue in which the cancer is situated. The formulations of the invention thereby facilitate activation of an immune response to a cancer in a particular tissue or organ. The compositions may for example include killed or attenuated microbial pathogens, such as whole killed bacterial cells, and may be administered at sites distant from the cancer, for example the skin. In some embodiments, microbial species of endogenous flora or exogenous microbial pathogens that are known to cause infection in the relevant organ or tissue may be used in the formulation of the antigenic compositions.

17 Claims, 21 Drawing Sheets

(56) References Cited

FOREIGN PATENT DOCUMENTS

| WO | WO 03/063593 A1 | 8/2003 |
|---|---|---|
| WO | WO2004064717 A2 | 8/2004 |
| WO | WO2004069256 A1 | 8/2004 |
| WO | WO 2005/049056 A2 | 6/2005 |
| WO | WO 2005/099750 A1 | 10/2005 |
| WO | WO 2005/120560 A1 | 12/2005 |
| WO | WO 2008/049231 A1 | 5/2008 |
| WO | WO2009013443 | 1/2009 |
| WO | WO 2009/021977 A1 | 2/2009 |
| WO | WO 2010/068413 A1 | 6/2010 |
| WO | WO2012012874 A1 | 2/2012 |

OTHER PUBLICATIONS

Martinez-Medina et al. "Molecular diversity of Escherichia coli in the Human Gut: New Ecological Evidence Supporting the Role of Adherent-Invasive E. coli (AIEC) in Crohn's Disease" Inflamm Bowel Dis., 2009,vol. 15 (6):872-882.
Savarino et al., "Safety and Immonogenicity of an Oral, Killed Enterotoxigenic Escheria coli —Cholera Toxing B Subunit B Vaccine in Egyptian Adults" The Journal of Infectious Diseases, 1998, vol. 177:796-799.
Abel U, Becker N, Angerer R, et al. Common infections in the history of cancer patients and controls. J Cancer Res Clin Oncol. 1991; 117(4):339-344.
Abramson JL, Vaccarino V. Relationship between physical activity and inflammation among apparently healthy middle-aged and older US adults. Arch Intern Med. 2002;162(11):1286-1292.
Ajani UA, Ford ES, Mokdad AH. Dietary fiber and c-reactive protein: Findings from National Health and Nutrition Examination Survey Data. 2004;134:1181-5.
Akre K, Ekstrom A, Signorello L et al. Aspirin and risk for gastric cancer: a population-based case-conrol study in Sweden. Br J Cancer 2001 ;84:965-968.
Al-Ahaideb 2008 (Septic arthritis in patients with rheumatoid arthritis; Journal of Orthopaedic Surgery and Research; 3:33-36).
Asadullah K, Sterry W, Volk HD. Interleukin-10 therapy—review of a new approach. Pharmacol Rev 2003;55:241.
Assersohn et al., "A Randomized Pilot Study of SRL172 (Mycobaterium vaccae) in Patients with Small Cell Lung Cancer (SCLC) Treated with Chemotherapy" Clinical Oncology (2002) 14: 23-27.
Bach, DJ, Judd JT, Clevidence BA et al. Dietary fatty acids affect plasma markers of inflammation in healthy men fed controlled diets: A randomized crossover study. Am J Clin Nutr 2004; 79:969-73.
Balch, C.M. et al., A randomized prospective trial of adjuvant C. parvum immunotherapy in 260 patients with clinically localized melanoma (stage I), Cancer 49(6): 1079-1084 (Mar. 15, 1982).
Balkwill F, Charles KA, Mantovani A. Cancer Cell (2005) 7,211-217.
Balkwill F, Mantovani A. Inflammation and cancer: back to Virchow? Lancet 2001;357:539.
Baron JA, Sandler RS. Nonsteroidal anti-inflammatory drugs and cancer prevention. Annu Rev Med 2000;51 :511-23.
Barreda DR, Hanington PC, Belosevic M. Regulation of myeloid development and function by colony stimulating factors. Dev Comp Immunol 2004;28:509.
Bast et al., "Immunostimulants", Holland-Free Cancer Medicine 5th Edition—NCBI Bookshelf; http://www.ncbi.nlm.nih.gov/bookshelf.br.fcgi?book-cmed&part-A13924; 20 pp (2000).
Beaman BL, Moring SE, Ioneda T. Effect of growth stage on mycolic acid structure in cell walls of Nocardia asteroides GUH-2. Journal of Bacteriology 1988; 170(3): 1137-1142.
Beatty et al., "CD40 Agonists Alter Tumor Stroma and Show Efficacy Against Pancreatic Carcinoma in Mice and Humans", Science (2011) vol. 331, pp. 1612-1616.
Behr MA, Wilson MA, Gill WP, et al. Comparative genomics of BCG vaccines by whole genome microarray. Science 1999; 284: 1520-1523.
Ben-Baruch A. Breast cancer progression: a vicious cycle of promalignancy activities is mediated by inflammatory cells, chemokines and cytokines. Kluwer Academic Publishers; 2005.
Ben-Baruch A. Host microenvironment in breast cancer development: inflammatory cells, cytokines and chemokines in breast cancer progression: reciprocal tumor-microenvironment interactions. Breast Cancer Res 2003;5:31.
Ben-Baruch A. Inflammation-associated immune suppression in cancer: The roles played by cytokines, chemokines and additional mediators. Seminars in Cancer Biology 16(2006)38-52.
Beuth J, Braun JM. Modulation of murine tumor growth and colonization by bromelaine, an extract of the pineapple plant (Ananas comosum) In Vivo Mar.-Apr. 2005;19(2):483-5.
Bierman HR, Crile M, Dod KS et al. Remissions in acute leukemia of childhood following actue infectious disease. Cancer 1953;6:591-605.
Bingham S. The fibre-folate debate in colo-rectal cancer. Proc. Nutr. Soc. Feb. 2006;65(1):19-23.
Bingle L, Brown NJ, Lewis CE. J. Pathol. (2002) 196,254-65.
Biswas et al., "Macrophage plasticity and interaction with lymphocyte subsets: cancer as a paradigm", Nature Immunology (2010) vol. 11, No. 10, pp. 889-896.
Bouchardy C, Schuler G, et al. Cancer risk by occupation and socio-economic group among men—a study by the Association of Swiss Registries. Scand J Work Environ Health 2002;28(Suppl 1):1-88.
Braat et al., "Prevention of experimental colitis by parenteral administration of a pathogen-derived immunomodulatory molecule" Colonic Inflammation Gut. (2007) vol. 56, No. 3; pp. 351-357.
Brigati C, Noonan DM et al. Tumors and inflammatory infiltrates: friends or foes? Clin Exp Metastasis 2002;19:247.
Brown-Elliot BA, Brown JM, Couville PS, Wallace RJ Jr. Clinical and laboratory features of the Nocardia spp. Based on current molecular taxonomy. Clinical Microbiology Reviews 2006; 19(2): 259-282.
Brunda et al., "Immunotherapy of the guinea pig line 10 hepatocarcinoma with a variety of nonviable bacteria", Cancer Research, 1980, 40(9):3211-3213.
Bruun J, Helge JW et al. Diet and exercise reduce low-grade inflammation and macrophage infiltration in adipose tissue but not in skeletal muscle in severely obese subjects. Article in Press. Am J Physiol Endocrinol Metab (Dec. 12, 2005) D01:10.1152/ajpendo.00506. 2005.
Buhtoiarov et al., "Anti-tumour synergy of cytotoxic chemotherapy and anti-CD40 plus CpG-ODN immunotherapy through repolarization of tumour-associated macrophages", Immunology (2011) vol. 132, No. 2, pp. 226-239.
Busse et al., "Influence of Cyclic AMP Level and Interferon Level in the Lymphocytes and Change in the Rate of Taking Root of the Tumor of a Transplantable Melanoma of the Syrian Hamster by Treatment with BCG Measles Vaccine as well as L Dopa and Amantadine", Radiobiologia Radiothfrapia. vol. 21, No. 3 (1980) pp. 292-301. (German Translation).
Butler JC, Schuchat A. Epidemiology of pneumococcal infections in the elderly. Drugs Aging 1999;15(Suppl 1):11-9.
Chakrabarty et al., "Microorganisms and Cancer: Quest for a Therapy" Journal of Bacteriology, (2003), vol. 185, pp. 2683-2686.
Chang et al., "Macrophage Arginase Promotes Tumor Cell Growth and Suppresses Nitric Oxide-mediated Tumor Cytotoxicity", Cancer Research (2001) vol. 61, pp. 1100-1106.
Cheng VS, Suit HD, Wang CC et al: Clinical trial of Corynebacterium parvum (intra-lymph-node and intravenous) and radiation therapy in the treatment of head and neck carcinoma. Cancer Jan. 15, 1982;49(2):239-44.
Cole WH. Efforts to explain spontaneous regression of cancer. J Surg Oncol. 1981; 17:201-209.
Cole WH. Spontaneous regression of cancer and the importance of finding its cause. NCI Monogr. 1976; 44:5-9.
Coley WB. Late results of the treatment of inoperable sarcoma by the mixed toxins of erysipelas and Bacillus prodigiosus. Am J Med Sci 1906; 131:375-430.
Coley WB. The treatment of inoperable sarcoma by bacterial toxins (the mixed toxins of the Streptococcus of erysipelas and th bacillus prodigiosus). Practitioner 1909;83:589-613.

(56) References Cited

OTHER PUBLICATIONS

Coley WB. The treatment of malignant tumors by repeated inoculations of erysipelas: with a report of ten original cases. Am J Med Sci 1893; 105:487-511.

Comeri GC, Belvisi P, Conti G, Cretarola E, Duvia R, Furgoni R, Gianneo E, Radice GP. Role of BCG in T1G3 bladder transitional cell carcinoma (TCC): our experience. Arch Urol Ital Androl Feb. 1996; 68(1):55-9.

Comes A, Di Carlo E, et al. IFN-gamma-independent synergistic effects of IL-2 and IL-15 induce anti-tumour immune responses in syngeneic mice. Eur J Immunol 2002;32:1914.

Condeelis J, Pollard JW. Macrophages: Obligate partners for tumor cell migration, invasion, and metastasis. Cell 124 Jan. 27, 2006 263-6.

Condeelis J, Segall JE. Intravital imaging of cell movement in tumours. Nat Rev Cancer 3(2003)921-930.

Cosenza et al., "Metastasis of hepatocellular carcinoma to the right colon manifested by gastrointestinal bleeding", Am. Surg., 1999, 65(3): 218-21.

Cotterchio M, Kreiger N, Sloan M, Steingart A. Nonsteroidal anti-inflammatory drug use and breast cancer risk. Cancer Epidemiol Biomarkers Prev 2001;10:1213-1217.

Coussens et al., "Inflammation and Cancer", Nature (2002) 420(6917):860-867.

Creasman WT, Omura GA, Brady MF et al: A randomized trial of cyclophosphamide, doxorubicin, and cisplatin with and without BCG in patients with suboptimal stage III and IV ovarian cancer: a Gynecologic Oncology Group study. Gynecol Oncol 1990; 39:239-243.

Crowther M Brown NJ, et al Microenvironmental influence on macrophage regulation of angiogenesis in wounds and malignant tumors. J Leukoc Biol 2001;70:478.

Curiel TJ, Coukos, G, Zou L, et al. Specific recruitment of regulatory T cells in ovarian carcinoma fosters immune privilege and predicts reduced survival. Nat Med 2004;10:942-949.

Daum SM, Seidman H, et al. Mortality experience of a cohort of cotton textile workers. Final progress report on Contract No. HSM 99-72-71 (NIOSH), Mar. 1, 1975.

Davidson SS. Carcinoma and malaria. Br. Med J 1902;1:77.

de Visser K, Coussens L. The Inflammatory Tumor Microenvironment and its Impact on Cancer Development. Dittmar T, Jaenker KS, Schmidt A (eds): Infection and Inflammation: Impacts on Oncogenesis. Contrib Microbiol Basel, Karger, 2006, vol. 13,118-137.

de Visser KE, Korets LV, Coussens LM. De novo carcinogenesis promoted by chronic inflammation is B lymphocyte dependent. Cancer Cell 2005;7:411-423.

Dechsupa S, Kothan S, Vergote J. Quercetin, Siamois 1 and Siamois 2 Induce Apoptosis in Human Breast Cancer MDA-MB-435 Cells Xenograft In Vivo. Cancer Biol Ther. Jan. 29, 2007;6(1).

Dempke W, Rie C et al. Cyclooxygenase-2: a novel target for cancer chemotherapy? J Cancer Res Clin Oncol 2001;127:411.

Derynck R, Akhurst RJ, Balmain A. TGFβsignaling in tumor suppression and cancer progression. Nat Genet 2001;29:117.

Di Carlo, Cappello P, et al. Immunological mechanisms elicited at the tumour site by lymphocyte activation gene-3 (LAG-3) versus IL-12: sharing a common Th1 anti-tumour immune pathway. J Pathol 2005;205:82.

Dimitrov N, Pilch Y, Glass A et al: Evaluation of the worth of corynebacterium parvum in conjunction with chemotherapy as adjuvant treatment for primary breast cancer. Eight-year results from the National Surgical Adjuvant Breast and Bowel Project B-10 Cancer Jul. 15, 1990;66(2)220-7.

Disaia PJ, Bundy BN, Curry SL et al: Phase III study on the treatment with cervical cancer stage IIB, IIIB, and IVA, with radiotherapy alone versus radiotherapy plus immunotherapy with intravenous Corynebacterium parvum: a Gynecologic Oncology Group Study. Gynecol Oncol Mar. 1987;26(3)386-97.

Dock G. The influence of complicating diseases upon leukemia. Am J Med Sci. 1904; 127:563-592.

Dumont N, Artega CL. Targeting the TGFβsignaling network in human neoplasia. Cancer Cell 2003;3:531.

Dumont N, Artega CL. Transforming growth factor-βand breast cancer: Tumor promoting effects of transforming growth factor-β. Breast Cancer Res 2000;2:125.

Eichenwald HF, McCracken Jr GH. Acute diarrheal disease. Med Clin N Am 1970;54:443-54.

Elegbede JA et al (1993) Effects of anticarcinogenic monoterpenes on phase II hepatic metabolizing enymes. Carcinogenesis 14:1221-3.

Elgert K. D., Alleva D. G. Mullins D. W. Tumor-induced immune dysfunction: the macrophage connection. J Leukoc Biol 1998; 64: 275-290.

Elliot et al., "Clearance of apoptotic cells: implications in health and disease", J. Cell Biol. (2010) vol. 189, No. 7, pp. 1059-1070.

Elosua R, Bartali B, et al. Association between physical activity, physical performance, and inflammatory biomarkers in an elderly population: The InCHIANTI Study. J Gerontology: Medical Sciences 2005;60A(6);760-67.

Enterline PE, Sykora JL, et al. Endotoxins, cotton dust and cancer. Lancet 1985;2:934-5.

Erb et al., "Clinical and Technical Considerations for Imaging Colorectal Cancers with Technetium-99m-Labeled AntiCEA Fab' Fragment", J Nucl Med Technol, 2000, 28(1): 12-18.

Everson TC, Cole WH. Spontaneous regression of cancer. A study and abstract of reports in the world medical literature and personal communications concerning spontaneous regression of malignant disease. W.B Saunders Co. Philadelphia. 1966.

Everson TC, Cole WH. Spontaneous regression of cancer: Preliminary report. Ann Surgery. 1966; 144:366-383.

Everson TC. Spontaneous regression of cancer. Ann New York Acad Sci. 1964; 114: 721-735.

Fenton et al., "Induction of T-cell immunity against Ras oncoproteins by soluble protein or Ras-expressing *Escherichia coli*", J Natl Cancer Inst, 1995, 87(24): 1853-1861.

First Examination Report dated Sep. 14, 2010 for Indian Patent Application No. 119/KOLNP/2007.

Fisher et al., "Evaluation of the worth of crynebacterium parvum in conjunction with chemotherapy as adjuvant treatment for primary breast cancer. Eight-year results from the National Surgical Adjuvant Breast and Bowel Project B-10" Cancer (Jul. 15, 1990) 66(2):220-7.

Friedman H et al (1987): Distinctive immunomodulatory effects of endotoxin and nontoxic lipopolysaccharide derivatives in lymphoid cell cultures J Biol Response Mod 6(6):664-77.

Gabizon A, Leibovich SJ, Goldman R. Contrasting effects of activated and nonactivated macrophages and macrophages from tumor-bearing mice on tumor growth in vivo. J Natl Cancer Inst 1980;65913-20.

Gao X, Bermudez OI, Tucker KL. Plasma c-reactive protein and homocystine concentrations are related to feqeunt fruit and vegetable intake in Hispanic and non-Hispanic white elders. J Nutr 2004;134:913-8.

Garcia-Hernandez ML, Hernandez-Pando R, et al. Interleukin 10 promotes B 16-melanoma growth by inhibition of macrophage functions and induction of tumour and vascular cell proliferation. Immunology 2002;105:231.

Garcia-Rodriquez LA, Huerta-Alvarez C. Reduced risk of colorectal cancer among long-term users of aspirin and nonaspirin nonsteroidal anti-inflammatory drugs. Epidemiology 2001;12:88-93.

Garland CF, Garland FC, Gorham ED, et al. The role of vitamin D in cancer prevention. Am J Public Heath Feb. 2006(96)252-61.

Gaynor ML (2003) One Oncologist's view of integrative care: Keynote address, Comprehensive Cancer Care Conference. Integrative Cancer Therapies 3(1):82-87.

Gersemann et al., "Innate immune dysfunction in inflammatory bowel disease", Journal of Internal Medicine (2012) vol. 271, No. 5, pp. 421-428.

Goede V, Brogelli L, et al. Induction of inflammatory angiogenesis by monocyte chemoattractant protein-1. Int J Cancer 1999;82:765.

Gottke MU, Wong P, Muhn C, et al. Hepatitis in disseminated bacillus Calmette-Guerin infection. Can J Gastroenterol 2000; 14:333-6.

Graham NM. The epidemiology of acute respiratory infections in children and adults: a global perspective. Epidemiol Rev 1990;12:149-78.

(56) References Cited

OTHER PUBLICATIONS

Grant WB. Epidemiology of disease risks in relation to vitamin D insufficiency. Prog Biophys Mol Biol 2006 92(1)65-79.
Grossarth-Maticek R, Frentzel-Beyme R, Kanazir D et al. Reported Herpes-virus infection, fever and cancer incidence in a prospective study. J Chronic Dis. 1987; 40:967-976.
Grosso, J, Herbert L, Owen J, Lopez D. MUC1/sec-espressing tumors are rejected in vivo by a T cell-dependent mechanism and secrete high levels of CCL@. J Immunol 2004;173:1721.
Gutierrez 2005 (Bone and Joint Infections in Children; Pediatr. Clin N Am. 52:779-794).
Hachem R, Raad I, Rolston K et al. Cutaneous and pulmonary infections caused by Mycobacterium vaccae. Clin Infect Dis. Jul. 1996;23(1):1 73-5.
Hadden JW. Immunodeficiency and cancer: prospects for correction. Int Immunopharmacol 2003;2:1061.
Haldane Dr. The co-existence of tubercle and cancer. Edinburgh Med J 1862;8:343-9.
Hanada T et al. Prognostic value of tumor-associated macrophage count in human bladder cancer. Int J Urol. 2000; 7:263-9.
Hanaue, H. et al., Hemolytic *Streptococcus* preparation OK-432; beneficial adjuvant therapy in recurrent gastric carcinoma, Tokai J Exp Clin Med 12(4): 209-214 (Nov. 1987).
Harper-Wynne, C. et al., Addition of SRL 172 to standard chemotherapy in small cell lung cancer (SCLC) improves symptom control, Lung Cancer 47(2):289-290 (Feb. 2005).
Harris SG, Padilla J et al. Prostaglandins as modulators of immunity. Trends Immunol 2002;23:144.
Havas, HF (1993) Clinical Results and immunologic effects of a mixed bacterial vaccine in cancer patients. Med Oncol. & Tumour Pharmachother. 10(4):145-58.
Hemminki K, Zhang H, Czene K. Socioeconomic factors in cancer in Sweden. Int J Cancer 2003;105:692-700.
Hewitt JA, Mokbel K et al. Exercise for breast cancer survival: the effect on cancer risk and cancer-related fatigue. Int J Fertil Womens Med Sep.-Oct. 2005;50(5 Pt 1):231-9.
Higgins, G. and Pack, G., Virus therapy in the treatment of tumors, Bull Hosp Joint Dis 12:379-382 (1951).
Hobohm U. Fever therapy revisited. British Journal of Cancer 2005; 92: 421-425.
Hoffman FL. The mortality from cancer in the Western hemisphere. J Cancer Res. 1916;1:21-48.
Holmes MD, Chen Wy, Feskanich D. Physical activity and survival after breast cancer diagnosis. JAMA. May 25, 2005;293(20):2479-86.JAMA May 25, 2005;293(20):2479-86.
Homem De Bittencourt JR PI, Curi R. Antiproliferative prostaglandins and the MRP/GS-X pump role in cancer immunosuppression and insight into new strategies in cancer gene therapy. Biochem Pharmacol 2001;62:811.
Hoption Cann S, Gunn H, Van Netten J, Van Netten C. Spontaneous Remission of Pancreatic Cancer. Case Rep Clin Prac Rev 2004;5:293-6.
Hoption Cann SA et al (2003) Dr. William Coley and tumour regression: a place in history or in the future? Postgrad Med J 2003;79:672-680.
Hoption Cann SA et al, Acute infections as a means of cancer prevention: Opposing effects to chronic infections? Cancer Detection and Prevention 30(2006)83-93.
Hrouda et al., "Immunotherapy of advanced prostate cancer: a phase I/II trial using Mycobacterium caccae (SRL172)" British Journal of Urology (1998) vol. 82, No. 4 pp. 568-573.
Interview Summary dated May 9, 2011 for U.S. Appl. No. 12/234,569 (4 pp.).
Jeannin et al., "OmpA targets dendritic cells, induces their maturation and delivers antigen into the MHC class I presentation pathway", Nature Immunology, 2000, 1(6): 502-509.
Jensen et al., "Macrophage Markers in Serum and Tumor Have Prognostic Impact in American Joint Committee on Cancer Stage I/II Melanoma", Journal of Clinical Oncology (2009) vol. 27, No. 20, pp. 3330-3337.
Jian L, Xie LP, Lee AH, Binns CW. Protective effects of green tea against prostate cancer: a case-control study in southeast China. Int J Cancer Jan. 1, 2004;108(1)130-5.
Johansson SL, Cohen SM. Epidemiology and etiology of bladder cancer. Semin Surg Oncol 1997;13:291-8.
Johnston B. Clinical effects of Coley's Toxins. I. Controlled study. II. A seven-year study. Cancer Chemotherapy Reports1962; 21:19-48.
Josefsson et al. 2001 (Protection against experimental *Staphylococcus aureus* arthritis by vaccination with clumping factor A, a voel virulence determinant; J of Infect. Dis. 184:1572-80).
Jurincic-Winklerc, Metz KA, Beuth J, Sippel J, Klippel KF. Effect of keyhole limpet hemocyanin (KLH) and bacillus Calmette-Guerin (BCG) instillation on carcinoma in situ of the urinary bladder. Anticancer Res Nov.-Dec. 1995; 15(6B): 2771-6.
Kapp JP. Microorganisms as antineoplastic agents in CNS tumors. Arch Neurol. 1983; 40:637-642.
Kassabov et al., "Inhibition of spontaneous pulmonary metastases of Lewis lung carcinoma by oral treatment with Respivax and Broncho-Vaxom", Cancer Immunol Immunother (1991) 33(5): 307-313.
Kelemen LE, Cerhan JR, Lim U, et al. Vegetables, fruit, and antioxidant-related nutrients and risk of non-Hodgkin lymphoma: a National Cancer Institute—Surveillance, Epidemiology, and End Results population-based case-control study. Am J Clint Nutr Jun. 2006;83(6):1401-10.
Keller R, Gehri R, Keist R et al. Cell Immunol 134(1991)249-55.
Keller R, Keist R, Frei K. Lymphokines and bacteria, that induce tumoricidal activity, trigger a different secretory response in macrophages. Eur J Immunol Mar. 1990b; 20(3):695-8.
Keller R, Keist R, Joller P, Mulsch A. Coordinate up- and down-modulation of inducible nitric oxide synthase, nitric oxide production, and tumoricidal activity in rat bone-marrow-derived mononuclear phagocytes by lipopolysaccharide and gram-negative bacteria. Biochem Ciophys Res Commun 1995;211:183-9.
Keller R, Keist R, Van Der Meide et al. J. Immunol 138(1987)2366-71.
Khan et al., "Oxidised lipoproteins may promote inflammation through the selective delay of engulfment but not binding of apoptotic cells by macrophages", Atherosclerosis (2003) vol. 171, pp. 21-29.
Kizaki M, Ogawa T, Watanabe Y, Toyama K. Spontaneous remission in hypoplastic acute leukemia. Keio J Med 1988; 37:299-307.
Kleef, Ralph et al., "Endotoxin and Exotoxin Induced Tumor Regression with Special Reference to Coley Toxins: A Survey of the Literature and Possible Immunological Mechanisms", Report to the National Cancer Institute Office of Alternative and Complementary Medicine (Aug. 1997).
Kohmel, K.F. et al., "Prior immunization of patients with malignant melanoma with vaccinia of BCG is associated with better survival. An European Organization for Research and Treatment of Cancer cohort study on 542 patients", Eur J Cancer 41:118-125 (2005).
Kohmel, K.F. et al., Treatment of advanced malignant melanoma by a pyrogenic bacterial lysate: a pilot study, Onkologie 14:411-417 (1991).
Kolmel K, Gefeller O, Haverkamp B. Febrile infections and malignant melanoma: results of a case-control study. Melanoma Res. 1992; 2:207-211.
Korzenik, "Is Crohn's disease due to defective immunity?", Gut. (2007) vol. 56, No. 1, pp. 2-5.
Kurzrock R. Cytokine deregulation in cancer. Biomed Pharmacother 2001;55:543.
Lee AH, Happerfield LC et al. Angiogenesis and inflammation in invasive carcinoma of the breast. J Clin Pathol 1997;50:669.
Leek RD, Harris AL. Tumor-associated macrophages in breast cancer. J Mammary Gland Biol Neoplasia 2002;7:177.
Leek RD, Hunt NC et al. Macrophage infiltration is associated with VEGF and EGFR expression in breast cancer. J Pathol 2000;190:430.
Leek RD, Landers RJ, Harris AL, Lewis CE. Necrosis correlates with high vascular density and focal macrophage infiltration in invasive carcinoma of the breast. Br. J Cancer 1999;79:991.
Lewis DE, Leek R, et al Cytokine regulation of angiogenesis in breast cancer: the role of tumor-associated macrophages. J Leukoc Biol 1995;57:747.

(56) References Cited

OTHER PUBLICATIONS

Lewis JS, Landers RJ et al. Expression of vascular endothelial growth factor by macrophages is up-regulated in poorly vascularized areas of breast carcinomas. J Pathol 2000;192:150.
Li, Z. et al., A clinical study on PA_MSHA vaccine used for adjuvant therapy of lymphoma and lung cancer, Hua Xi Vi Ke Da Xue Xue Bao 31(3):334-337 (Sep. 2000).
Likhite, "Rejection of Tumors and Metastases in Fischer 344 Rats Following Intratumor Administration of Killed Corynebacterium Parvum", Int. J. Cancer 14: 684-690 (1974).
Lin EY, Gouon-Evans V, et al. J Mammary Gland Biol Neoplasia 7(2002)147-162.
Liu S, Manson JE, Furing JE et al. Relation between a diet with a high glycemic load and plasma concentrations of high-sensitivity c-reactive protein in middle-aged women. Am J Clin Nutr 2002;75(3):492-8.
Luboshits G, Shina S, et al Elevated expression of the CC chemokine regulated on activation, normal T cell expressed and secreted (RANTES) in advanced breast carcinoma. Cancer Res 1999;59:4681.
Ludwig Lung Cancer Study Group. Adverse effect of intrapleural Coryebacterium parvum as adjuvant therapy in resected stage I and II non-small-cell carcinoma of the lung. J Thorac Cardiovasc Surg 1985; 89: 842-847.
Lunet N, Lacerda-Vieira A, Barros H. Fruit and vegetables consumption and gastric cancer: a systemic review and meta-analysis of cohort studies. Nutr. Cancer 2005;53(1):1-10.
Ma et al., "The M1 form of tumor-associated macrophages in non-small cell lung cancer is positively associated with survival time", BMC Cancer (2010) vol. 10, No. 112, pp. 1-9.
MacLean et al., "Vaccination strategies for the prevention of cervical cancer" Expert Review of Anticancer Therapy, Future Drugs, London (2005) vol. 5, No. 1.
Mager DL. "Bacteria and Cancer: Cause, Coincidence or Cure? A Review."Journal of Translational Medicine 5 Mar. 28, 2006 4[14]:doi:10.1186/1479-5876-4-14.
Malmberg KJ. Effective immunotherapy against cancer: a question of overcoming immune suppression and immune escape? Cancer Immunol Immunother 2004;53:879.
Mantovani A, Allavena P, Sica A. Tumour-associated macrophages as a prototypic type II polarized phagocyte population: role in tumour progression. Eur J Cancer 2004;40:1660.
Mantovani A, Allavena P, Sozzani S, Vecchi A, Locati M. Sica A. Chemokines in the recruitment and shaping of the leukocyte infiltrate of tumors. Semin Cancer Biol 2004;14:155.
Mantovani A, Sozzanit S, Locati M, Allavena P, Sica A. Macrophage polarization: Tumour-associated macrophages as a paradigm for polarized M2 mononuclear phagocytes. Trends Immunol 2002;23:549.
Mantovani et al., "Macrophages, innate immunity and cancer: balance, tolerance, and diversity", Current Opinion in Immunology (2010) vol. 22, No. 2, pp. 231-237.
Marks et al., "Crohn's Disease: an Immune Deficiency State", Clinic. Rev. Allerg. Immunol. (2010) vol. 38, pp. 20-31.
Marks et al., "Defective acute inflammation in Crohn's disease: a clinical investigation", Lancet (2006) vol. 367, pp. 668-678.
Marks, "Defective innate immunity in inflammatory bowel disease: a Crohn's disease exclusivity?" Current Opinion in Gastroenterology (2011) vol. 27, pp. 328-334.
Mastrangelo G, Fadda E, Milan G. Cancer increased after a reduction of infections in the first half of this century in Italy: etiologic and preventive implications. Eur J. Epidemiol 1998;14:749-54.
Mastrangelo G, Marzia V, Marcer G. Reduced lung cancer mortality in dairy farmers: is endotoxin exposure they key factor? Am J Ind Med 1996;30:601-9.
Matzker J, Steinberg A. Tonsillectomy and leukemia in adults (author's transl). Laryngol Rhinol Otol (Stuttg). 1976;55:721-5.
Maurya AK et al (1991) Differential induction of glutathione transferase isoenzymes of mice stomach by diallyl sulfide, a natural occurring anticarcinogen. Cancer Lett. 57:121-9.
Meier C, Schmitz S, Jick H. Association between acetaminophen or nonsteroidal anti-inflammatory drugs and risk of developing ovarian, breast, or colon cancer. Pharmacotherapy 2002;22:303-309.
Melbye M. et al. Human papillomavirus and the risk of anogenital cancer. Ugeskr Laeger 2002;164:5950-3.
Merchant JA, Ortmeyer C. Mortality of employees of two cotton mills in North Carolina. Chest 1981;79:6s-11S.
Mihich, E. and Neter, E., Necrotizing effects of Staphyloccus aureus extract on mouse sarcoma, Proc Soc Exp Bioi Med 106:97-101 (1961).
Moore KW, De Waal Malefyt R, et al. Interleukin-10 and the interleukin-10 receptor. Annu Rev Immunol 2001;19:683.
Morales A, Nickel JC (1992b). Immunotherapy for superficial bladder cancer. A developmental and clinical overview. Urol Clin North Am 1992; 19:549-556.
Mukhtar et al., "Tumor-associated macrophages in breast cancer as potential biomarkers for new treatments and diagnostics", Expert Rev. Mol. Diagn. (2011) vol. 11, No. 1, pp. 91-100.
Munoz et al., "The role of defective clearance of apoptotic cells in systemic autoimmunity", Nat. Rev. Rheumatol. (2010) vol. 6, pp. 280-289.
Myers, J. et al., Combined modality therapy of advanced nodular lymphomas: the role of nonspecific immunotherapy (MBV) as an important determinant of response and survival, Proc Am Soc Clin Oncol 24:56 (1983).
Nagata, "Rheumatoid polyarthritis caused by a defect in DNA degradation", Cytokine & Growth Factor Reviews (2008) vol. 19, pp. 295-302.
Nardone G, Morgner A. Helicobacter pylori and gastric malignancies. Helicobacter 2003;1(8 Suppl):44-52.
Nauts, H.C., "A review of the influence of bacterial infection and of bacterial products (Coley's toxins) on malignant tumors in man" Acta Med. Scand., (1953), 145 (Suppl. 276), 5-103.
Negus RP, Stamp GW et al. Quantitative assessment of the leukocyte infiltrate in ovarian cancer and its relationship to the expression of C-C chemokines. Am J Pathol 1997;150:1723.
Niwa Y, Akamatsu H et al. Correlation of tissue and plasma RANTES levels with disease course in patients with breast or cervical cancer. Clin Cancer Res 2001;7:285.
O'Brien et al., "SRL172 (killed Mycobacterium vaccae) in addition of standard chemotherapy improves quality of life without affecting survival, in patients with advanced non-small-cell lung cancer: phase III results", Annals of Oncology (2004) 15: 906-914.
O'Byrne KJ, Dalgleish AG. Chronic immune activation and inflammation as the cause of malignancy. Br J Cancer 2001;85:473.
Ochiai, T. et al., Postoperative adjuvant immunotherapy of gastric cancer with BCG-cell wall endoskeleton. Three- to six-year follow-up of a randomized clinical trial, Cancer Immunol Immunother 14:167-171 {1983).
Ogura, T., Immunotherapy of respectable lung cancer using Nocardia rubra cell wall skeleton, Gan to Kagaku Ryoho 10{2 Pt 2)366-372 (1983).
Ohno, R. et al., Randomized controlled study of chemoimmunotherapy of acute myelogenous leukemia (AML) in adults with Nocardia rubra cell-wall skeleton and irradiated allogeneic AML cells, Cancer 57(8):1483-1488 (Apr. 1986).
Ohshima H. Genetic and epigenetic damage induced by reactive nitrogen species: Implications in carcinogenesis. Toxicol Lett 2003;140-141:99-104.
Okamoto M, Sato M. Toll-like receptor signaling in anti-cancer immunity.J Med Invest 2003;50:9-24.
Okawa T, Kita M, Arai T, et al. Phase II randomized clinical trial of LC9018 concurrently used with radiation in the treatment of carcinoma of the uterine cervix. Its effect on tumor reduction and histology. Cancer Nov. 1, 1989;64[9]1769-76.
Omata M, Yoshida H. Prevention and treatment of hepatocellular carcinoma. Liver Transpl 2004; 10:S111-4.
Pace et al., "Inactivated whole-cell bacterial vaccines: current status and novel strategies", Vaccine, vol. 16, No. 16, pp. 1563-1574 (1998).
Pack, G., Note on the experimental use of rabies vaccine for melanomatosis, Arch Dermatol 62:694-695 (1950).
Pajonk F, Riedisser A, Henke A et al. The effects of tea extracts on proinflammatory signaling. BMC Med 2006:Dec. 1(4)28.

(56) References Cited

OTHER PUBLICATIONS

Palmieri C, MacGregor T, Girgis S, Vigushin D. Serum 25-hydroxyvitmain D levels in early and advanced breast cancer. J Clin Pathol 2006;0:1-3.
Papachristou D, Fortner J. Effect of postoperative wound infection of the course of stage II melanoma. Cancer 1979;43:1106-1111.
Paterson, Y. and Maciag, P.C. Listeria-based vaccines for cancer treatment. Curr. Opin. Mol. Ther 7(5):454-460 (Oct. 2005).
Pavia M, Pileggi C, Nobile CG, Angelillo IF. Association between fruit and vegetable consumption and oral cancer: a meta-analysis of observational studies. Am J Clint Nutr May 2006:83(5)1126-34.
Pawelec G. Tumour escape from the immune response. Cancer Immunol Immunother 2004:53:843.
Pawelec G. Tumour escape: antitumour effectors too much of a good thing? Cancer Immunol Immunother 2004:53:262.
Pelner, Fowler GA, Nauts HC. Effects of concurrent infections and their toxins on the course of leukemia. Acta Medica Scand. 1958; 162: 4-47 Cancer Research Institute, Inc, New York. Monograph #2.
Pfahlberg et al., "Inverse Association Between Melanoma and Previous Vaccinations Against Tuberculosis and Smallpox: Results of the FEBIM Study" The Society for Investigative Dermatology, Inc. (2002) 119 (3): 570-575.
Pischon T, Hankinson SE, Hotamisligil GS, et al. Habitual dietary intake of n-3 and n-6 fatty acids in relation to inflammatory markers among US men and women. Circulation 2003;108:155-60.
Platsoucas CD, Fincke JE, Pappas J et al. Immune responses to human tumors: development of tumor vaccines. Anticancer Res 2003;23:1969.
Pollard JW. Tumour-educated macrophages promote tumour progression and metastasis. Nat. Rev. Cancer (2004) 4,71-8.
Prasad KN et al (1999) High doses of multiple antioxidant vitamins: essential ingredients in improving the efficacy of standard cancer therapy. J Am Coll Nutr. 18:13-25.
Pukkala E, Weiderpass E. Time trends in socio-economic differences in incidence rates of cancers of the breast and female genital organs (Finland, 1971-1995). Int J Cancer 1999;81 :56-61.
Pulaski et al., "Cooperativity of *Staphylococcal aureus* Enterotoxin B Superantigen, Major Histocompatibility Complex Class II, and CD80 for Immunotherapy of Advanced Spontaneous Metastases in a Clinically Relevant Postoperative Mouse Breast Cancer Model" Cancer Research (2000) vol. 60, pp. 2710-2715.
Radford et al., "A recombinant *E. coli* vaccine to promote MHC class I-dependent antigen presentation: application to cancer immunotherapy", Gene Therapy, vol. 9, No. 21, pp. 1455-1463 (2002).
Rakel D, Rindfleisch A. Inflammation: Nutritional, Botanical, and Mind-Body Influences. Southern Medical Journal 98(3);302-10 Mar. 2005.
Ravindranath MH, Saravanan TS, Montecalaro CC, et al. Epicatechins purified from green tea (Camellia sinensis) differentially suppress growth of gender-dependent human cancer cell lines. Evid Based Complement Alternat Med Jun. 2006:3(2)237-247.
Reddy S, Rishi AK, Xu H et al. Mechanisms of curcurmin- and EGF-receptor related protein (ERRP)-dependent growth inhibition of colon cancer cells. Nutr Cancer 2006:55(2)185-194.
Riboli E, Norat T. Epidemiologic evidence of the protective effect of fruit and vegetables on cancer risk. Am J Clint Nutr Sep. 2003;78(3 Suppl):559S-569S.
Rolny et al., "HRG Inhibits Tumor Growth and Metastasis by Inducing Macrophage Polarization and Vessel Normalization through Downregulation of PIGF", Cancer Cell (2011) vol. 19, pp. 31-44.
Ruckdeschel JC, Codish SD, Starahan A, Mckneally MF. Postoperative empyema improves survival in lung cancer. New England Journal of Medicine. 1972; 287(20): 1013-1017.
Saemann MD, Bohmig GA, Osterreicher CH et al. Anti-inflammatory effects of sodium butyrate on human monocytes: potent inhibition of IL-12 and up-regulation of IL-10 production. FASEB Journal Dec. 2000(14)2380-2.

Saji J, Koike M, et al. Significant correlation of monocyte chemoattractant protein-1 expression with neovascularization and progression of breast carcinoma. Cancer 2001;92:1085.
Salvesen HB et al. Significance of tumor-associated macrophages, vascular endothelial growth factor and thrombospondin-1 expression for tumor angiogenesis and prognosis in endometrial carcinomas. Int J Cancer. 1999; 84:538-43.
Sandhu JK et al, Neutrophils, nitric oxide synthase, and mutations in the mutatect murine tumor model. Am J Pathol 2000;156:509-18.
Sapi E. The role of CSF-1 in normal physiology of mammary gland and breast cancer: an update. Exp Biol Med (Maywood) 2004;229:1.
Schleithoff SS, Zittermann A, Tenderich G, et al Vitamin D supplementation improves cytokine profiles in patients with congestive heart failure: a double-blind, randomized, placebo-controlled trial. Am J Clin Nutr. Apr. 2006;83(4);754-9.
Schmid et al., "Myeloid Cells in the Tumor Microenvironment: Modulation of Tumor Angiogenesis and Tumor Inflammation", Journal of Oncology (2010) pp. 1-10.
Schwartsburd PM. Chronic inflammation as inductor of pro-cancer microenvironment: pathogenesis of dysregulated feedback control. Cancer Metastasis Rev 2003;22:95.
Schwartz GG, Skinner HG. Vitamin D status and cancer: new insights. Curr Opin Clin Nutr Metab Care 2007:10(1)6-11.
Seely D, Mills EJ, Wu P et al. The effects of green tea consumption on incidence of breast cancer and recurrence of breast cancer: a systemic review and meta-analysis. Integ Cancer Ther 2005:4(2)144-155.
Shepherd FA: Alternatives to chemotherapy and radiotherapy as adjuvant treatment for lung cancer. Lung Cancer 1997; 17 (suppl):5121-5136.
Sica A, Saccani A, Mantovani A. Tumour-associated macrophages: a molecular perspective. Int Immunopharmacol 2002;2:1045.
Siegel PM, Massague J. Cytostatic and apoptotic actions of TGFβin homeostasis and cancer. Nat Rev Cancer 2003:3:807.
Smith, R.E. et al., Randomized trial of adjuvant therapy in colon carcinoma: 10-Year results of NSABP protocol C-01, J. NCI96(15)1128-1132 (2004).
Smith RL, Salsbury CG, Gilliam AG. Recorded and expected mortality among Navajo, with special reference to cancer. J Natl Cancer Inst 1956;17:77-89.
Smith RL. Recorded and expected mortality among Indians in the United States with special reference to cancer. J Natl Cancer Inst 1957;18:385-96.
Smolen et al. 2010 (Treating rheumatoid arthritis to target: recommendations of an international task force; Ann Rheum Dis; 69:631-637).
Solinas et al., "Tumor-associated macrophages (TAM) as major players of the cancer-related inflammation", Journal of Leukocyte Biology (2009) vol. 86, pp. 1065-1073.
Standiford et al., "TGF-β-Induced IRAK-M expression in tumor-associated macrophages regulates lung tumor growth", Oncogene (2011) vol. 30, No. 21, pp. 1-10.
Stephenson HE, Delmez JA, Ren Den DI, et al. Host immunity and spontaneous regression of cancer evaluated by computerized data reduction study. Surg Gynecol Obstet. Oct. 1971;133(4):649-55.
Sumida et al., "Rheumatoid Arthritis and Apoptosis", Internal Medicine (1998) vol. 37, No. 2, pp. 184-188.
Sunderkotter C, Steinbrink K, Goebeler M, et al. Macrophages and angiogenesis. J Leukoc Biol 1994(55)410-422.
Sur, P. and Dastidar, A., Role of Mycobacterium was adjuvant treatment of lung cancer (non-small cell lung cancer), J. Indian Med Assoc 101 (2):118-120 (Feb. 2003).
Sylvester, R.J. et al., Intravesical Bacillus Calmette-Guerin Reduces the Risk of Progression in Patients With Superficial Bladder Cancer: A Meta-Analysis of the Published Results of Randomized Clinical Trials, The Journal of Urology 168:1967-1970 (Nov. 2002).
Takahashi Y., Bucana C. D., Liu W. et al. Platelet-derived growth factor in human colon cancer angiogenesis: role of infiltrating cells. J Natl Cancer Inst 1996; 88: 1146±1151.
Takanami I., Takeuchi K., Kodaira S. Tumor-associated macrophage infiltration in pulmonary adenocarcinoma: association with angiogenesis and poor prognosis. Oncology 1999; 57: 138±142.

(56) References Cited

OTHER PUBLICATIONS

Takita H. Effect of postoperative empyema on survival of patients with bronchogenic carcinoma. J Thorac Cardiovasc Surg. 1970; 59:642-44.
Tanaka J et al (1979) Vitamin E and immune response. Immunology 38:727.
Thangapazham RL, Sharma A Maheshwari RK. Multiple molecular targets in cancer chemoprevention by curcumin. AAPS J Jul. 7, 2006:8(3)E443-9.
Thompson Lu, Chen JM, Li T, et al. Dietary flaxseed alters tumor biological markers in postmenopausal breast cancer. Clin Cancer Res May 15, 2005:11(10)3828-3835.
Thun MJ, Henley SJ, Gansier T. Inflammation and cancer: an epidemiological perspective. Novartis Found Symp 2004;256:6.
Tilley SL, Coffman TM, Koller BH. Mixed messages: modulation of inflammation and immune responses by prostaglandins and thromboxanes. J Clin Invest 2001;108:15.
Trampuz et al. 2005 (Prosthetic joint infections: update in diagnosis and treatment; Swiss Med Wkly; 135:243-251).
Ueno T, Tio M, et al. Significance of macrophage chemoattractant protein-1 in macrophage recruitment, angiogenesis, and survival in human breast cancer. Clin Cancer Res 2000;6:3282.
Uyl-De Groot, C.A. et al., Immunotherapy with autologous tumor ceii-BCG vaccine in patients with colon cancer: a prospective study of medical and economic benefits, Vaccine 23(17-18):2379-2387 (2005).
Van Netten J. P., George E. J., Ashmead B. J. et al. Macrophage tumor cell associations: a factor in metastasis of breast cancer? J Leukoc Biol 1993; 54: 360±362.
Van Netten JP et al, Macrophage-tumour cell associations in breast cancer. Lancet 1993;342:872-3.
Van Netten JP et al. Macrophages and their putative significance in human breast cancer. Br J Cancer. 1992; 66:220-1.
Velicer CM et al. Antibiotic use in relation to the risk of breast cancer. JAMA. 2004; 18;291(7):880-1.
Verdrengh et al. 2007 (Addition of bisphosphonate to antibiotic and anti-inflammatory treatment reduces bone resorption in experimental *Staphylococcus aureus*-induced Arthritis; Journal of Orthopaedic Research, 2007, pp. 304-310).
Viallard JF, Denis D, Texier-Maugein J, et al. Disseminated infection after bacilli Camille-Guerin instillation for treatment of bladder cancer. Clin Infect Dis 1999; 29:451-2.
Walker, Richard I., "Considerations for development of whole cell bacterial vaccines to prevent diarrheal diseases in children in developing countries", Vaccine, vol. 23, pp. 3369-3385 (2005).
Wallace JM. Nutritional and botanical modulation of the inflammatory cascade—eicosanoids, cyclooxygenases, and lipoxygenases—as an adjunct in cancer therapy. Integr Cancer Ther. Mar. 2002;1(1):7-37.
Wang W, Goswami S, et al. Tumor cells caught in the act of invading: their strategy for enhanced cell motility. Trends Cell Biol 15(2005)138-145.
Warburton DE, Nicol CW, Bredin SS. Health benefits of physical activity: the evidence. CMAJ Mar. 14, 2006 ;174(6):801-9.
Watanabe E, Matsuyama H, Matsuda K, et al. Urinary interleukin-2 may predict clinical outcome of intravesical bacillus Calmette-Guerin immunotherapy for carcinoma in-situ of the bladder. Cancer Immunol Immunother 2003;52:481-6.
Weitzman SA et al, Phagocytes as carcinogens: malignant transformation produced by human neutrophils. Science 1985;227:1231-3.
Williams CS, Mann M, Dubois RN. The role of cyclooxygenases in inflammation, cancer and development. Oncogene 1999;18:7908.
Wojtowicz-Praga S. Reversal of tumor-induced immunosuppression by TGFβinhibitors. Invest New Drugs 2003;21:21.
Woo EY, Yeh H, Chu CS et al. Cutting edge: regulatory T cells from lung cancer patients directly inhibit autologous T cell proliferation. J Immunol 2002;168:4272-4276.
Wyckoff J, Wang W, et al. A paracrine loop between tumor cells and macrophages is required for tumor cell migration in mammary tumors. Cancer Res 64(2004)7022-7029.
Yasumoto, K. and Yamamura, Y., Randomized clinical trial of non-specific immunotherapy with cell-wall skeleton of Nocardia rubra, Biomed Pharmacother 38(1 ):48-54 (1984).
Yu JL, Rak JW. Host microenvironment in breast cancer development: inflammatory and immune cells in tumour angiogenesis and arteriogenesis. Breast Cancer Res 2003;5:83.
Yue FY, Dummer R, et al. Interleukin 10 is a growth factor for human melanoma cells and down-regulates HLA class-I, HLA class-II and ICAM-1 molecules. Int J Cancer 1997;71:630.
Zhou Y et al (1998) Mechanism for the suppression of the mammalian stress response by genistein, an anticancer phytoestrogen from soy. J Natl Cancer Inst. 90:381-8.
Lee et al., Evaluation of the acute and subchronic toxic effects in mice, rats, and monkeys of the genetically engineered and *Escherichia coli* cytosine deaminase gene-incorporated Salmonella strain, TAPET-CD, being developed as an antitumor agent, Int J Toxicol (2001), 20(4):207-217.
Wolmark et al., Postoperative adjuvant chemotherapy or BCG for colon cancer: results from NSABP protocol C-01, J Natl Cancer Inst (1988), 80(1):30-36.
Martin et al., Enhanced *Escherichia coli* adherence and invasion in Crohn's disease and colon cancer, Gastroenterology (2004), 127(1):80-93.
Kruis et al., "Double-blind comparison of an oral *Escherichia coli* preparation and mesalazine in maintaining remission of ulcerative colitis", Alimentary Pharmacology and Therapeutics, vol. 11, No. 5, pp. 853-858 (1997).
Torres et al., "Evaluation of Formalin-Inactivated Clostridium difficile Vaccines Administered by Parenteral and Mucosal Routes of Immunization in Hamsters", Infection and Immunity, vol. 63, No. 12, pp. 4619-4627 (1995).
Guideline for the Care and Use of Mammals in Neuroscience and Behavioral Research, Published by National Research Council in 2003, pp. 111-113.
Fujihara et al., Intratumoral injection of inactivated Sendai virus particles elicits strong antitumor activity by enhancing local CXCL10 expression and systemic NK cell activation, Cancer Immunol Immunother (2008), 57 (1):73-84.
Kurokawa et al., Inactivated Sendai virus particles eradicate tumors by inducing immune responses through blocking regulatory T cells, Cancer Res (2007), 67(1):227-236.
Smith et al., Disordered macrophage cytokine secretion underlies impaired acute inflammation and bacterial clearance in Crohn's disease, J Exp Med (2009), 206(9):1883-1897.
Cross et al., Active Immunization with a Detoxified *Escherichia coli* J5 Lipopolysaccharide Group B Meningococcal Outer Membrane Protein Complex Vaccine Protects Animals from Experimental Sepsis, J Infect Dis. (2001) 183 (7): 1079-1086.
Brockstedt et al., Listeria-based cancer vaccines that segregate immunogenicity from toxicity, PNAS (2004), 101(38):13832-13837.
Bischoff et al., An adenovirus mutant that replicates selectively in p53-deficient human tumor cells, Science. Oct. 18, 1996;274(5286):373-6.
Sznol et al., Use of preferentially replicating bacteria for the treatment of cancer, J Clin Invest. Apr. 15, 2000; 105(8): 1027-1030.
Moens et al., Cross-Protective Immunity against Heterologous *Streptococcus pneumoniae*, Infect Immun. May 2012; 80(5): 1944-1945.
Varghese et al., Oncolytic herpes simplex virus vectors for cancer virotherapy, Cancer Gene Ther. Dec. 2002;9(12):967-78.
Mackie et al., Intralesional injection of herpes simplex virus 1716 in metastatic melanoma, Lancet. Feb. 17, 2001;357(9255):525-6.
Markert et al., Conditionally replicating herpes simplex virus mutant, G207 for the treatment of malignant glioma: results of a phase I trial, Gene Ther. May 2000;7(10):867-74.

\* cited by examiner

Survival of Stage 4 Prostate Cancer Patients with Bone Metastases Surgery or Radiation to Destroy Prostate Figure 8: Stage 4 Colorectal Cancer Treatment Comparison Figure 12: Stage 3B & 4 Lung Cancer Survival from CIH First Visit

TISSUE TARGETED ANTIGENIC ACTIVATION OF THE IMMUNE RESPONSE TO TREAT CANCERS

CROSS-REFERENCE TO RELATED APPLICATIONS

This application is a continuation of U.S. application Ser. No. 13/894,343 filed on May 14, 2013; which application is a continuation of U.S. application Ser. No. 12/843,296 filed on Jul. 26, 2010, issued as U.S. Pat. No. 8,501,198 on Aug. 6, 2013; which application is a Continuation-in-Part application of U.S. application Ser. No. 12/234,569 filed on Sep. 19, 2008, issued as U.S. Pat. No. 8,034,359 on Oct. 11, 2011; which application is: (I) a Continuation-in-Part application of U.S. application Ser. No. 11/553,972 filed on Oct. 27, 2006 now abandoned; which application is a Continuation-in-Part application of International Application Serial No. PCT/CA05/00812 filed on May 30, 2005; which International application pursuant to 35 U.S.C. §119 (e), claims priority to the filing date of U.S. Provisional Patent Application Ser. No. 60/577,206 filed Jun. 7, 2004; and (II) a Continuation-in-Part application of International Application Serial No. PCT/CA07/01915 filed on Oct. 25, 2007. The disclosures of all of the applications listed in this paragraph are herein incorporated by reference.

FIELD OF THE INVENTION

In various aspects, the invention relates to immunological cancer therapies. In alternative embodiments, the invention provides methods of formulating antigenic microbial composition and methods of using the antigenic compositions to treat cancers.

BACKGROUND OF THE INVENTION

More than one in three people in the developed nations are diagnosed with cancer. More than one in four die from it. Therapies for cancer have primarily relied upon treatments such as surgery, chemotherapy, and radiation. These approaches however, while beneficial for some types and stages of cancer, have proved to be of limited efficacy in many common types and stages of cancers. For example, surgical treatment of a tumor requires complete removal of cancerous tissue to prevent reoccurrence. Similarly, radiation therapy requires complete destruction of cancerous cells. This is difficult since, in theory, a single malignant cell can proliferate sufficiently to cause reoccurrence of the cancer. Also, both surgical treatment and radiation therapy are directed to localized areas of cancer, and are relatively ineffective when the cancer metastasizes. Often surgery or radiation or both are used in combination with systemic approaches such as chemotherapy. Chemotherapy however has the problem of non-selectivity with the concomitant problem of deleterious side effects, as well as the possibility of the cancer cells developing resistance to the drugs.

The inherent shortcomings of chemotherapy have led to disparate efforts to recruit various aspects of the immune system to treat cancers. A subset of this work relates to immunization with microbial vaccines. Although this approach has a relatively long history, as discussed in more detail below, the field is a very confused mixture of sometimes intriguing successes mixed with many failures that together have failed to produce a cohesive therapeutic approach amenable to widespread clinical adoption.

Alternative approaches for the treatment of cancers have included therapies that involve augmentation of immune system function such as cytokine therapy (e.g., recombinant interleukin 2 and gamma interferon for kidney cancers), dendritic cell therapy, autologous tumor vaccine therapy, genetically-altered vaccine therapy, lymphocyte therapy, and microbial vaccine therapies. Microbial vaccines have been used to vaccinate subjects against pathogens that are associated with cancer, such as the human papillomavirus. Immunostimulatory microbial vaccines that are not targeted to cancer-causing organisms, i.e., non-specific immunostimulatory vaccines, such as pyrogenic vaccines, have a long clinical history that includes reports of successes and failures in treating a variety of cancers. For example, Coley's vaccine (a combination of *Streptococcus pyogenes* and *Serratia marcescens*) has been reported to be helpful for the treatment of sarcomas, and lymphomas (Nauts H C, Fowler G A A, Bogato F H. A review of the influence of bacterial infection and of bacterial products [Coley's toxins] on malignant tumors in man. Acta Med Scand 1953; 145 [Suppl. 276]:5-103). Clinical trials have reportedly demonstrated the benefit of Coley's vaccine treatment for lymphoma and melanoma (Kempin S, Cirrincone C, Myers J et al: Combined modality therapy of advanced nodular lymphomas: the role of nonspecific immunotherapy [MBV] as an important determinant of response and survival. Proc Am Soc Clin Oncol 1983; 24:56; Kolmel K F, Vehmeyer K. Treatment of advanced malignant melanoma by a pyrogenic bacterial lysate: a pilot study. Onkologie 1991; 14:411-17).

It has been suggested that the effectiveness of some non-specific bacterial cancer vaccines is attributable to particular bacterial components or products, such as bacterial DNA or endotoxin (LPS), or because they induce the expression of particular factors, such as tumor necrosis factor (TNF) or interleukin-12. A correspondingly broad range of physiological mechanisms have been ascribed to such treatments, ranging from generalized effects of fever to anti-angiogenic mechanisms. In accordance with these various principles, a wide variety of microbial vaccines have been tested as general immune stimulants for the treatment of cancer. While most have shown negative results, a few have shown some intriguing positive results in certain contexts, as follows:

Intradermal BCG (*Mycobacterium bovis*) vaccine treatment has been reported to be effective for the treatment of stomach cancer (Ochiai T, Sato J, Hayashi R, et al: Postoperative adjuvant immunotherapy of gastric cancer with BCG-cell wall endoskeleton. Three- to six-year follow-up of a randomized clinical trial. Cancer Immunol Immunother 1983; 14:167-171) and colon cancer (Smith R E, Colangelo L, Wieand H S, Begovic M, Wolmark N. Randomized trial of adjuvant therapy in colon carcinoma: 10-Year results of NSABP protocol C-01. J. NCI-2004; 96[15]:1128-32; Uyl-de Groot C A, Vermorken J B, Hanna M G, Verboon P, Groot M T, Bonsel G J, Meijer C J, Pinedo H M. Immunotherapy with autologous tumor cell-BCG vaccine in patients with colon cancer: a prospective study of medical and economic benefits Vaccine 2005; 23[17-18]:2379-87).

*Mycobacterium* w vaccine therapy, in combination with chemotherapy and radiation, was found to significantly improve quality of life and response to treatment in patients with lung cancer (Sur P, Dastidar A. Role of *Mycobacterium* w as adjuvant treatment of lung cancer [non-small cell lung cancer]. J Indian Med Assoc 2003 February; 101[2]:118-120). Similarly, *Mycobacterium vaccae* vaccine therapy was found to improve quality of life (O'Brien M, Anderson H, Kaukel E, et al. SRL172 [killed *Mycobacterium vaccae*] in addition to standard chemotherapy improves quality of life without affecting survival, in patients with advanced non-small-cell lung cancer: phase III results. Ann Oncol 2004 June; 15[6]; 906-14) and symptom control (Harper-Wynne C, Sumpter K, Ryan C, et al. Addition of SRL 172 to standard chemotherapy in small cell lung cancer [SCLC] improves symptom control. Lung Cancer 2005 February; 47[2]:289-90) in lung cancer patients.

*Corynebacterium parvum* vaccine was linked with a trend towards improved survival for the treatment of melanoma (Balch C M, Smalley R V, Bartolucci A A, et al. A randomized prospective trial of adjuvant *C. parvum* immunotherapy in 260 patients with clinically localized melanoma [stage I]. Cancer 1982 Mar. 15; 49[6]:1079-84).

Intradermal *Streptococcus pyogenes* vaccine therapy was found to be effective for the treatment of stomach cancer (Hanaue H, Kim D Y, Machimura T, et al. Hemolytic streptococcus preparation OK-432; beneficial adjuvant therapy in recurrent gastric carcinoma. Tokai J Exp Clin Med 1987 November; 12[4]:209-14).

*Nocardia rubra* vaccine was found to be effective for the treatment of lung cancer (Yasumoto K, Yamamura Y. Randomized clinical trial of non-specific immunotherapy with cell-wall skeleton of *Nocardia rubra*. Biomed Pharmacother 1984; 38[1]:48-54; Ogura T. Immunotherapy of respectable lung cancer using *Nocardia rubra* cell wall skeleton. Gan To Kagaku Ryoho 1983 February; 10[2 Pt 2]:366-72) and linked to a trend to improved survival for the treatment acute myelogenous leukemia (Ohno R, Nakamura H, Kodera Y, et al. Randomized controlled study of chemoimmunotherapy of acute myelogenous leukemia [AML] in adults with *Nocardia rubra* cell-wall skeleton and irradiated allogeneic AML cells. Cancer 1986 Apr. 15; 57[8]:1483-8).

*Lactobacillus casei* vaccine treatment combined with radiation was found to more effective for the treatment of cervical cancer than radiation alone. (Okawa T, Kita M, Arai T, et al. Phase II randomized clinical trial of LC9018 concurrently used with radiation in the treatment of carcinoma of the uterine cervix. Its effect on tumor reduction and histology. Cancer 1989 Nov. 1; 64[9]:1769-76)

*Pseudomonas aeruginosa* vaccine treatment was found to increase the effectiveness of chemotherapy in the treatment of lymphoma and lung cancer (Li Z, Hao D, Zhang H, Ren L, et al. A clinical study on PA_MSHA vaccine used for adjuvant therapy of lymphoma and lung cancer. Hua Xi Yi Ke Da Xue Xue Bao September; 31 [3]:334-7).

Childhood vaccination with the smallpox vaccine (i.e., Vaccinia virus vaccine) was found to be associated with a decreased risk of melanoma later in life (Pfahlberg A, Kolmel K F, Grange J M. et al. Inverse association between melanoma and previous vaccinations against tuberculosis and smallpox: results of the FEBIM study. J Invest Dermatol 2002[119]: 570-575) as well as decreased mortality in those patients who did develop melanoma (Kolmel K F, Grange J M, Krone B, et al. Prior immunization of patients with malignant melanoma with vaccinia or BCG is associated with better survival. European Organization for Research and Treatment of Cancer cohort study on 542 patients. Eur J Cancer 41[2005]:118-125).

Treatment with rabies virus vaccine was found to result in temporary remission in 8 of 30 patients with melanoma (Higgins G, Pack G. Virus therapy in the treatment of tumors. Bull Hosp Joint Dis 1951; 12:379-382; Pack G. Note on the experimental use of rabies vaccine for melanomatosis. Arch Dermatol 1950; 62:694-695).

In spite of substantial efforts to engage the immune system to combat cancers using non-specific immunostimulatory microbial vaccines, the vast majority of these efforts have failed and there is little clinical or research evidence of widespread success in improving the survival of cancer patient populations. While it has been recognized that immunostimulatory microbial vaccine approaches have promise, it has also been recognized that significant challenges characterize the field (Ralf Kleef, Mary Ann Richardson, Nancy Russell, Cristina Ramirez. "Endotoxin and Exotoxin Induced Tumor Regression with Special Reference to Coley Toxins: A Survey of the Literature and Possible Immunological Mechanisms." Report to the National Cancer Institute Office of Alternative and Complementary Medicine August 1997; DL Mager. "Bacteria and Cancer: Cause, Coincidence or Cure? A Review." Journal of Translational Medicine 28 Mar. 2006 4[14]:doi:10.1186/1479-5876-4-14). There remains a need for alternative approaches to the formulation, administration and methodology of antigenic compositions for the treatment of cancer.

SUMMARY OF THE INVENTION

In one aspect, the invention provides methods for formulating an immunogenic composition for treating a cancer situated in a specific organ or tissue in a mammal, such as human patient. The method may include selecting at least one microbial pathogen that is naturally pathogenic in the organ or tissue of the mammal within which the cancer is situated. An antigenic composition may be produced that includes antigenic determinants that together are specific for or characteristic of the microbial pathogen.

A diagnostic step may be used to identify the specific organ or tissue within which the cancer is situated, prior to producing the antigenic composition targeted to the site of the cancer. The site of the cancer may be a primary site, or a secondary site of metastasis. The antigenic composition may be sufficiently specific that it would be capable of eliciting an immune response in the mammal specific to the microbial pathogen. The antigenic composition may be a bacterial composition, for example derived from a bacterial species or species that are endogenous to the flora of the patient or from an exogenous species or species. In alternative embodiments, the antigenic composition may be derived from a virus or viruses. Accordingly, the microbial pathogen from which the antigenic composition is derived may be a virus. The microbial pathogen may be killed. In alternative embodiments, the microbial pathogen may be live or attenuated. Immunogenic compositions of the invention may also be formulated or administered with anti-inflammatory modalities, such as an NSAID. The site of administration may be at a site distant from the site of the cancer, for example in an organ or tissue that is not the organ or tissue within which the cancer is situated, for example the skin or subcutaneous tissue.

The antigenic composition may for example be formulated for subcutaneous injection, intradermal injection or oral administration. In embodiments for subcutaneous or intradermal injection, the dosing or formulation of the antigenic composition may be adjusted in order to produce a localized immune reaction visible in the skin at the site of administration, for example an area of inflammation from 2 mm to 100 mm in diameter appearing, for example, 2-48 hours after administration and lasting, for example, 2-72 hours or longer. The antigenic composition may be formulated for repeated subcutaneous or intradermal administration, for example at alternating successive sites.

In some embodiments, the invention involves methods of treating a mammal for a cancer situated in a tissue or an organ. In alternative embodiments, the treatment may anticipate the development of the cancer in the tissue, for example if the site of a primary tumour suggests the likelihood of metastasis to a particular tissue or organ, then the patient may be prophylactically treated to prevent or ameliorate metastasis to that tissue or organ. The method may include administering to the subject an effective amount of an antigenic composition comprising antigenic determinants that together are specific for at least one microbial pathogen. An aspect of the invention involves the use of a microbial pathogen that is pathogenic in the specific organ or tissue of the mammal within which the cancer is situated. The antigenic composition may be administered, for example by subcutaneous or intradermal injection at an administration site, in successive doses given at a dosage interval, for example of between one hour and one month, over a dosage duration, for example of at least 2 weeks, 2 months, 6 months, 1, 2, 3, 4, or 5 years or longer. Each injection dose may for example be metered so that it is effective to cause visible localized inflammation at the administration site, appearing, for example, 2-48 hours after injection.

The invention provides in part methods of treating cancers of a specific organ or tissue in a subject by administering one or more antigens of one or more microbial pathogens, such as bacterial or viral species that are pathogenic in the specific organ or tissue.

In alternative embodiments, the pathogenic microbial species may be capable of causing infection naturally, (i.e., without human intervention) in the specific organ or tissue in a healthy subject, or may have caused an infection in the specific organ or tissue in a healthy subject. In alternative embodiments, the antigen may be administered by administering a whole microbial species. In alternative embodiments, the method may for example include administering at least two or more microbial species, or administering at least three or more microbial species, and the microbes may be bacteria or viruses. In alternative embodiments, the method may further include administering a supplement or an adjuvant. An aspect of the invention involves administering antigenic compositions so as to elicit an immune response in said subject.

In alternative embodiments, the microbial pathogen in the antigenic composition may be killed, and thus rendered non-infectious. In some embodiments, the antigenic composition is administered at a site distant from the cancer site, and in selected embodiments of this kind, methods of the invention may be carried out so that they do not produce infection at the cancer site.

A "cancer" or "neoplasm," as used herein, is any unwanted growth of cells serving no physiological function. In general, a cancer cell has been released from its normal cell division control, i.e., a cell whose growth is not regulated by the ordinary biochemical and physical influences in the cellular environment. Thus, "cancer" is a general term for diseases characterized by abnormal uncontrolled cell growth. In most cases, a cancer cell proliferates to form clonal cells that are malignant. The lump or cell mass, "neoplasm" or "tumor," is generally capable of invading and destroying surrounding normal tissues. By "malignancy" is meant an abnormal growth of any cell type or tissue that has a deleterious effect in the organism having the abnormal growth. The term "malignancy" or "cancer" includes cell growths that are technically benign but which carry the risk of becoming malignant. Cancer cells may spread from their original site to other parts of the body through the lymphatic system or blood stream in a process known as "metastasis." Many cancers are refractory to treatment and prove fatal. Examples of cancers or neoplasms include, without limitation, transformed and immortalized cells, tumors, carcinomas, in various organs and tissues as described herein or known to those of skill in the art.

A "cell" is the basic structural and functional unit of a living organism. In higher organisms, e.g., animals, cells having similar structure and function generally aggregate into "tissues" that perform particular functions. Thus, a tissue includes a collection of similar cells and surrounding intercellular substances, e.g., epithelial tissue, connective tissue, muscle, nerve. An "organ" is a fully differentiated structural and functional unit in a higher organism that may be composed of different types of tissues and is specialized for some particular function, e.g., kidney, heart, brain, liver, etc. Accordingly, by "specific organ, tissue, or cell" is meant herein to include any particular organ, and to include the cells and tissues found in that organ.

"Pathogenic" agents are agents, such as microbes, such as bacteria or viruses, that are known to cause infection in a host in nature, and in this sense, "pathogenic" is used in the context of the present invention to mean "naturally pathogenic". Although a wide variety of microbes may be capable of causing infection under artificial conditions, such as artificial innoculations of a microbe into a tissue, the range of microbes that naturally cause infection is necessarily limited, and well established by medical practice.

An "infection" is the state or condition in which the body or a part of it is invaded by a pathogenic agent (e.g., a microbe, such as a bacterium) which, under favorable conditions, multiplies and produces effects that are injurious (Taber's Cyclopedic Medical Dictionary, 14th Ed., C.L. Thomas, Ed., F.A. Davis Company, PA, USA). An infection may not always be apparent clinically and may result in only localized cellular injury. Infections may remain subclinical, and temporary if the body's defensive mechanisms are effective. Infections may spread locally to become clinically apparent as an acute, a subacute, or a chronic clinical infection or disease state. A local infection may also become systemic when the pathogenic agent gains access to the lymphatic or vascular system (On-Line Medical Dictionary, http:// followed by cancerweb. followed by ncl.ac. followed by uk/ followed by omd/). Infection is usually accompanied by inflammation, but inflammation may occur without infection.

"Inflammation" is the characteristic tissue reaction to injury (marked by swelling, redness, heat, and pain), and includes the successive changes that occur in living tissue when it is injured. Infection and inflammation are different conditions, although one may arise from the other (Taber's Cyclopedic Medical Dictionary, supra). Accordingly, inflammation may occur without infection and infection may occur without inflammation (although inflammation typically results from infection by pathogenic bacteria or viruses).

Inflammation is characterized by the following symptoms: redness (rubor), heat (calor), swelling (tumor), pain (dolor). Localized visible inflammation on the skin may be apparent from a combination of these symptoms, particularly redness at a site of administration.

Various subjects may be treated in accordance with alternative aspects of the invention. A "subject" is an animal, e.g., a mammal, to whom the specific pathogenic bacteria, bacterial antigens, viruses, viral antigens or compositions thereof of the invention may be administered. Accordingly, a subject may be a patient, e.g., a human, suffering from a cancer, or suspected of having a cancer, or at risk for developing a cancer. A subject may also be an experimental animal, e.g., an animal model of a cancer, as is described in Example 5. In some embodiments, the terms "subject" and "patient" may be used interchangeably, and may include a human, a non-human mammal, a non-human primate, a rat, mouse, dog, etc. A healthy subject may be a human who is not suffering from a cancer or suspected of having a cancer, or who is not suffering from a chronic disorder or condition. A "healthy subject" may also be a subject who is not immunocompromised. By immunocompromised is meant any condition in which the immune system functions in an abnormal or incomplete manner. Immunocompromisation may be due to disease, certain medications, or conditions present at birth. Immunocompromised subjects may be found more frequently among infants, the elderly, and individuals undergoing extensive drug or radiation therapy.

An "immune response" includes, but is not limited to, one or more of the following responses in a mammal: induction or activation of antibodies, neutrophils, monocytes, macrophages, B cells, T cells (including helper T cells, natural killer cells, cytotoxic T cells, γδ T cells), such as induction or activation by the antigen(s) in a composition or vaccine, following administration of the composition or vaccine. An immune response to a composition or vaccine thus generally includes the development in the host animal of a cellular and/or antibody-mediated response to the composition or vaccine of interest. In some embodiments, the immune response is such that it will also result in slowing or stopping the progression of a cancer in the animal.

Various aspects of the invention involve treating cancers. In this context, treatment may be carried out so as to provide a variety of outcomes. For example, treatment may: provoke an immune reaction that is effective to inhibit or ameliorate the growth or proliferation of a cancer; inhibit the growth or proliferation of cancer cells or tumors; cause remission of a cancer; improve quality of life; reduce the risk of recurrence of a cancer; inhibit metastasis of a cancer; or, improve patient survival rates in a patient population. In this context, extending the life expectancy of a patient, or patient population, means to increase the number of patients who survive for a given period of time following a particular diagnosis. In some embodiments, treatment may be of patients who have not responded to other treatments, such as patients for whom a chemotherapy or surgery has not been an effective treatment. Treatment in alternative embodiments may for example be before or after onset of cancer. For example prophylactic treatment may be undertaken, for example of patients diagnosed as being at risk of a particular cancer. For example a patient having a genetic or lifestyle predisposition to cancer of a certain tissue or organ may be treated with an immunogenic composition comprising antigenic determinants of a pathogen that is pathogenic in that organ or tissue. Similarly, the prophylactic treatment of metastasis may be undertaken, so that patients having a primary cancer with a propensity to metastasize to a particular tissue or organ may be treated with an immunogenic composition comprising antigenic determinants of a pathogen that is pathogenic in that organ or tissue.

DETAILED DESCRIPTION OF THE INVENTION

Figure 1:
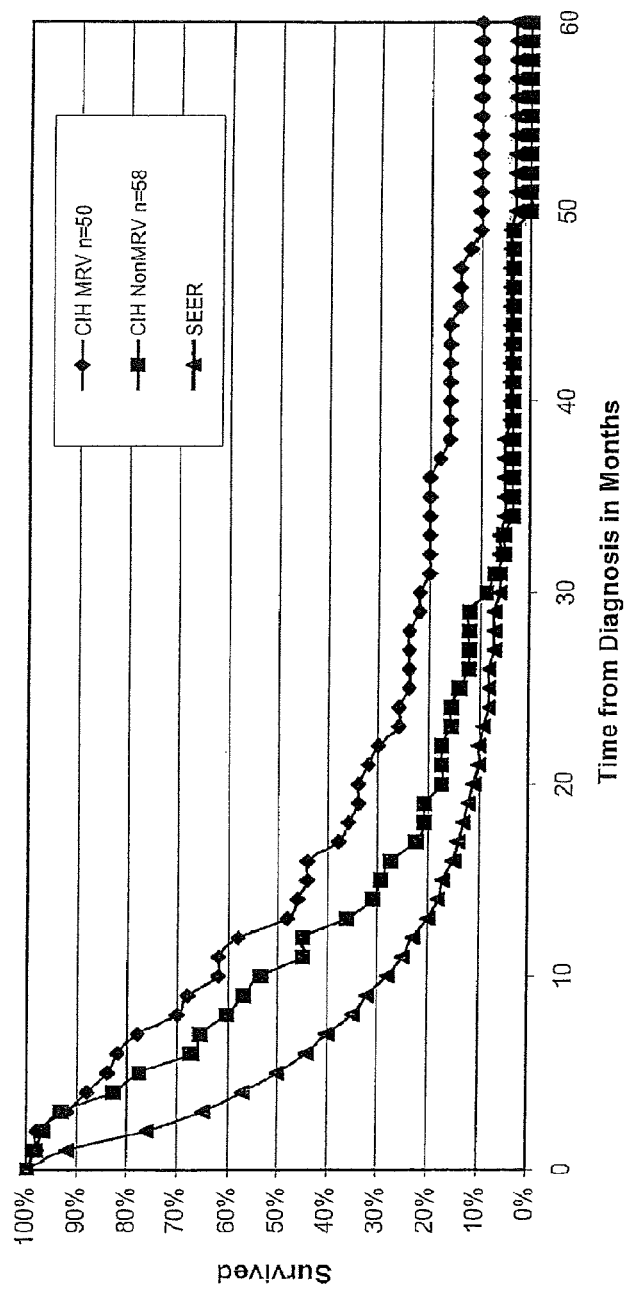
FIG. 1 shows a survival curve for a cumulative series of patients diagnosed with stage 3B or 4 inoperable lung cancer (all patients), comparing patients treated with MRV, patients not treated with the MRV, and a standard SEER survival curve.

In various aspects, the invention relates to the surprising discovery that administration, for example at a site distant from the cancer, of microbial pathogens, such as killed microbial pathogens, that are pathogenic in a particular tissue or organ is effective in treating cancer situated in that specific tissue or organ. Accordingly, the invention provides antigenic compositions derived from these microbial pathogens, including whole killed bacterial or viral species, or components thereof, for the treatment of cancer, and methods for using the same.

Based on observations from treating patients, it was found that administering compositions of killed bacteria which included many of the bacterial species that commonly cause lung infection was surprisingly and unexpectedly effective in improving the clinical course of cancer of the lung. Similarly, it was found that administering compositions including killed *Staphylococcus aureus*, one of the most common causes of bone, breast, skin, perineal and lymph node infection and septicemia was surprising and unexpectedly effective in improving the clinical course of cancer of the bone, breast, skin, perineum, and lymphoma (cancer of the lymph glands) and multiple myeloma (a type of hematological cancer). Similarly, it was surprisingly and unexpectedly found that administering a composition including *Escherichia coli*, which is a common cause of colon, kidney, peritoneal, liver, abdominal, pancreatic and ovarian infection, was effective in improving the clinical course of cancer in the colon, kidney, peritoneum, liver, abdominal lymph nodes, pancreas and ovary.

These results indicate that a composition including antigens of pathogenic microbial species that cause infection in a particular tissue or organ will be an effective formulation for treating a cancer in that tissue or organ. For example, cancer in the lung is effectively treated with a microbial composition including one or more pathogenic species that commonly cause lung infection, while cancer in the colon is effectively treated with a composition including pathogenic microbial species that commonly cause colon infections.

Antigenic compositions of the invention may be produced that include antigenic determinants that together are specific for or characteristic of a microbial pathogen. In this context, by "specific", it is meant that the antigenic determinants are sufficiently characteristic of the pathogen that they could be used to raise an immune response, such as an adaptive immune response, against the pathogen in the patient, if the antigenic determinants were to be administered in an appropriate manner to have that effect. It will be recognized that the antigenic determinants need not be so specific that they are characteristic of only one particular strain or species of pathogen, since even a specific immune response against a particular pathogen may be cross reactive with other closely related organisms that are also naturally pathogenic in the tissue or organ in which the cancer is situated and that the antigenic composition is formulated or selected to target.

In some embodiments, the compositions of pathogenic microbes may be used for treating primary cancer sites and/or sites of metastasis. Thus, for example, the microbial compositions may be used for the treatment of a cancer at a particular site, regardless of whether the cancer is a primary cancer or a metastasis. The composition may be directed to the treatment of each cancer site, or may be a combined composition for both the primary cancer and the metastatic site(s). For example, to treat kidney cancer that has metastasized to the lung and bone, three different compositions, including one or more species that are known to be kidney pathogens, one or more species that are known to be lung pathogens and one or more species that are known to be bone pathogens, or a combined composition thereof may be used. In some embodiments, the compositions may be administered in different locations at the same time or at different times.

For example, for lung cancer with metastasis to the bone, in alternative embodiments, both a microbial composition including one or more bacterial species (or viruses) which commonly cause lung infection and a microbial composition including one or more bacterial species (or viruses) which commonly cause bone infection may be used. Similarly, for colon cancer with metastasis to the lungs, both a pathogenic bacterial (or viral) composition including one or more bacterial species (or viruses) which commonly cause colon infection and a microbial composition including one or more bacterial species (or viruses) which commonly cause lung infection may be used; for prostate cancer with metastasis to the bones, both a pathogenic bacterial (or viral) composition including one or more bacterial species (or viruses) which commonly cause prostate infection and a pathogenic bacterial (or viral) composition including one or more bacterial species (or viruses) that commonly cause bone infection may be used.

The following list provides some non-limiting examples of primary cancers and their common sites for secondary spread (metastases):

| Primary cancer | Common sites for metastases |
|---|---|
| prostate | bone, lungs |
| breast | bone, lungs, skin, liver, brain |
| lung | bone, brain, liver, lungs |
| colon | liver, lungs, bone, brain |
| kidney | lungs, bone, brain |

-continued

| Primary cancer | Common sites for metastases |
| --- | --- |
| pancreas | liver, lungs |
| melanoma | lungs, skin, liver, brain |
| uterus | lungs, bones, ovaries |
| ovary | liver, lung |
| bladder | bone, lung, liver |
| head and neck | bone, lungs |
| sarcoma | lungs, brain |
| stomach | liver |
| cervix | bone, lungs |
| testes | lungs |
| thyroid | bone, lungs |

In some embodiments, the antigenic compositions may be used for treating or preventing cancers at primary sites or for treating or preventing metastasis. For example, in long-term smokers, an antigenic composition specific for cancer of the lung (for example including antigenic determinants of one or more bacterial species or viruses which commonly cause lung infection) may be used to appropriately stimulate the immune system to defend against the development of cancer within the lung tissue. As another example, an antigenic composition specific for cancer of the breast (for example including antigenic determinants of one or more bacterial species which commonly cause breast infection) could be used to prevent breast cancer in women with a strong family history of breast cancer or a genetic predisposition. In alternative embodiments, an antigenic composition including one or more bacterial species which commonly cause bone infection may be used to prevent or treat bone metastases in a patient with prostate cancer. In further alternative embodiments, an antigenic composition including one or more bacterial species or viruses which commonly cause lung infection may be used to prevent or treat lung metastases in a patient with malignant melanoma.

Various alternative embodiments and examples of the invention are described herein. These embodiments and examples are illustrative and should not be construed as limiting the scope of the invention.

Cancers

Most cancers fall within three broad histological classifications: carcinomas, which are the predominant cancers and are cancers of epithelial cells or cells covering the external or internal surfaces of organs, glands, or other body structures (e.g., skin, uterus, lung, breast, prostate, stomach, bowel), and which tend to metastasize; sarcomas, which are derived from connective or supportive tissue (e.g., bone, cartilage, tendons, ligaments, fat, muscle); and hematologic tumors, which are derived from bone marrow and lymphatic tissue. Carcinomas may be adenocarcinomas (which generally develop in organs or glands capable of secretion, such as breast, lung, colon, prostate or bladder) or may be squamous cell carcinomas (which originate in the squamous epithelium and generally develop in most areas of the body). Sarcomas may be osteosarcomas or osteogenic sarcomas (bone), chondrosarcomas (cartilage), leiomyosarcomas (smooth muscle), rhabdomyosarcomas (skeletal muscle), mesothelial sarcomas or mesotheliomas (membranous lining of body cavities), fibrosarcomas (fibrous tissue), angiosarcomas or hemangioendotheliomas (blood vessels), liposarcomas (adipose tissue), gliomas or astrocytomas (neurogenic connective tissue found in the brain), myxosarcomas (primitive embryonic connective tissue), or mesenchymous or mixed mesodermal tumors (mixed connective tissue types). Hematologic tumors may be myelomas, which originate in the plasma cells of bone marrow; leukemias which may be "liquid cancers" and are cancers of the bone marrow and may be myelogenous or granulocytic leukemia (myeloid and granulocytic white blood cells), lymphatic, lymphocytic, or lymphoblastic leukemias (lymphoid and lymphocytic blood cells) or polycythemia vera or erythremia (various blood cell products, but with red cells predominating); or lymphomas, which may be solid tumors and which develop in the glands or nodes of the lymphatic system, and which may be Hodgkin or Non-Hodgkin lymphomas. In addition, mixed type cancers, such as adenosquamous carcinomas, mixed mesodermal tumors, carcinosarcomas, or teratocarcinomas also exist.

Cancers may also be named based on the organ in which they originate i.e., the "primary site," for example, cancer of the breast, brain, lung, liver, skin, prostate, testicle, bladder, colon and rectum, cervix, uterus, etc. This naming persists even if the cancer metastasizes to another part of the body that is different from the primary site. With the present invention, treatment is directed to the site of the cancer, not type of cancer, so that a cancer of any type that is situated in the lung, for example, would be treated on the basis of this localization in the lung.

Cancers named based on primary site may be correlated with histological classifications. For example, lung cancers are generally small cell lung cancers or non-small cell lung cancers, which may be squamous cell carcinoma, adenocarcinoma, or large cell carcinoma; skin cancers are generally basal cell cancers, squamous cell cancers, or melanomas. Lymphomas may arise in the lymph nodes associated with the head, neck and chest, as well as in the abdominal lymph nodes or in the axillary or inguinal lymph nodes. Identification and classification of types and stages of cancers may be performed by using for example information provided by the Surveillance, Epidemiology, and End Results (SEER) Program of the National Cancer Institute, which is an authoritative source of information on cancer incidence and survival in the United States and is recognized around the world. The SEER Program currently collects and publishes cancer incidence and survival data from 14 population-based cancer registries and three supplemental registries covering approximately 26 percent of the US population. The program routinely collects data on patient demographics, primary tumor site, morphology, stage at diagnosis, first course of treatment, and follow-up for vital status, and is the only comprehensive source of population-based information in the United States that includes stage of cancer at the time of diagnosis and survival rates within each stage. Information on more than 3 million in situ and invasive cancer cases is included in the SEER database, and approximately 170,000 new cases are added each year within the SEER coverage areas. The incidence and survival data of the SEER Program may be used to access standard survival for a particular cancer site and stage. For example, to ensure an optimal comparison group, specific criteria may be selected from the database, including date of diagnosis and exact stage (for example, in the case of the lung cancer example herein, the years were selected to match the time-frame of the retrospective review, and stage 3B and 4 lung cancer were selected; and in the case of the colon cancer example herein, the years were also selected to match the time-frame of the retrospective review, and the stage 4 colon cancer was selected).

Bacteria and Bacterial Colonizations and Infections

Most animals are colonized to some degree by other organisms, such as bacteria, which generally exist in symbiotic or commensal relationships with the host animal. Thus, many species of normally harmless bacteria are found in healthy animals, and are usually localized to the surface of specific organs and tissues. Often, these bacteria aid in the normal functioning of the body. For example, in humans, symbiotic *Escherichia coli* bacteria may be found in the intestine, where they promote immunity and reduce the risk of infection with more virulent pathogens.

Bacteria that are generally harmless, such as *Escherichia coli*, can cause infection in healthy subjects, with results ranging from mild to severe infection to death. Whether or not a bacterium is pathogenic (i.e., causes infection) depends to some extent on factors such as the route of entry and access to specific host cells, tissues, or organs; the intrinsic virulence of the bacterium; the amount of the bacteria present at the site of potential infection; or the health of the host animal. Thus, bacteria that are normally harmless can become pathogenic given favorable conditions for infection, and even the most virulent bacterium requires specific circumstances to cause infection. Accordingly, microbial species that are members of the normal flora can be pathogens when they move beyond their normal ecological role in the endogenous flora. For example, endogenous species can cause infection outside of their ecological niche in regions of anatomical proximity, for example by contiguous spread. When this occurs, these normally harmless endogenous bacteria are considered pathogenic.

Specific bacterial species and viruses are known to cause infections in specific cells, tissues, or organs in otherwise healthy subjects. Examples of bacteria and viruses that commonly cause infections in specific organs and tissues of the body are listed below; it will be understood that these examples are not intended to be limiting and that a skilled person would be able to readily recognize and identify infectious or pathogenic bacteria that cause infections, or commonly cause infections, in various organs and tissues in healthy adults (and recognize the relative frequency of infection with each bacterial species) based on the knowledge in the field as represented, for example, by the following publications: Manual of Clinical Microbiology 8th Edition, Patrick Murray, Ed., 2003, ASM Press American Society for Microbiology, Washington D.C., USA; Mandell, Douglas, and Bennett's Principles and Practice of Infectious Diseases 5th Edition, G. L. Mandell, J. E. Bennett, R. Dolin, Eds., 2000, Churchill Livingstone, Philadelphia, Pa., USA, all of which are incorporated by reference herein.

Infections of the skin are commonly caused by the following bacterial species: *Staphylococcus aureus*, Beta hemolytic streptococci group A, B, C or G, *Corynebacterium diptheriae, Corynebacterium ulcerans*, or *Pseudomonas aeruginosa*; or viral pathogens: rubeola, rubella, varicella-zoster, echoviruses, coxsackieviruses, adenovirus, vaccinia, herpes simplex, or parvo B19.

Infections of the soft tissue (e.g., fat and muscle) are commonly caused by the following bacterial species: *Streptococcus pyogenes, Staphylococcus aureus, Clostridium perfringens*, or other *Clostridium* spp.; or viral pathogens: influenza, or coxsackieviruses Infections of the breast are commonly caused by the following bacterial species: *Staphylococcus aureus*, or *Streptococcus pyogenes*.

Infections of the lymph nodes of the head and neck are commonly caused by the following bacterial species: *Staphylococcus aureus*, or *Streptococcus pyogenes*; or viral pathogens: Epstein-Barr, cytomegalovirus, adenovirus, measles, rubella, herpes simplex, coxsackieviruses, or varicella-zoster.

Infections of the lymph nodes of the arm/axillae are commonly caused by the following bacterial species: *Staphylococcus aureus*, or *Streptococcus pyogenes*; or viral pathogens: measles, rubella, Epstein-Barr, cytomegalovirus, adenovirus, or varicella-zoster.

Infections of the lymph nodes of the mediastinum are commonly caused by the following bacterial species: viridans streptococci, *Peptococcus* spp., *Peptostreptococcus* spp., *Bacteroides* spp., *Fusobacterium* spp., or *Mycobacterium tuberculosis*; or viral pathogens: measles, rubella, Epstein-Barr, cytomegalovirus, varicella-zoster, or adenovirus.

Infections of the pulmonary hilar lymph nodes are commonly caused by the following bacterial species: *Streptococcus pneumoniae, Moraxella catarrhalis, Mycoplasma pneumoniae, Klebsiella pneumoniae, Haemophilus influenza, Chlamydophila pneumoniae, Bordetella pertussis* or *Mycobacterium tuberculosis*; or viral pathogens: influenza, adenovirus, rhinovirus, coronavirus, parainfluenza, respiratory syncytial virus, human metapneumovirus, or coxsackievirus.

Infections of the intra-abdominal lymph nodes are commonly caused by the following bacterial species: *Yersinia enterocolitica, Yersinia pseudotuberculosis, Salmonella* spp., *Streptococcus pyogenes, Escherichia coli, Staphylococcus aureus*, or *Mycobacterium tuberculosis*; or viral pathogens: measles, rubella, Epstein-Barr, cytomegalovirus, varicella-zoster, adenovirus, influenza, or coxsackievi ruses.

Infections of the lymph nodes of the leg/inguinal region are commonly caused by the following bacterial species: *Staphylococcus aureus*, or *Streptococcus pyogenes*; or viral pathogens: measles, rubella, Epstein-Barr, cytomegalovirus, or herpes simplex.

Infections of the blood (i.e., septicemia) are commonly caused by the following bacterial species: *Staphylococcus aureus, Streptococcus pyogenes*, coagulase-negative staphylococci, *Enterococcus* spp., *Escherichia coli, Klebsiella* spp., *Enterobacter* spp., *Proteus* spp., *Pseudomonas aeruginosa, Bacteroides fragilis, Streptococcus pneumoniae*, or group B streptococci; or viral pathogens: rubeola, rubella, varicella-zoster, echoviruses, coxsackieviruses, adenovirus, Epstein-Barr, herpes simplex, or cytomegalovirus.

Infections of the bone are commonly caused by the following bacterial species: *Staphylococcus aureus*, coagulase-negative staphylococci, *Streptococcus pyogenes, Streptococcus pneumoniae, Streptococcus agalactiae*, other streptococci spp., *Escherichia coli, Pseudomonas* spp., *Enterobacter* spp., *Proteus* spp., or *Serratia* spp.; or viral pathogens: parvovirus B19, rubella, or hepatitis B.

Infections of the meninges are commonly caused by the following bacterial species: *Haemophilus influenzae, Neisseria meningitidis, Streptococcus pneumoniae, Streptococcus agalactiae*, or *Listeria monocytogenes*; or viral pathogens: echoviruses, coxsackieviruses, other enteroviruses, or mumps.

Infections of the brain are commonly caused by the following bacterial species: *Streptococcus* spp. (including *S. anginosus, S. constellatus, S. intermedius*), *Staphylococcus aureus, Bacteroides* spp., *Prevotella* spp., *Proteus* spp., *Escherichia coli, Klebsiella* spp., *Pseudomonas* spp., *Enterobacter* spp., or *Borrelia burgdorferi*; or viral pathogens: coxsackieviruses, echoviruses, poliovirus, other enteroviruses, mumps, herpes simplex, varicella-zoster, flaviviruses, or bunyaviruses.

Infections of the spinal cord are commonly caused by the following bacterial species: *Haemophilus influenzae, Neisseria meningitidis, Streptococcus pneumoniae, Streptococcus agalactiae, Listeria monocytogenes*, or *Borrelia burgdorferi*; or viral pathogens: coxsackieviruses, echoviruses, poliovirus, other enteroviruses, mumps, herpes simplex, varicella-zoster, flaviviruses, or bunyaviruses.

Infections of the eye/orbit are commonly caused by the following bacterial species: *Staphylococcus aureus, Streptococcus pyogenes, Streptococcus pneumoniae, Streptococcus* milleri, *Escherichia coli, Bacillus cereus, Chlamydia trachomatis, Haemophilus influenza, Pseudomonas* spp., *Klebsiella* spp., or *Treponema pallidum*; or viral pathogens: adenoviruses, herpes simplex, varicella-zoster, or cytomegalovirus.

Infections of the salivary glands are commonly caused by the following bacterial species: *Staphylococcus aureus*, viridans streptococci (e.g., *Streptococcus salivarius, Streptococcus sanguis, Streptococcus mutans*), *Peptostreptococcus* spp., or *Bacteroides* spp., or other oral anaerobes; or viral pathogens: mumps, influenza, enteroviruses, or rabies.

Infections of the mouth are commonly caused by the following bacterial species: *Prevotella melaminogenicus*, anaerobic streptococci, viridans streptococci, *Actinomyces* spp., *Peptostreptococcus* spp., or *Bacteroides* spp., or other oral anaerobes; or viral pathogens: herpes simplex, coxsackieviruses, or Epstein-Barr.

Infections of the tonsils are commonly caused by the following bacterial species: *Streptococcus pyogenes*, or Group C or G B-hemolytic streptococci; or viral pathogens: rhinoviruses, influenza, coronavirus, adenovirus, parainfluenza, respiratory syncytial virus, or herpes simplex.

Infections of the sinuses are commonly caused by the following bacterial species: *Streptococcus pneumoniae, Haemophilus influenza, Moraxella catarrhalis*, α-streptococci, anaerobic bacteria (e.g., *Prevotella* spp.), or *Staphylococcus aureus*; or viral pathogens: rhinoviruses, influenza, adenovirus, or parainfluenza.

Infections of the nasopharynx are commonly caused by the following bacterial species: *Streptococcus pyogenes*, or Group C or G B-hemolytic streptococci; or viral pathogens: rhinoviruses, influenza, coronavirus, adenovirus, parainfluenza, respiratory syncytial virus, or herpes simplex.

Infections of the thyroid are commonly caused by the following bacterial species: *Staphylococcus aureus, Streptococcus pyogenes*, or *Streptococcus pneumoniae*; or viral pathogens: mumps, or influenza.

Infections of the larynx are commonly caused by the following bacterial species: *Mycoplasma pneumoniae, Chlamydophila pneumoniae*, or *Streptococcus pyogenes*; or viral pathogens: rhinovirus, influenza, parainfluenza, adenovirus, corona virus, or human metapneumovirus.

Infections of the trachea are commonly caused by the following bacterial species: *Mycoplasma pneumoniae*; or viral pathogens: parainfluenza, influenza, respiratory syncytial virus, or adenovirus.

Infections of the bronchi are commonly caused by the following bacterial species: *Mycoplasma pneumoniae, Chlamydophila pneumoniae, Bordetella pertussis, Streptococcus pneumoniae*, or *Haemophilus influenzae*; or viral pathogens: influenza, adenovirus, rhinovirus, coronavirus, parainfluenza, respiratory syncytial virus, human metapneumovirus, or coxsackievirus.

Infections of the lung are commonly caused by the following bacterial species: *Streptococcus pneumoniae, Moraxella catarrhalis, Mycoplasma pneumoniae, Klebsiella pneumoniae*, or *Haemophilus influenza*; or viral pathogens: influenza, adenovirus, respiratory syncytial virus, or parainfluenza.

Infections of the pleura are commonly caused by the following bacterial species: *Staphylococcus aureus, Streptococcus pyogenes, Streptococcus pneumoniae, Haemophilus influenzae, Bacteroides fragilis, Prevotella* spp., *Fusobacterium nucleatum, peptostreptococcus* spp., or *Mycobacterium tuberculosis*; or viral pathogens: influenza, adenovirus, respiratory syncytial virus, or parainfluenza.

Infections of the mediastinum are commonly caused by the following bacterial species: viridans streptococci, *Peptococcus* spp., *Peptostreptococcus* spp., *Bacteroides* spp., *Fusobacterium* spp., or *Mycobacterium tuberculosis*; or viral pathogens: measles, rubella, Epstein-Barr, or cytomegalovirus.

Infections of the heart are commonly caused by the following bacterial species: *Streptococcus* spp. (including *S. mitior, S. bovis, S. sanguis, S. mutans, S. anginosus*), *Enterococcus* spp., *Staphylococcus* spp., *Corynebacterium diptheriae, Clostridium perfringens, Neisseria meningitidis*, or *Salmonella* spp.; or viral pathogens: enteroviruses, coxsackieviruses, echoviruses, poliovirus, adenovirus, mumps, rubeola, or influenza.

Infections of the esophagus are commonly caused by the following bacterial species: *Actinomyces* spp., *Mycobacterium avium, Mycobacterium tuberculosis*, or *Streptococcus* spp.; or viral pathogens: cytomegalovirus, herpes simplex, or varicella-zoster.

Infections of the stomach are commonly caused by the following bacterial species: *Streptococcus pyogenes* or *Helicobacter pylori*; or viral pathogens: cytomegalovirus, herpes simplex, Epstein-Barr, rotaviruses, noroviruses, or adenoviruses.

Infections of the small bowel are commonly caused by the following bacterial species: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica*, or *Shigella flexneri*; or viral pathogens: adenoviruses, astroviruses, caliciviruses, noroviruses, rotaviruses, or cytomegalovirus.

Infections of the colon/rectum are commonly caused by the following bacterial species: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica*, or *Shigella flexneri*; or viral pathogens: adenoviruses, astroviruses, caliciviruses, noroviruses, rotaviruses, or cytomegalovirus.

Infections of the anus are commonly caused by the following bacterial species: *Streptococcus pyogenes, Bacteroides* spp., *Fusobacterium* spp., anaerobic streptococci, *Clostridium* spp., *Escherichia coli, Enterobacter* spp., *Pseudomonas aeruginosa*, or *Treponema pallidum*; or viral pathogens: herpes simplex.

Infections of the perineum are commonly caused by the following bacterial species: *Escherichia coli, Klebsiella* spp., *Enterococcus* spp., *Bacteroides* spp., *Fusobacterium* spp., *Clostridium* spp., *Pseudomonas aeruginosa*, anaerobic streptococci, *Clostridium* spp., or *Enterobacter* spp.; or viral pathogens: herpes simplex.

Infections of the liver are commonly caused by the following bacterial species: *Escherichia coli, Klebsiella* spp., *Streptococcus* (anginosus group), *Enterococcus*, spp. other viridans streptococci, or *Bacteroides* spp.; or viral pathogens: hepatitis A, Epstein-Barr, herpes simplex, mumps, rubella, rubeola, varicella-zoster, coxsackieviruses, or adenovirus.

Infections of the gallbladder are commonly caused by the following bacterial species: *Escherichia coli, Klebsiella* spp., *Enterobacter* spp., enterococci, *Bacteroides* spp., *Fusobacterium* spp., *Clostridium* spp., *Salmonella enteriditis, Yersinia enterocolitica*, or *Shigella flexneri*.

Infections of the biliary tract are commonly caused by the following bacterial species: *Escherichia coli, Klebsiella* spp., *Enterobacter* spp., enterococci, *Bacteroides* spp., *Fusobacterium* spp., *Clostridium* spp., *Salmonella enteriditis, Yersinia enterocolitica*, or *Shigella flexneri*; or viral pathogens: hepatitis A, Epstein-Barr, herpes simplex, mumps, rubella, rubeola, varicella-zoster, cocsackieviruses, or adenovirus.

Infections of the pancreas are commonly caused by the following bacterial species: *Escherichia coli, Klebsiella* spp., *Enterococcus* spp., *Pseudomonas* spp., *Staphylococcal* spp., *Mycoplasma* spp., *Salmonella typhi, Leptospirosis* spp., or *Legionella* spp.; or viral pathogens: mumps, coxsackievirus, hepatitis B, cytomegalovirus, herpes simplex 2, or varicella-zoster.

Infections of the spleen are commonly caused by the following bacterial species: *Streptococcus* spp., *Staphylococcus* spp., *Salmonella* spp., *Pseudomonas* spp., *Escherichia coli*, or *Enterococcus* spp.; or viral pathogens: Epstein-Barr, cytomegalovirus, adenovirus, measles, rubella, coxsackieviruses, or varicella-zoster.

Infections of the adrenal gland are commonly caused by the following bacterial species: *Streptococcus* spp., *Staphylococcus* spp., *Salmonella* spp., *Pseudomonas* spp., *Escherichia coli*, or *Enterococcus* spp.; or viral pathogens: varicella-zoster.

Infections of the kidney are commonly caused by the following bacterial species: *Escherichia coli, Proteus mirabilis, Proteus vulgatus, Providentia* spp., *Morganella* spp., *Enterococcus faecalis*, or *Pseudomonas aeruginosa*; or viral pathogens: BK virus, or mumps.

Infections of the ureter are commonly caused by the following bacterial species: *Escherichia coli, Proteus mirabilis, Proteus vulgatus, Providentia* spp., *Morganella* spp., or *Enterococcus* spp.

Infections of the bladder are commonly caused by the following bacterial species: *Escherichia coli, Proteus mirabilis, Proteus vulgatus, Providentia* spp., *Morganella* spp., *Enterococcus faecalis*, or *Corynebacterium jekeum*; or viral pathogens: adenovirus, or cytomegalovirus.

Infections of the peritoneum are commonly caused by the following bacterial species: *Staphylococcus aureus, Streptococcus pyogenes, Streptococcus pneumonia, Escherichia coli, Klebsiella* spp., *Proteus* spp., enterococci, *Bacteroides fragilis, Prevotella melaminogenica, Peptococcus* spp., *Peptostreptococcus* spp., *Fusobacterium* spp., or *Clostridium* spp.

Infections of the retroperitoneal area are commonly caused by the following bacterial species: *Escherichia coli*, or *Staphylococcus aureus*.

Infections of the prostate are commonly caused by the following bacterial species: *Escherichia coli, Klebsiella* spp., *Enterobacter* spp., *Proteus mirabilis*, enterococci spp., *Pseudomonas* spp., *Corynebacterium* spp., or *Neisseria gonorrhoeae*; or viral pathogens: herpes simplex.

Infections of the testicle are commonly caused by the following bacterial species: *Escherichia coli, Klebsiella pneumoniae, Pseudomonas aeruginosa, Staphylococcus* spp., *Streptococcus* spp., or *Salmonella enteriditis*; or viral pathogens: mumps, coxsackievirus, or lymphocytic choriomeningitis virus.

Infections of the penis are commonly caused by the following bacterial species: *Staphylococcus aureus, Streptococcus pyogenes, Neisseria gonorrhoeae*, or *Treponema pallidum*; or viral pathogens: herpes simplex.

Infections of the ovary/adnexae are commonly caused by the following bacterial species: *Neisseria gonorrhoeae, Chlamydia trachomatis, Gardenerella vaginalis, Prevotella* spp., *Bacteroides* spp., *Peptococcus* spp. *Streptococcus* spp., or *Escherichia coli*.

Infections of the uterus are commonly caused by the following bacterial species: *Neisseria gonorrhoeae, Chlamydia trachomatis, Gardenerella vaginalis, Prevotella* spp., *Bacteroides* spp., *Peptococcus* spp., *Streptococcus* spp., or *Escherichia coli*.

Infections of the cervix are commonly caused by the following bacterial species: *Neisseria gonorrhoeae, Chlamydia trachomatis*, or *Treponema pallidum*; or viral pathogens: herpes simplex.

Infections of the vagina are commonly caused by the following bacterial species: *Gardenerella vaginalis, Prevotella* spp., *Bacteroides* spp., peptococci spp., *Escherichia coli, Neisseria gonorrhoeae, Chlamydia Trachomatis*, or *Treponema pallidum*; or viral pathogens: herpes simplex.

Infections of the vulva are commonly caused by the following bacterial species: *Staphylococcus aureus, Streptococcus pyogenes*, or *Treponema pallidum*; or viral pathogens: herpes simplex.

Bacterial Strains/Viral Subtypes

It will be understood by a skilled person that bacterial species are classified operationally as collections of similar strains (which generally refers to groups of presumed common ancestry with identifiable physiological but usually not morphological distinctions, and which may be identified using serological techniques against bacterial surface antigens). Thus, each bacterial species (e.g., *Streptococcus pneumoniae*) has numerous strains (or serotypes), which may differ in their ability to cause infection or differ in their ability to cause infection in a particular organ/site. For example, although there are at least 90 serotypes of *Streptococcus pneumoniae*, serotypes 1, 3, 4, 7, 8, and 12 are most frequently responsible for pneumococcal disease in humans.

As a second example, certain strains of *Escherichia coli*, referred to as extraintestinal pathogenic *E. coli* (ExPEC), are more likely to cause urinary tract infection or other extraintestinal infections such as neonatal meningitis, whereas other strains, including enterotoxigenic *E. coli* (ETEC), enteropathogenic *E. coli* (EPEC), enterohemorrhagic *E. coli* (EHEC), Shiga toxin-producing *E. coli* (STEC), enteroaggregative *E. coli* (EAEC), enteroinvasive *E. coli* (EIEC) and diffuse adhering *E. coli* (DAEC) are more likely to cause gastrointestinal infection/diarrhea. Even among the sub-category of ExPEC strains, specific virulence factors (e.g., production of type-1 fimbriae) enable certain strains to be more capable of causing infection of the bladder, while other virulence factors (e.g., production of P fimbriae) enable other strains to be more capable of causing infection in the kidneys. In accordance with the present invention, an ExPEC strain(s) that is more likely to cause infection in the bladder may be chosen for a formulation to target bladder cancer, whereas an ExPEC strain(s) that is more likely to cause infection in the kidney may be chosen for a formulation to target kidney cancer. Likewise, one or more of an ETEC, EPEC, EHEC, STEC, EAEC, EIEC or DAEC strains of *E. coli* (i.e., strains that cause colon infection), may be chosen for a formulation to treat colon cancer.

Similarly, there may be numerous subtypes of specific viruses. For example, there are three types of influenza viruses, influenza A, influenza B and influenza C, which differ in epidemiology, host range and clinical characteristics. For example, influenza A is more likely to be associated with viral lung infection, whereas influenza B is more likely to be associated with myositis (i.e., muscle infection). Furthermore, each of these three types of influenza virus have numerous subtypes, which also may differ in epidemiology, host range and clinical characteristics. In accordance with the present invention, one may choose an influenza A subtype most commonly associated with lung infection to target lung cancer, whereas one may choose an influenza B strain most commonly associated with myositis to treat cancer of the muscle/soft tissues.

It is understood that a clinical microbiologist skilled in the art would therefore be able to select, based on the present disclosure and the body of art relating to bacterial strains for each species of bacteria (and viral subtypes for each type of virus), the strains of a particular bacterial species (or subtype of a particular virus) to target a specific organ or tissue.

Bacterial Compositions, Dosages, and Administration

The compositions of the invention include antigens of pathogenic microbial (bacterial or viral) species that are pathogenic in a specific tissue or organ. The compositions may include whole bacterial species, or may include extracts or preparations of the pathogenic bacterial species of the invention, such as cell wall or cell membrane extracts, or whole cells, or exotoxins, or whole cells and exotoxins. The compositions may also include one or more isolated antigens from one or more of the pathogenic bacterial species of the invention; in some embodiments, such compositions may be useful in situations where it may be necessary to precisely administer a specific dose of a particular antigen, or may be useful if administering a whole bacterial species or components thereof (e.g., toxins) may be harmful. Pathogenic bacterial species may be available commercially (from, for example, ATCC (Manassas, Va., USA), or may be clinical isolates from subjects having a bacterial infection of a tissue or organ (e.g., pneumonia).

The microbial compositions of the invention can be provided alone or in combination with other compounds (for example, nucleic acid molecules, small molecules, peptides, or peptide analogues), in the presence of a liposome, an adjuvant, or any pharmaceutically acceptable carrier, in a form suitable for administration to mammals, for example, humans. As used herein "pharmaceutically acceptable carrier" or "excipient" includes any and all solvents, dispersion media, coatings, antibacterial and antifungal agents, isotonic and absorption delaying agents, and the like that are physiologically compatible. The carrier can be suitable for any appropriate form of administration, including subcutaneous, intradermal, intravenous, parenteral, intraperitoneal, intramuscular, sublingual, inhalational, intratumoral or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound (i.e., the specific bacteria, bacterial antigens, or compositions thereof of the invention), use thereof in the pharmaceutical compositions of the invention is contemplated. Supplementary active compounds can also be incorporated into the compositions.

If desired, treatment with bacterial antigens according to the invention may be combined with more traditional and existing therapies for cancer, such as chemotherapy, radiation therapy, surgery, etc., or with any other therapy intended to stimulate the immune system, reduce inflammation or otherwise benefit the subject, such as nutrients, vitamins and supplements. For example, vitamin A, vitamin D, vitamin E, vitamin C, vitamin B complex, selenium, zinc, co-enzyme Q10, beta carotene, fish oil, curcumin, green tea, bromelain, resveratrol, ground flaxseed, garlic, lycopene, milk thistle, melatonin, other antioxidants, cimetidine, indomethacin, or COX-2 Inhibitors (e.g., Celebrex™ [celecoxib] or Vioxx™ [rofecoxib]) may be also be administered to the subject.

Conventional pharmaceutical practice may be employed to provide suitable formulations or compositions to administer the compounds to subjects suffering from a cancer. Any appropriate route of administration may be employed, for example, parenteral, intravenous, intradermal, subcutaneous, intramuscular, intracranial, intraorbital, ophthalmic, intraventricular, intracapsular, intraspinal, intrathecal, intracisternal, intraperitoneal, intranasal, inhalational, aerosol, topical, intratumoral, sublingual or oral administration. Therapeutic formulations may be in the form of liquid solutions or suspensions; for oral administration, formulations may be in the form of tablets or capsules; for intranasal formulations, in the form of powders, nasal drops, or aerosols; and for sublingual formulations, in the form of drops, aerosols or tablets.

Methods well known in the art for making formulations are found in, for example, "Remington's Pharmaceutical Sciences" (20th edition), ed. A. Gennaro, 2000, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the pathogenic bacterial species are administered to an individual in an amount effective to stop or slow progression or metastasis of the cancer, or to increase survival of the subject (relative to for example prognoses derived from the SEER database) depending on the disorder.

An "effective amount" of a pathogenic microbial species or antigen thereof according to the invention includes a therapeutically effective amount or a prophylactically effective amount. A "therapeutically effective amount" refers to an amount effective, at dosages and for periods of time necessary, to achieve the desired therapeutic result, such as reduction or elimination of the cancer cells or tumors, prevention of carcinogenic processes, slowing the growth of the tumour, or an increase in survival time beyond that which is expected using for example the SEER database. A therapeutically effective amount of a pathogenic microbial (bacterial or viral) species or antigen(s) thereof may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the pathogenic bacterial species or virus or antigen thereof are outweighed by the therapeutically beneficial effects. A "prophylactically effective amount" refers to an amount effective, at dosages and for periods of time necessary, to achieve the desired prophylactic result, such as prevention of cancer, prevention of metastasis, slowing the growth of the tumour, reduction or elimination of the cancer cells, tissues, organs, or tumors, or an increase in survival time beyond that which is expected using for example the SEER database. Typically, a prophylactic dose is used in subjects prior to or at an earlier stage of cancer, so that a prophylactically effective amount may be less than a therapeutically effective amount.

For administration by subcutaneous or intradermal injection, an exemplary range for therapeutically or prophylactically effective amounts of one or more pathogenic bacterial species may be about 1 million to 100,000 million organisms per ml, or may be 100 million to 7000 million organisms per ml, or may be 500 million to 6000 million organisms per ml, or may be 1000 million to 5000 million organisms per ml, or may be 2000 million to 4000 million organisms per ml, or any integer within these ranges. The total concentration of bacteria per ml may range from 1 million to 100,000 million organisms per ml, or may be 50 million to 7000 million organisms per ml, or may be 100 million to 6000 million organisms per ml, or may be 500 million to 5000 million organisms per ml, or may be 1000 million to 4000 million organisms per ml, or any integer within these ranges. The range for therapeutically or prophylactically effective amounts of antigens of a pathogenic bacterial species may be any integer from 0.1 nM-0.1M, 0.1 nM-0.05M, 0.05 nM-15 µM or 0.01 nM-10 µM.

It is to be noted that dosage concentrations and ranges may vary with the severity of the condition to be alleviated, or may vary with the subject's immune response. In general, the goal is to achieve an adequate immune response. For administration by subcutaneous or intradermal infection, the extent of an immune response may be determined, for example, by size of delayed local immune skin reaction at the site of injection (e.g., from 0.25 inch to 4 inch diameter). The dose required to achieve an appropriate immune response may vary depending on the individual (and their immune system) and the response desired. Standardized dosages may also be used. In the context of subcutaneous or intradermal administration, if the goal is to achieve a 2 inch local skin reaction, the total bacterial composition dose may, for example, range from 2 million bacteria (e.g., 0.001 ml of a vaccine with a concentration of 2,000 million organisms per ml) to more than 20,000 million bacteria (e.g., 1 ml of a vaccine with a concentration of 20,000 million organisms per ml). The concentrations of individual bacterial species or antigens thereof within a composition may also be considered. For example, if the concentration of one particular pathogenic bacterial species, cell size of that species or antigenic load thereof is much higher relative to the other pathogenic bacterial species in the vaccine, then the local immune skin reaction of an individual may be likely due to its response to this specific bacterial species. In some embodiments, the immune system of an individual may respond more strongly to one bacterial species within a composition than another, depending for example on past history of exposure to infection by a particular species, so the dosage or composition may be adjusted accordingly for that individual.

For any particular subject, the timing and dose of treatments may be adjusted over time (e.g., timing may be daily, every other day, weekly, monthly) according to the individual need and the professional judgement of the person administering or supervising the administration of the compositions. For example, in the context of subcutaneous or intradermal administration, the compositions may be administered every second day. An initial dose of approximately 0.05 ml may be administered subcutaneously, followed by increases from 0.01-0.02 ml every second day until an adequate skin reaction is achieved at the injection site (for example, a 1 inch to 2 inch diameter delayed reaction of visible redness at the injection site). Once this adequate immune reaction is achieved, this dosing is continued as a maintenance dose. The maintenance dose may be adjusted from time to time to achieve the desired visible skin reaction (inflammation) at the injection site. Dosing may be for a dosage duration, for example of at least 2 weeks, 2 months, 6 months, 1, 2, 3, 4, or 5 years or longer.

Oral dosages may for example range from 10 million to 1,000,000 million organisms per dose, comprising antigenic determinants of one or more species. Oral dosages may be given, for example, from 4 times per day, daily or weekly. Dosing may be for a dosage duration, for example of at least 2 weeks, 2 months, 6 months, 1, 2, 3, 4, or 5 years or longer.

In some embodiments, the invention may include antigenic compositions administered sublingually or by inhalation, or administered to one or more epithelial tissues (i.e., skin by intradermal or subcutaneous injection; lung epithelium by inhalation; gastrointestinal mucosa by oral ingestion; mouth mucosa by sublingual administration) simultaneously or sequentially. Accordingly, in some embodiments the antigenic compositions of the invention are administered so as to provoke an immune response in an epithelial tissue. In some embodiments, one or more epithelial routes of administration may be combined with one or more additional routes of administration, such as intratumoral, intramuscular or intravenous administration.

In various aspects of the invention, the antigenic compositions that are administered to a patient may be characterized as having an antigenic signature, i.e., a combination of antigens or epitopes, that is sufficiently specific that the antigenic composition is capable of eliciting an immune response that is specific to a particular pathogen, such as an adaptive immune response. A surprising and unexpected aspect of the invention is that the non-adaptive or non-specific activation of the immune response that is mediated by these specific antigenic compositions is effective to treat cancers situated in the tissues in which the particular pathogen is pathogenic.

Routes of administration and dosage ranges set forth herein are exemplary only and do not limit the route of administration and dosage ranges that may be selected by medical practitioners. The amount of active compound (e.g., pathogenic bacterial species or viruses or antigens thereof) in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In the case of antigenic formulations (analogous to a vaccine), an immunogenically effective amount of a compound of the invention can be provided, alone or in combination with other compounds, with an immunological adjuvant. The compound may also be linked with a carrier molecule, such as bovine serum albumin or keyhole limpet hemocyanin to enhance immunogenicity. An antigenic composition ("vaccine") is a composition that includes materials that elicit a desired immune response. An antigenic composition may select, activate or expand memory B, T cells, neutrophils, monocytes or macrophages of the immune system to, for example, reduce or eliminate the growth or proliferation of cancerous cells or tissue. In some embodiments, the specific pathogenic microbe, virus, viral antigens, bacteria, bacterial antigens, or compositions thereof of the invention are capable of eliciting the desired immune response in the absence of any other agent, and may therefore be considered to be an antigenic composition. In some embodiments, an antigenic composition includes a suitable carrier, such as an adjuvant, which is an agent that acts in a non-specific manner to increase the immune response to a specific antigen, or to a group of antigens, enabling the reduction of the quantity of antigen in any given vaccine dose, or the reduction of the frequency of dosage required to generate the desired immune response. A bacterial antigenic composition may include live or dead bacteria capable of inducing an immune response against antigenic determinants normally associated with the bacteria. In some embodiments, an antigenic composition may include live bacteria that are of less virulent strains (attenuated), and therefore cause a less severe infection. In some embodiments the antigenic composition may include live, attenuated or dead viruses capable of inducing an immune response against antigenic determinants normally associated with the virus.

An antigenic composition comprising killed bacteria for administration by injection may be made as follows. The bacteria may be grown in suitable media, and washed with physiological salt solution. The bacteria may then be centrifuged, resuspended in saline solution, and killed with heat. The suspensions may be standardized by direct microscopic count, mixed in required amounts, and stored in appropriate containers, which may be tested for safety, shelf life, and sterility in an approved manner. In addition to the pathogenic bacterial species and/or antigens thereof, a killed bacterial vaccine suitable for administration to humans may include 0.4% phenol preservative and/or 0.9% sodium chloride. The bacterial vaccine may also include trace amounts of brain heart infusion (beef), peptones, yeast extract, agar, sheep blood, dextrose, sodium phosphate and/or other media components.

In some embodiments, the bacterial vaccine may be used in tablet or capsule form or drops for oral ingestion, as an aerosol for inhalation, or as drops, aerosol or tablet form for sublingual administration.

In antigenic compositions comprising bacteria, the concentrations of specific bacterial species in compositions for subcutaneous or intradermal injection may be about 1 million to 100,000 million organisms per ml, or may be 100 million to 7000 million organisms per ml, or may be 500 million to 6000 million organisms per ml, or may be 1000 million to 5000 million organisms per ml, or may be 2000 million to 4000 million organisms per ml, or any integer within these ranges. The total concentration of bacteria per ml may range from 1 million to 100,000 million organisms per ml, or may be 50 million to 7000 million organisms per ml, or may be 100 million to 6000 million organisms per ml, or may be 500 million to 5000 million organisms per ml, or may be 1000 million to 4000 million organisms per ml, or any integer within these ranges.

In some embodiments, a selected killed bacterial vaccine for cancer of the lung tissue would include the common bacterial lung pathogens, and may for example be:

|  | bacteria per ml |
| --- | --- |
| Streptococcus pneumoniae | 600 million |
| Haemophilus influenzae | 400 million |
| Moraxella catarrhalis | 400 million |
| Mycoplasma pneumoniae | 300 million |
| Klebsiella pneumoniae | 300 million |
| total: | 2,000 million | or alternatively:

|  | bacteria per ml |
| --- | --- |
| Streptococcus pneumoniae | 600 million |
| Haemophilus influenzae | 300 million |
| Moraxella catarrhalis | 300 million |
| Mycoplasma pneumoniae | 400 million |
| Klebsiella pneumoniae | 400 million |
| total: | 2,000 million |

In some selected embodiments, a selected killed bacterial vaccine for cancer of the lung tissue would include only more common bacterial lung pathogens, and may for example be:

|  | bacteria per ml |
| --- | --- |
| Streptococcus pneumoniae | 800 million |
| Haemophilus influenzae | 600 million |
| Moraxella catarrhalis | 600 million |
| total: | 2,000 million | or alternatively:

|  | bacteria per ml |
| --- | --- |
| Streptococcus pneumoniae | 800 million |
| Mycoplasma pneumoniae | 600 million |
| Klebsiella pneumoniae | 600 million |
| total: | 2,000 million |

In further selected embodiments, a selected killed bacterial vaccine for cancer of the lung tissue would include only the most common bacterial lung pathogen, and may be:

|  | bacteria per ml |
| --- | --- |
| Streptococcus pneumoniae | 2,000 million |
| total: | 2,000 million | or

|  | bacteria per ml |
| --- | --- |
| Klebsiella pneumoniae | 2,000 million |
| total: | 2,000 million | or

|  | bacteria per ml |
| --- | --- |
| Mycoplasma pneumoniae | 2,000 million |
| total: | 2,000 million |

In some embodiments, an antigenic microbial composition for treating cancer at a particular site (e.g., cancer of the lung tissue) may include pathogenic microbes that commonly, more commonly, or most commonly cause infection in that tissue or organ (e.g., infection in the lung tissue i.e., pneumonia).

In general, the pathogenic bacterial species and antigens thereof of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population).

In some aspects, the invention involves the use of an anti-inflammatory in conjunction with vaccinations. In these embodiments, a wide variety of anti-inflammatory treatments may be employed, including effective amounts of non-steroidal anti-inflammatory drugs (NSAIDs), including but not limited to: diclofenac potassium, diclofenac sodium, etodolac, indomethicin, ketorolac tromethamine, sulindac, tometin sodium, celecoxib, meloxicam, valdecoxib, floctafenine, mefenamic acid, nabumetone, meloxicam, piroxicam, tenoxicam, fenoprofen calcium, flubiprofen, ibuprofen, ketoprofen, naproxen, naproxen sodium, oxaprozin, tiaprofenic acid, acetylsalicylic acid, diflunisal, choline magnesium trisalicylate, choline salicylate, triethanolamine salicylate, COX1 inhibitors, COX2 inhibitors (e.g., Vioxx™, and Celebrex™). A variety of herbs and natural health products may also be used to provide anti-inflammatory treatment, including but not limited to: green tea, fish oil, vitamin D, antioxidant vitamins and minerals (e.g., B carotene, vitamin A, vitamin C, vitamin D, vitamin E, co-enzyme Q10, selenium, etc.), resveratrol, turmeric, bromelain, boswellia, feverfew, quercetin, ginger, rosemary, oregano, cayenne, clove, nutmeg, willowbark. Alternative anti-inflammatory modalities may also include lifestyle modifications, such as: exercise, weight loss, smoking cessation, stress reduction, seeking social support, treatment of depression, stress management, abdominal breath work and dietary change (such as adopting a mediterranean diet, a low glycemic diet, eating non-charred foods, including foods having omega-3 fatty acids).

EXAMPLE 1

Clinical Studies

Bacterial Compositions

Five killed bacterial compositions have been used to treat a wide variety of cancer types and stages in blinded studies, as follows:
1. The Bayer Corporation MRV™ "Bayer MRV" (Hollister-Steir Laboratories, Spokane, Wash., U.S.A.), containing the following bacterial species:

|  | Organisms per ml |
|---|---|
| Staphylococcus aureus | 1200 million |
| viridans and non-hemolytic Streptococci | 200 million |
| Streptococcus pneumoniae | 150 million |
| Moraxella (Neisseria) catarrhalis | 150 million |
| Klebsiella pneumoniae | 150 million |
| Haemophilus influenzae | 150 million |

This vaccine was produced for the following indications: rhinitis, infectious asthma, chronic sinusitis, nasal polyposis and chronic serous otitis media. Cancer treatment was not indicated as an intended use for this vaccine. The vaccine also included the following ingredients: 0.4% phenol, 0.9% NaCl, trace amounts of brain heart infusion (beef), peptones, yeast extract, agar, sheep blood, dextrose, and sodium phosphates.
2. Stallergenes MRV "Stallergenes MRV" (Laboratories des Stallergenes, S.A., Fresnes, France), containing the following:

|  | Organisms per ml |
|---|---|
| Staphylococcus aureus | 600 million |
| Staphylococcus albus | 600 million |
| non-hemolytic Streptococci | 200 million |
| Streptococcus pneumoniae | 150 million |
| Moraxella (Neisseria) catarrhalis | 150 million |
| Klebsiella pneumoniae | 150 million |
| Haemophilus influenzae | 150 million |

This vaccine was produced for the same indications as the MRV vaccine i.e., recurrent respiratory tract infections, and listed cancer as a contraindication.

As set out below, surprisingly, these MRV vaccines, which contain many common lung pathogens, were found to be effective for the treatment of lung cancer.
3. Polyvaccinum Forte (PVF; Biomed S.A., Krakow, Poland), containing the following:

|  | Organisms per ml |
|---|---|
| Staphylococcus aureus | 500 million |
| Staphylococcus epidermidis | 500 million |
| Escherichia coli | 200 million |
| Corynebacterium pseudodiphtheriticum | 200 million |
| Streptococcus pyogenes | 100 million |
| Streptococcus salivarius (viridans Streptococci) | 100 million |
| Streptococcus pneumoniae | 100 million |
| Moraxella (Neisseria) catarrhalis | 100 million |
| Klebsiella pneumoniae | 100 million |
| Haemophilus influenzae | 100 million |

This vaccine was produced for chronic and recurrent inflammatory conditions of the upper and lower respiratory tract and genitourinary tract, including rhinopharyngitis, recurrent laryngitis, tracheitis, bronchitis, otitis media, chronic and recurrent neuralgia of trigeminal and occipital nerve, ischialgia, brachial plexitis, intercostals neuralgia, chronic cystoureteritis, vaginitis, adnexitis, and endometrium inflammation. Cancer treatment was not indicated as an intended use for this vaccine.

Of note, although the total concentration of bacteria in PVF is identical to that of the MRVs (Bayer and Stallergenes), patients typically demonstrated a visible inflammatory immune response to subcutaneous injection of the PVF composition at a much smaller dose than the usual dose required to achieve a similar skin response with the MRV composition, indicating that the immune reaction was likely occurring to one of the novel components in the Polyvaccinum Forte vaccine, such as E. coli. As set out below, surprisingly, PVF, which contains E. coli a common pathogen of the colon, abdomen, kidney, ovaries, peritoneum, liver and pancreas, has been found to be effective in the treatment of cancers in the colon, abdominal lymph nodes, kidney, ovary, peritoneum, liver and pancreas.
4. Staphage Lysate (Delmont Laboratories Inc., Swarthmore, Pa., USA), containing the following:
Staphylococcus aureus As set out below, surprisingly, Staphage Lysate, which contains Staphylococcus aureus a common pathogen of the breast and bone, was found to be effective in the treatment of cancer in the breast and bone.
Administration of MRV, Staphage Lysate and PVF The bacterial compositions (vaccines) were a suspension of killed bacterial cells and therefore, the suspensions were gently shaken prior to use to ensure uniform distribution prior to withdrawing dose from vial, and administered subcutaneously three times a week on Mondays, Wednesdays, and Fridays. Patients were advised to continue treatment for at least 6 months. The dose of vaccine required was determined by the adequacy of the immune reaction to the vaccine. Beginning with a very small dose (0.05 cc), the dose was gradually increased (by 0.01-0.02 cc each time) until an adequate immune reaction was achieved. This delayed local reaction at the injection site appeared within 2-48 hours after injection and lasted for up to 72 hours or longer. The goal was to achieve a one to two inch diameter round patch of pinkness/redness at the injection site, indicating adequate immune stimulation. Once this reaction was achieved, the dose was maintained at the level required to achieve this reaction. If the reaction was significantly less than two inches (e.g., half an inch) the dose was increased, if it was significantly more than two inches (e.g., three inches), the dose was decreased. This local immune reaction generally occurs within the first 24 hours after the injection. Patients were asked to check for this reaction and, if present, to measure or mark it. The maintenance dose required to achieve an adequate immune reaction varies considerably, depending on the individual's immune response—as little as 0.001 cc for some people, as much as 2 cc for others. The vaccine must be stored in a refrigerator (2° to 8° C.). The usual site for injection is the upper arms, the thighs or the abdomen. The exact site of each injection was varied so that it was not given in sites in which pinkness/ redness was still present. A known contraindication to the vaccines is hypersensitivity to any component of the vaccine.

A fifth vaccine, a polymicrobial oral vaccine, was used in alternative aspects of the invention, as follows:

5. Respivax, produced by BB-NCIPD Ltd (Bulgaria). This oral vaccine contained the following freeze-dried killed bacterial species:

|  | Organisms per mg |
|---|---|
| *Streptococcus pneumoniae* | 25 million |
| *Neisseria catarrhalis* | 25 million |
| *Streptococcus pyogenes* | 25 million |
| *Haemophilus influenzae* | 25 million |
| *Staphylococcus aureus* | 25 million |
| *Klebsiella pneumoniae* | 25 million |

Administration of Respivax

The Respivax oral vaccine was produced for the treatment for chronic respiratory infection, and contains many of the most common respiratory tract pathogens, including many of the most common causes of lung infection. Patients were treated with a dose of one 50 mg tablet per day, providing the equivalent of $1.25 \times 10^9$ cells of each species per dose. Patients were prescribed the above dose for a continuous period of at least 6 months.

As set out below, surprisingly, Respivax oral vaccine, which contains many common lung pathogens, was found to be effective for the treatment of cancer of the lung.

EXAMPLE 1A

Cancer of the Lung

This section relates to primary cancer in the lung, or metastases to the lung, treated with microbial pathogens of the lung, such as endogenous respiratory bacteria flora.

Patients qualified for the lung cancer study if they were initially diagnosed with stage 3B or 4-lung (inoperable) cancer. Lung cancer staging was performed using standard methods as for example described in AJCC: Cancer Staging Handbook (sixth edition) 2002; Springer-Verlag New York: Editors: Fredrick Greene, David Page and Irvin Fleming, or in International Union Against Cancer: TNM Classification of Malignant Tumors (sixth edition) 2002; Wiley-Liss Geneva Switzerland: Editors: L. H. Sobin and C. H. Wittekind. For example, lung cancers may be classified as follows:

TNM Lung Clinical and Pathological Classification
T PRIMARY TUMOUR
TX Primary tumour cannot be assessed, or tumour proven by the presence of malignant cells in sputum or bronchial washings but not visualized by imaging or bronchoscopy
Tis Carcinoma in situ
T0 No evidence of primary tumour
T1 Tumour 3 cm or less in greatest dimension, surrounded by lung or visceral pleura, without bronchoscopic evidence of invasion more proximal than the lobar bronchus (ie, not in the main bronchus)
T2 Tumour with any of the following features of size or extent: More than 3 cm in greatest dimension Involves main bronchus, 2 cm or more distal to the carina Invades visceral pleura Associated with atelectasis or obstructive pneumonitis that extends to the hilar region but does not involve the entire lung
T3 Tumour of any size that directly invades any of the following: chest wall (including superior sulcus tumours), diaphragm, mediastinal pleura, parietal pericardium; or tumour in the main bronchus less than 2 cm distal to the carina but without involvement of the carina; or associated atelectasis or obstructive pneumonitis of the entire lung
T4 Tumour of any size that invades any of the following: mediastinum, heart, great vessels, trachea, esophagus, vertebral body, carina; or tumour with a malignant pleural or pericardial effusion; or with separate tumour nodule(s) within the ipsilateral primary-tumour lobe of the lung,
N REGIONAL LYMPH NODES
NX Regional lymph nodes cannot be assessed
N0 No regional lymph node metastasis
N1 Metastasis in ipsilateral peribronchial and/or ipsilateral hilar lymph nodes and intrapulmonary nodes, including involvement by direct extension
N2 Metastasis in ipsilateral mediastinal and/or subcarinal lymph node(s)
N3 Metastasis in contralateral mediastinal, contralateral hilar, ipsilateral or contralateral scalene, or supraclavicular lymph node(s)
M DISTANT METASTASIS
MX Distant metastasis cannot be assessed
M0 No distant metastasis
M1 Distant metastasis; includes separate tumour nodule(s) in the non-primary-tumour lobe (ipsilateral or contralateral)
Stage Grouping of TNM Subsets:

| Occult carcinoma | TX | N0 | M0 |
|---|---|---|---|
| Stage 0 | Tis | N0 | M0 |
| Stage IA | T1 | N0 | M0 |
| Stage IB | T2 | N0 | M0 |
| Stage IIA | T1 | N1 | M0 |
| Stage IIB | T2 | N1 | M0 |
|  | T3 | N0 | M0 |
| Stage IIIA | T3 | N1 | M0 |
|  | T1 | N2 | M0 |
|  | T2 | N2 | M0 |
|  | T3 | N2 | M0 |
| Stage IIIB | Any T | N3 | M0 |
|  | T4 | Any N | M0 |
| Stage IV | Any T | Any N | M1 |

Charts with diagnostic codes 162.9 (lung cancer) and 197 (metastatic cancer) were collected manually and electronically. Information was collected on these patients, such as date of diagnosis, date of death, and cancer stage. Charts for patients were reviewed to confirm the date of diagnosis and cancer stage. Patients were excluded from the analysis for the following reasons: 1) wrong stage; 2) missing data; 3) no chart, or; 4) chart did not reach in time for the data analysis. 20 patients were excluded from the study because their charts have not arrived yet or there was insufficient information, of which 6 were MRV users. The study group includes 108 patients in total: 50 who took the MRV vaccine and 58 who did not take the MRV vaccine.

Comparison of survival of patients initially diagnosed with stage 3B and 4 lung cancer who took MRV with patients who didn't take MRV and with SEER standard survival data for patients initially diagnosed with stage 3B and 4 lung cancer (FIG. 1) was as follows:

|  | SEER | non-MRV | MRV |
|---|---|---|---|
| median survival: | 5 months | 10.5 months | 12.5 months |
| survival at 1 year: | 25% | 45% | 58% |
| survival at 3 years: | 5% | 3% | 20% |
| survival at 5 years: | 3% | 0% | 10% |

Figure 2:
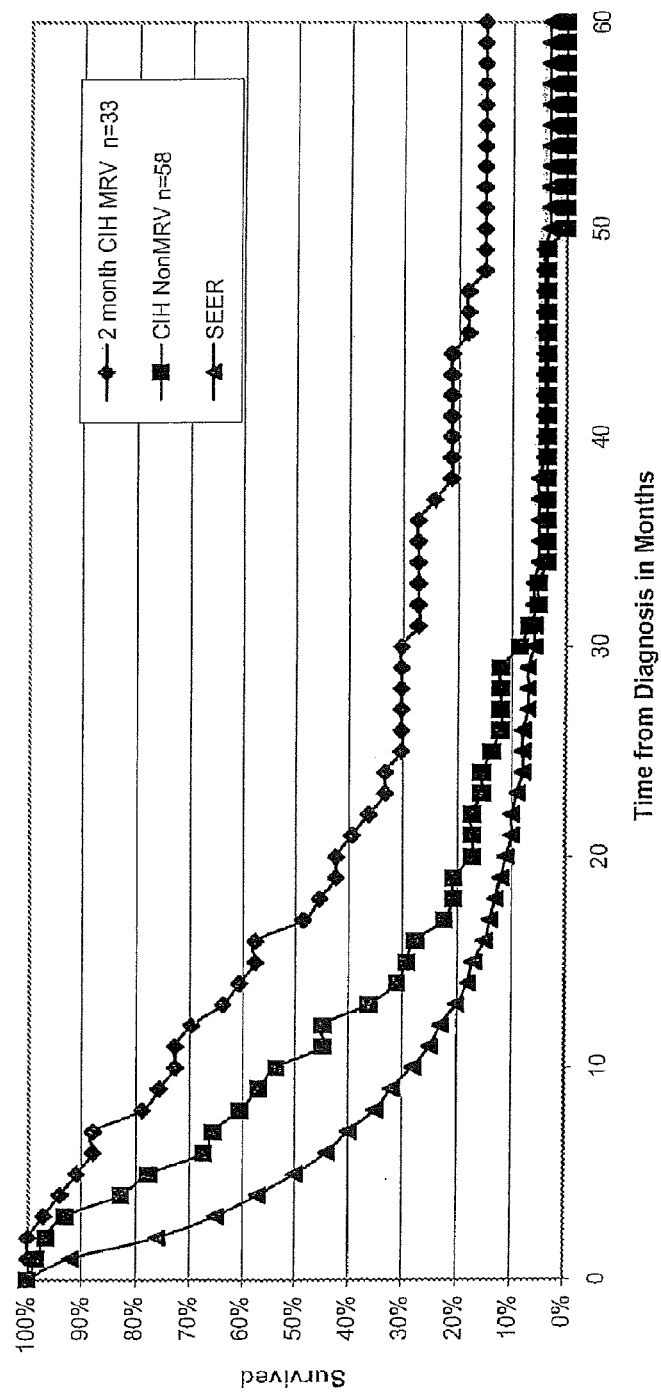
FIG. 2 shows a survival curve for a cumulative series of patients diagnosed with stage 3B or 4 inoperable lung cancer (patients treated for at least 2 months with MRV), comparing patients treated with MRV, patients not treated with the MRV, and a standard SEER survival curve.

A comparison of survival (as above), including only those patients who took MRV for at least 2 months (FIG. 2) is as follows:
median survival: 16.5 months
survival at 1 year: 70%
survival at 3 years: 27%
survival at 5 years: 15%

Median survival and survival at 1 year, 3 years and 5 years, was substantially better in the group that was treated with MRV (containing bacteria which commonly cause lung infection), evidence of the effectiveness of this vaccine for the treatment of lung cancer. Patients who were treated with the MRV vaccine for more than 2 months had higher survival rates, further evidence of the effectiveness of this vaccine for the treatment of lung cancer.

Figure 3:
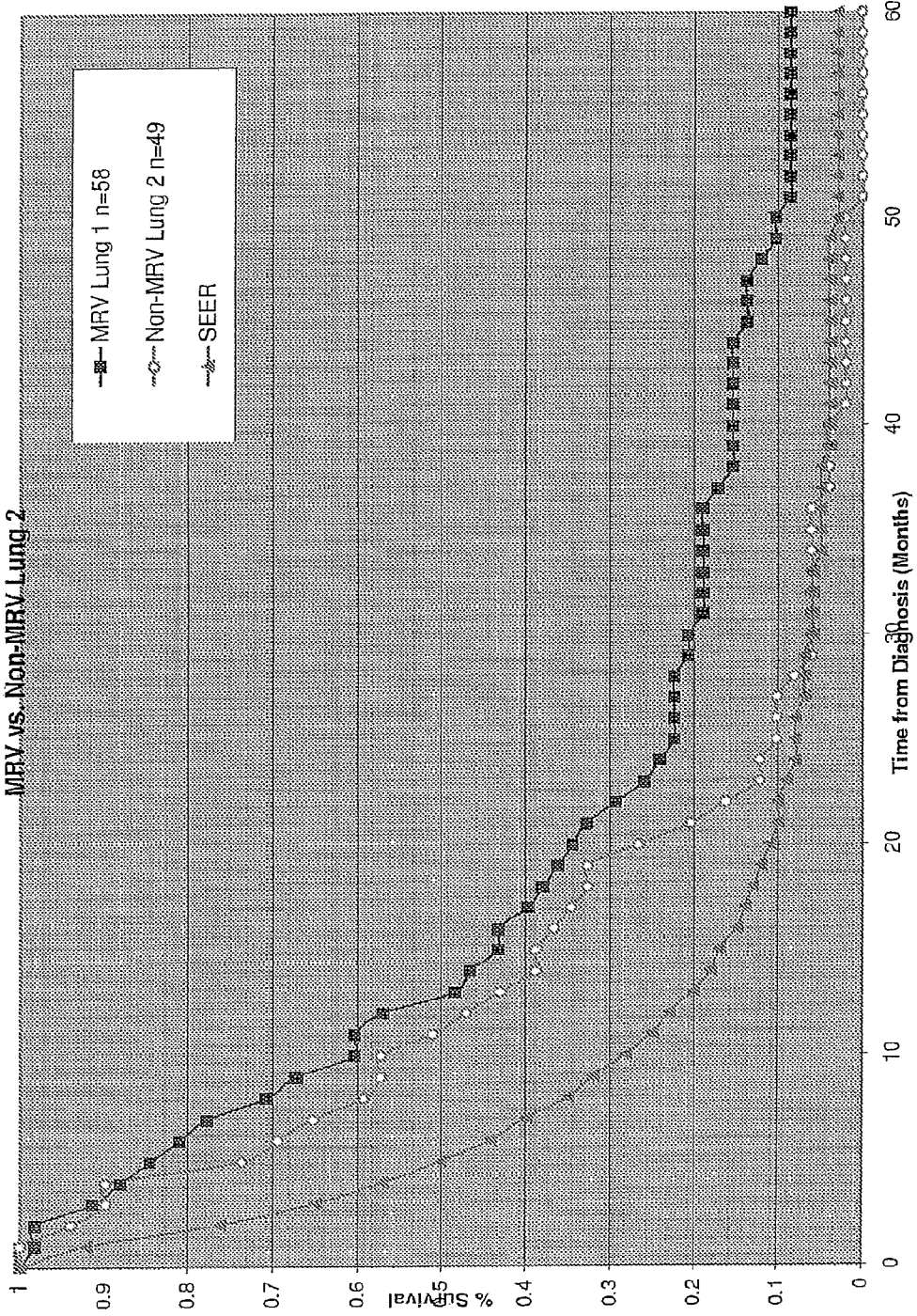
FIG. 3 shows a survival curve for a cumulative series of patients diagnosed with stage 3B or 4 lung cancer, illustrating the benefits of treatment with the MRV composition of the invention, comparing patients treated with MRV, patients not treated with the MRV, and a standard SEER survival curve.

An alternative analysis was conducted on data that included a patient population to whom the MRV composition was not available, to address a perceived potential for bias caused by sicker patients being more likely to choose the novel treatment (with MRV) and healthier patients being potentially less likely to submit to the use of the antigenic compositions of the invention. Comparison of survival of MRV patients to whom the MRV composition was available (designated "Lung 1") to survival of non-MRV patients to whom the MRV composition was not available (designated "Lung 2") removes some of this selection bias, providing a clearer and more accurate illustration of the benefit of MRV treatment, as illustrated in FIG. 3.

In some embodiments, particularly striking clinical benefits have been obtained with antigenic bacterial compositions used in repeated frequent injections (i.e., three times per week) for a prolonged period of time—such as at least 2, 3, 4, 5, 6 or 12 months, or 2, 3, 4 or 5 years (in the context of advanced cancer such as inoperable lung cancer, the longer periods may be most beneficial). Treatments of this kind may be carried out so as to provide sustained, prolonged immune stimulation. When the above analysis is restricted to patients who were treated with MRV for a minimum of 2 months, the survival advantage of MRV treatment is even more clearly illustrated FIG. 4.

Figure 4:
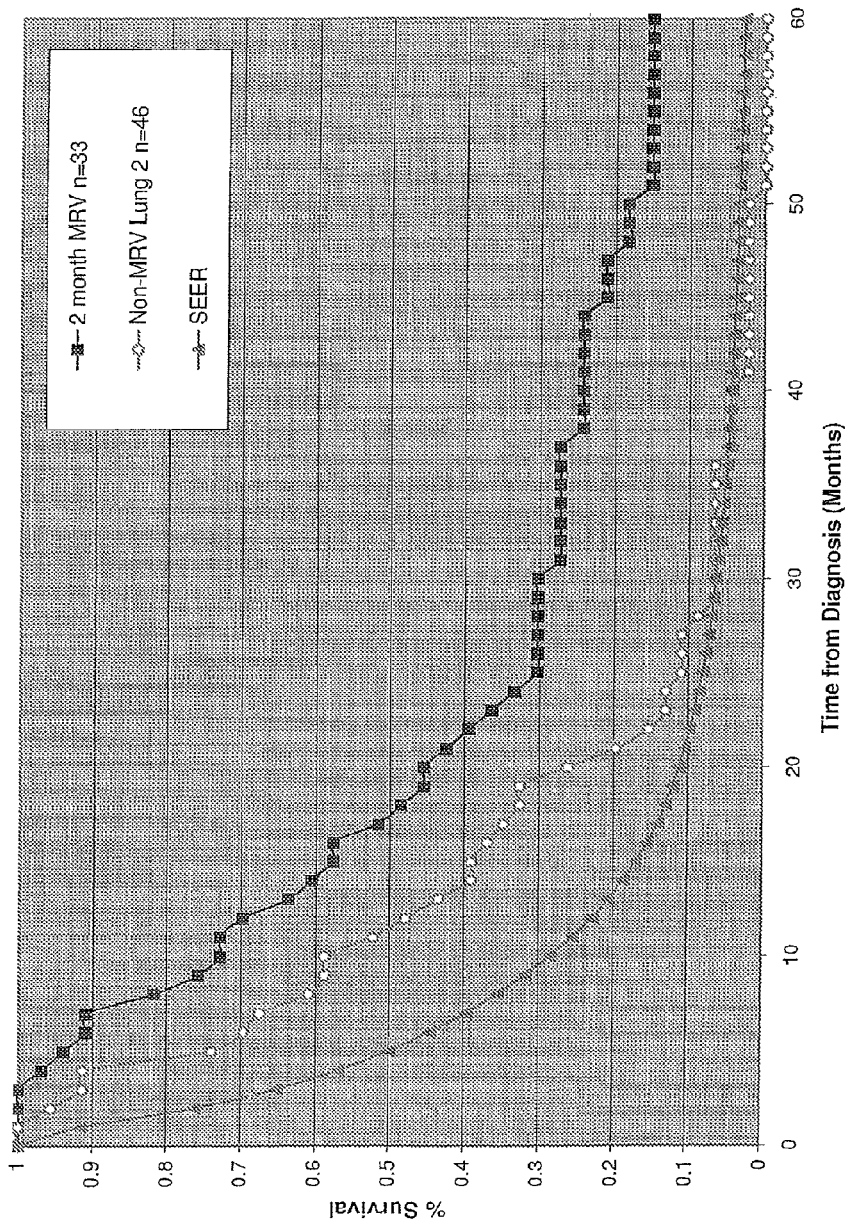
FIG. 4 shows a survival curve for a cumulative series of patients diagnosed with stage 3B or 4 lung cancer, illustrating the effect of treatments for at least 2 months, comparing patients treated with MRV, patients not treated with the MRV, and a standard SEER survival curve.

As illustrated in FIG. 4, one-year survival of stage 3B or 4 lung cancer patients treated with MRV for at least two months was 70%, compared to just 48% for the non-MRV Lung 2 group and 23% for the SEER database group. 3-year survival of the MRV group was more than 4 times that of both the non-MRV patients and the SEER registry. None of the non-MRV group in the Lung 2 study survived for 5 years, whereas 15% of patients treated with MRV for a minimum two-month period were still alive 5 years after diagnosis. In the context of an illness such as inoperable lung cancer that is considered terminal and has a usual 5-year survival rate of only 3% (SEER registry), the above results are extremely encouraging and surprising.

Figure 5:
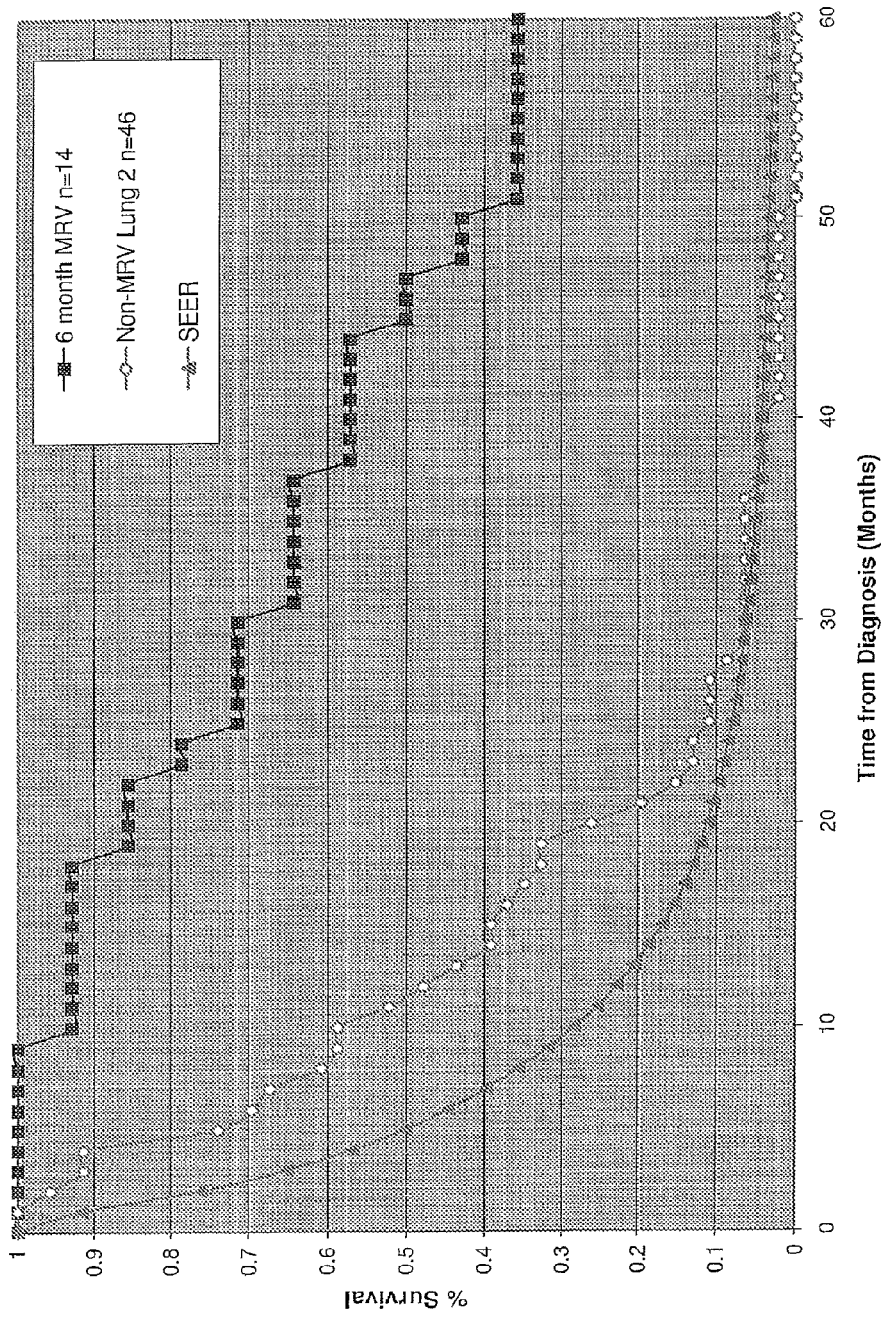
FIG. 5 shows a survival curve for a cumulative series of patients diagnosed with stage 3B or 4 lung cancer, illustrating the effect of treatments for at least 6 months duration, comparing patients treated with MRV, patients not treated with the MRV, and a standard SEER survival curve.

When the analysis of patient data is restricted to patients who were treated with MRV for at least 6 months, the survival curve is truly remarkable, as illustrated in FIG. 5. More than 60% of patients were alive at 3 years, more than 10 times the survival in both the non-MRV group and the SEER registry. 36% (5 of 14 patients) of patients who were treated with MRV for at least 6 months were alive 5 years after diagnosis, compared with only 3% in the SEER database and 0% in the non-MRV group. These remarkable results, in the context of a cancer diagnosis that is considered terminal, are extremely promising and surprising. Accordingly, in some embodiments, cancers, such as advanced cancers, such as inoperable lung cancer, may be treated over a dosing duration of at least 1, 2, 3, 4, 5, 6, 7, 8, 9, 10, 11 or 12 months, 2 years, 3 years, 4 years, 5 years, or indefinitely.

Restricting analysis to those patients who were treated with MRV for a minimum period of time (e.g., 6 months) introduces a bias in favour of the MRV group, since MRV patients who survived for less than that period of time are excluded from the group (including those who died before they could complete the 6 months of treatment). A detailed statistical analysis of this bias, with compensatory exclusion of short-term survivors in both the non-MRV and SEER groups, demonstrates that this bias played a very minor role in the truly remarkable survival advantage of patients who were treated with the MRV for at least 6 months.

Figure 11:
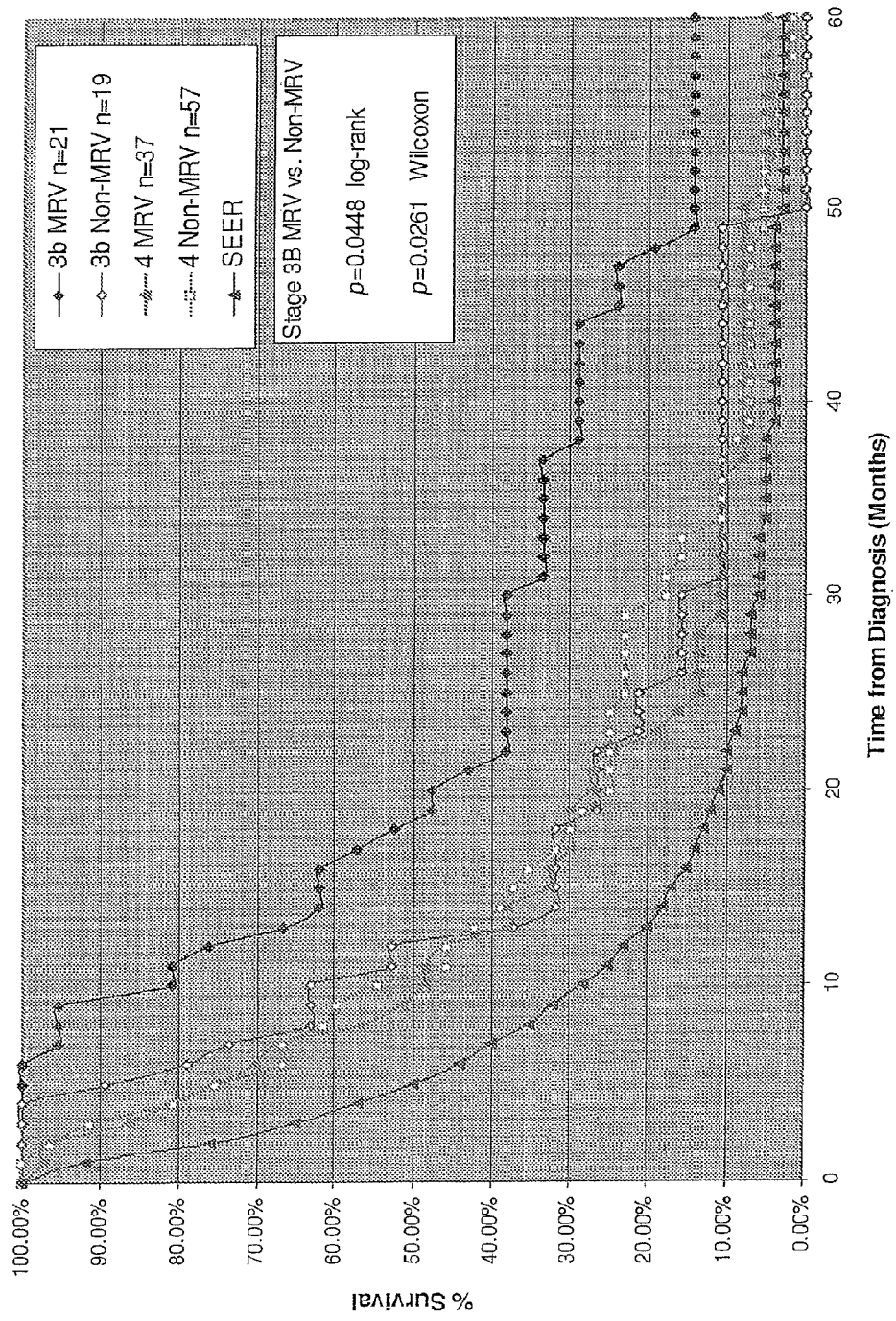
FIG. 11 shows a survival curve for a cumulative series of patients diagnosed with stage 3B lung cancer, illustrating the benefits of treatment with the MRV composition of the invention, comparing patients treated with MRV, patients not treated with the MRV, and a standard SEER survival curve.

In stage 3B lung cancer, cancer is confined to the lungs, and thus, a targeted anti-cancer treatment response may be stimulated, in accordance with various aspects of the invention, by a vaccine, such as MRV, comprised of lung pathogens. In stage 4 lung cancer, the cancer has metastasized to distant organs not amenable to targeted stimulation by lung pathogens in accordance with methods of the invention. Thus, in accordance with some embodiments, patients with stage 3B lung cancer may be selected for treatment with MRV vaccine, since all of the cancer is confined to the lungs and thus, will be targeted by the MRV vaccine. When the analysis of patient data is restricted to patients with stage 3B lung cancer, comparison of survival curves even more clearly illustrates the benefit of MRV treatment. As illustrated in FIG. 11, one-year survival of stage 3B lung cancer patients treated with MRV was 76%, compared to just 53% for the non-MRV Lung 2 group and 23% for the SEER database group. 3-year survival of the MRV group was 3 times that the non-MRV patients and more than 6 times the SEER registry. None of the non-MRV group survived for 5 years, whereas 14% of stage 3B patients treated with MRV were still alive 5 years after diagnosis. In the context of an illness such as inoperable stage 3B lung cancer that is considered terminal and has a usual 5-year survival rate of only 5% (SEER registry), the above results are extremely encouraging and surprising.

Figure 12:
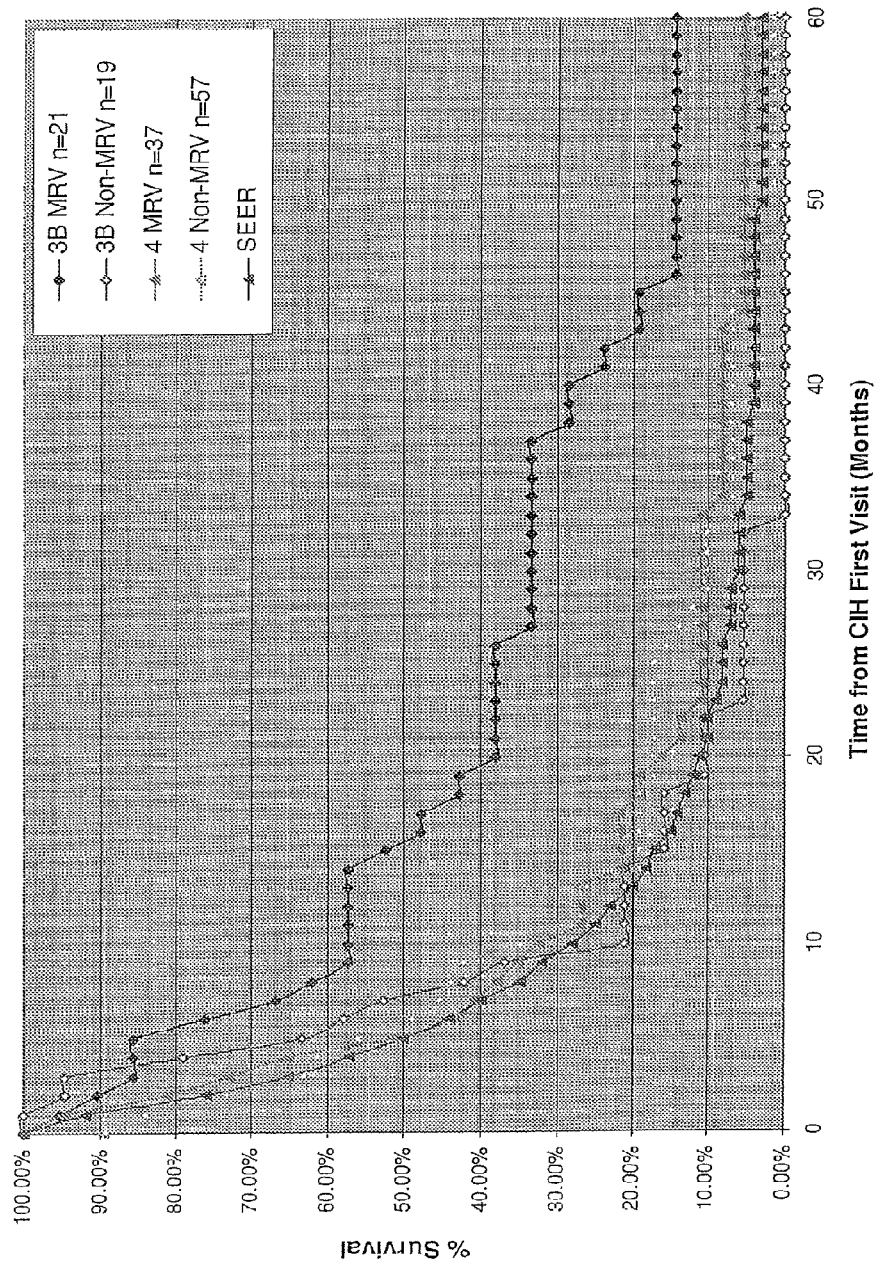
FIG. 12 shows a survival curve measured from date of first visit for a cumulative series of patients diagnosed with stage 3B lung cancer, illustrating the benefits of treatment with the MRV composition of the invention, comparing patients treated with MRV, patients not treated with the MRV, and a standard SEER survival curve.

As some patients did not have their first visit for many months or even a year or two after diagnosis, their inclusion in the survival curves skews the curve towards longer survival. In order to determine whether this bias influenced the difference in survival curves, survival was analysed from date of first visit which excludes this bias, as illustrated in FIG. 12. Comparison of survival curves of stage 3B lung cancer patients in FIG. 12 demonstrates an even greater survival benefit for MRV treatment than illustrated in FIG. 11, indicating that the benefit of MRV treatment was partially masked in FIG. 11. As illustrated in FIG. 12, 1-year survival (from date of first visit) of stage 3B lung cancer patients treated with MRV was 57%, compared to only 21% for stage 3B patients not treated with MRV. While no stage 3B lung cancer patients not treated with MRV survived for 3 years, 3-year survival of stage 3B patients treated with MRV was 33% and 5-year survival was 14%, a remarkable and unexpected result.

Figure 13:
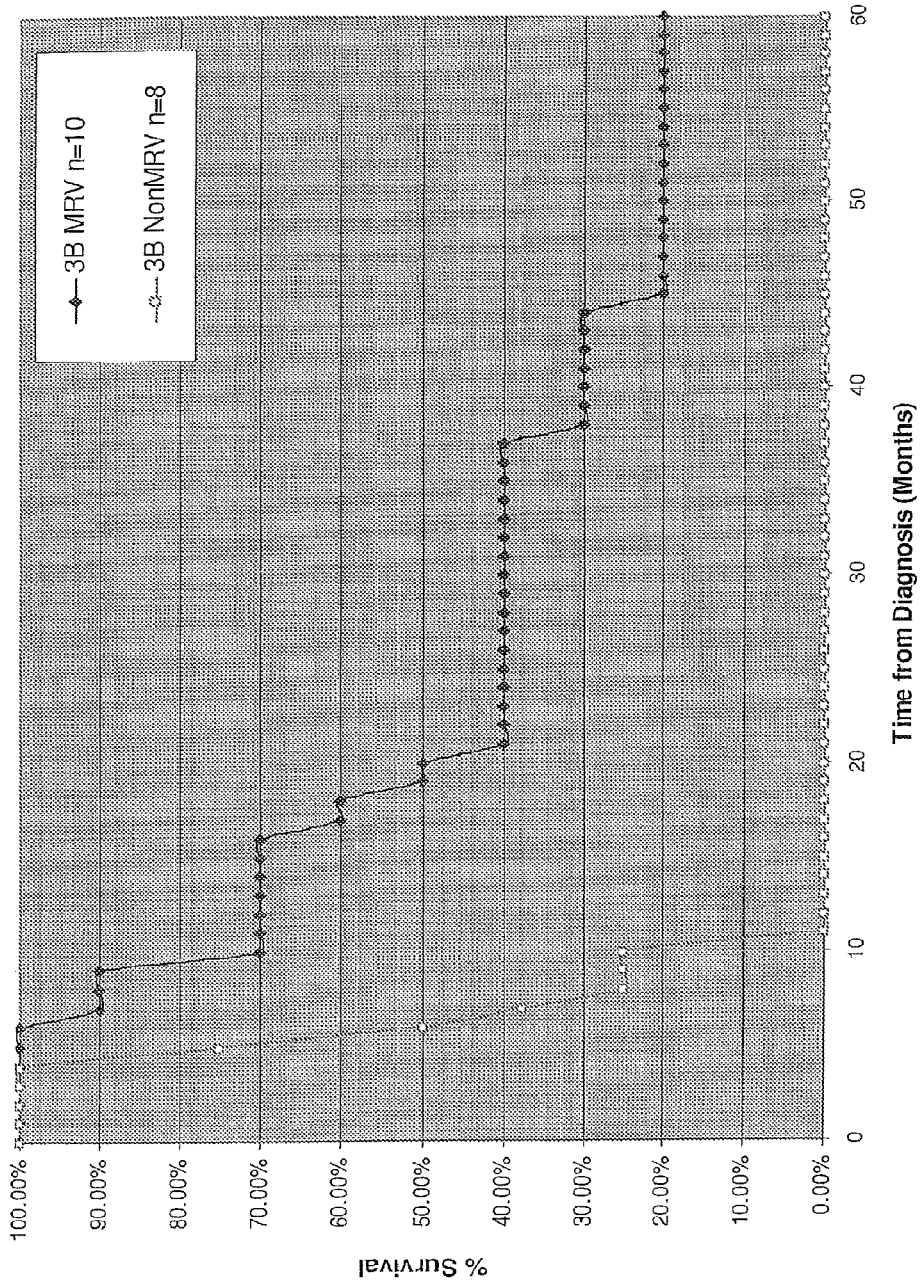
FIG. 13 shows a survival curve for a cumulative series of patients diagnosed with stage 3B lung cancer whose first visit was within 3 months of diagnosis, illustrating the benefits of early treatment with the MRV composition of the invention, comparing patients treated with MRV and patients not treated with the MRV.

When analysis was restricted to stage 3B lung cancer patients whose first visit was within 3 months of diagnosis, the benefits of early treatment with MRV are clearly illustrated. As illustrated in FIG. 13, while all stage 3B lung cancer patients who had their first visit within 3 months of diagnosis died within 1 year of diagnosis, 70% of stage 3B lung cancer patients treated with MRV within 3 months of diagnosis survived for 1 year, 40% survived 3 years and 20% survived years, a truly remarkable survival benefit for early MRV treatment.

One aspect of the invention involves the treatment of primary lung cancers or metastasis to the lung with antigenic compositions that comprise antigenic determinants of microbial pathogens that are known to be lung pathogens, such as exogenous lung pathogens or pathogens that are members of the endogenous flora of the respiratory system. For example, antigenic determinants of the endogenous bacterial respiratory flora species that most commonly cause infection in the lung (see Table 5) may be used to treat primary and metastatic cancers situated in the lung: *Streptococcus pneumoniae, Moraxella catarrhalis, Mycoplasma pneumoniae, Klebsiella pneumoniae, Haemophilus influenza*. Similarly, common viral lung pathogens from Table 5 may be selected for use in some embodiments. Alternatively, a more exhaustive list of endogenous lung pathogens may be selected from Table 1, based on the pathogenicity information provided in Table 2. In further alternative embodiments, viral lung pathogens listed in Table 4 may be used. And in further alternative embodiments, exogenous bacterial lung pathogens from Table 3 may be used in formulating antigenic compositions of the invention, i.e. selected from the group consisting of: *Achromobacter* spp., *Actinomadura* spp., *Alcaligenes* spp., *Anaplasma* spp., *Bacillus anthracis*, other *Bacillus* spp., *Balneatrix* spp., *Bartonella henselae, Bergeyella zoohelcum, Bordetella holmesii, Bordetella parapertussis, Bordetella pertussis, Borrelia burgdorferi, Borrelia recurrentis, Brucella* spp., *Burkholderia gladioli, Burkholderia mallei, Burkholderia pseudomallei, Campylobacter fetus, Capnocytophaga canimorsus, Capnoctyophaga cynodegmi, Chlamydia pneumoniae, Chlamydia psittaci, Chlamydophila pneumoniae, Chromobacterium violaceum, Chlamydophila psittaci, Chryseobacterium* spp., *Corynebacterium pseudotuberculosis, Coxiella burnetii, Francisella tularensis, Gordonia* spp., *Legionella* spp., *Leptospirosis* spp., *Mycobacterium avium, Mycobacterium kansasii, Mycobacterium tuberculosis*, other *Mycobacterium* spp., *Nocardia* spp., *Orientia tsutsugamushi, Pandoraea* spp., *Pseudomonas aeruginosa*, other *Pseudomonas* spp., *Rhodococcus* spp., *Rickettsia conorii, Rickettsia prowazekii, Rickettsia rickettsiae, Rickettsia typhi*.

For example, since the MRV compositions contain many of the most common lung pathogens, these vaccines may be used to treat primary lung cancer or lung metastases, as illustrated in the cumulative data presented here, and in a number of the case reports. In accordance with the foregoing results, one aspect of the invention involves the treatment of primary lung cancer and metastasis to the lung with antigenic compositions that comprise antigenic determinants of microbial pathogens that are known to be pathogenic in the lung, such as exogenous lung pathogens or pathogens that are members of the endogenous flora of the respiratory tract. In selected embodiments, antigenic determinants of the common lung pathogens may be used to treat primary and metastatic cancers situated in the lung, for example, antigenic determinants from one or more of the following bacterial species or viral types: *Streptococcus pneumoniae, Moraxella catarrhalis, Mycoplasma pneumoniae, Klebsiella pneumoniae, Haemophilus influenza*, influenza virus, adenovirus, respiratory syncytial virus, parainfluenza. In further selected embodiments, antigenic determinants of *Streptococcus pneumoniae*, the most common cause of bacterial lung infection, may be used alone or with other of the most common pathogens of the lung to treat cancer of the lung.

Primary lung cancer may also arise from bronchial tissue and therefore, in some embodiments, antigenic compositions that comprise antigenic determinants of microbial pathogens that are known to cause bronchial infection may be used to treat patients with cancer situated in the bronchial tissue, including, for example, the following common causes of bronchial infection: *Mycoplasma pneumoniae, Chlamydophila pneumoniae, Bordetella pertussis, Streptococcus pneumoniae, Haemophilus influenzae*, influenza virus, adenovirus, rhinovirus, coronavirus, parainfluenza, respiratory syncytial virus, human metapneumovirus, or coxsackievirus. Lung cancer (or lung metastases) that is located in both lung and bronchial tissue may be treated with antigenic compositions that comprise antigenic determinants of microbial pathogens that are known to cause both lung and bronchial infection (for example, *Streptococcus pneumoniae, Haemophilus influenza* and *Mycoplasma pneumoniae* are all common lung and bronchial pathogens) or alternatively, with antigenic compositions that comprise antigenic determinants of microbial pathogens that are known to cause lung infection and antigenic determinants of microbial pathogens that are known to cause bronchial infection.

EXAMPLE 1B

Breast Cancer with Metastasis to the Bone or Lung

Figure 6:
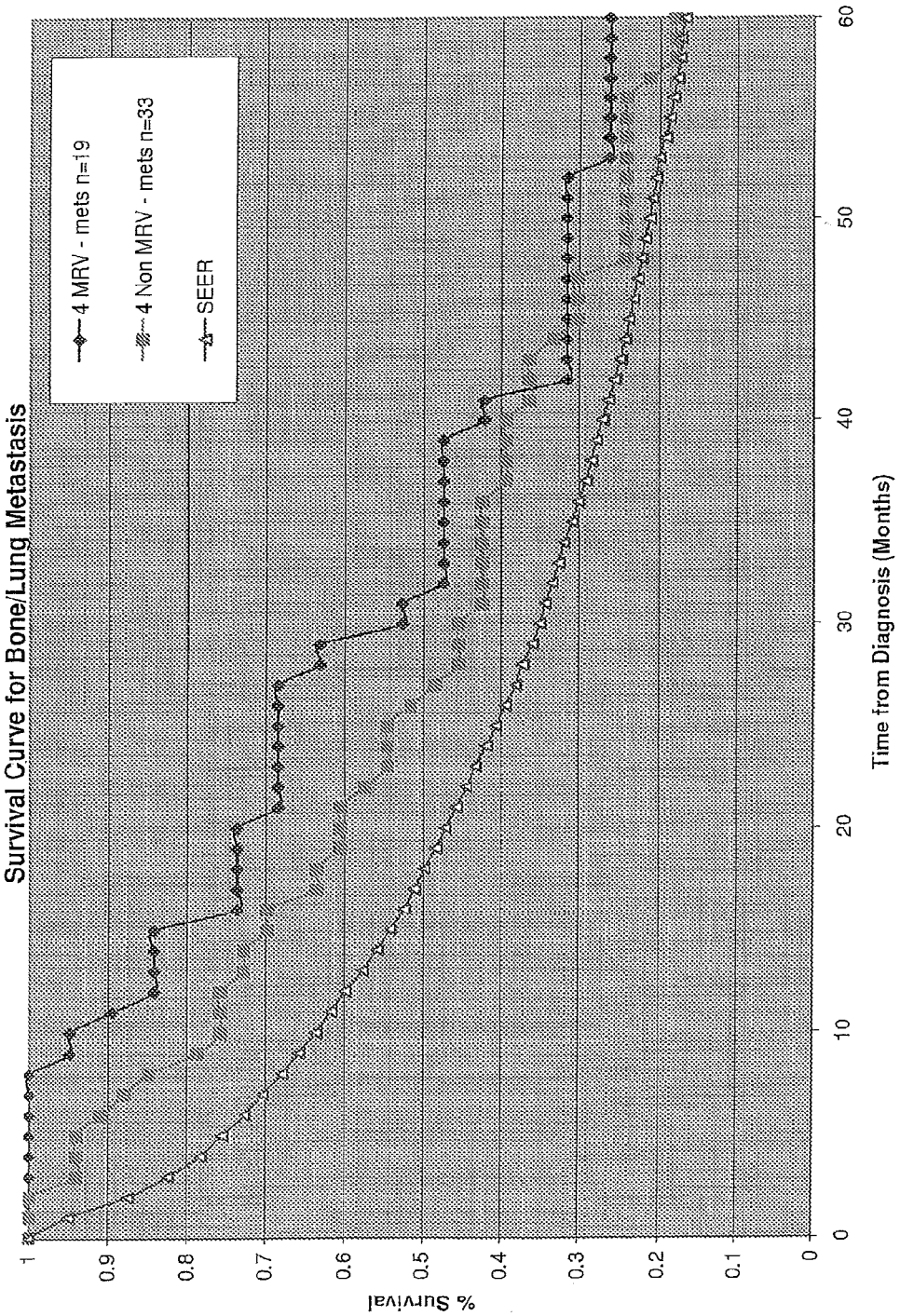
FIG. 6 shows a survival curve for a cumulative series of 52 breast cancer patients with metastases to bone and/or lung, comparing patients treated with MRV, patients not treated with the MRV, and a standard SEER survival curve.

The most common cause of both breast infection and bone infection is *Staphylococcus aureus*. Accordingly, in one aspect of the invention, an antigenic composition comprising antigenic determinants of *S. aureus* may be used to treat breast cancer with metastases to the bone. The remarkable case of Patient R (PtR), treated with a *Staphylococcus aureus* vaccine, set out below in the Case Reports, illustrates the efficacy of this approach to treating breast cancer with bone metastases. As illustrated in FIG. 6, in a cumulative series of 52 patients, survival of breast cancer patients with metastases to bone and/or lung treated with MRV (n=19), which contains *Staphylococcus aureus*, was better than the survival of patients not treated with the MRV vaccine (n=33):

|  | % survival MRV patients | % survival non-MRV patients |
|---|---|---|
| 10 months | 95% | 76% |
| 20 months | 74% | 61% |
| 5 years | 26% | 18% |

In accordance with the foregoing results, one aspect of the invention involves the treatment of primary cancer in the breast or metastasis to the breast with antigenic compositions that comprise antigenic determinants of microbes that are known to cause breast infection, and treatment of primary cancer of the bone or metastasis to the bone with antigenic compositions that comprise antigenic determinants of bacterial species or viruses that are known to cause bone infection. In selected embodiments, a vaccine comprising antigenic determinants of *Staphylococcus aureus*, the most common cause of both breast and bone infection, may be used alone or in combination with other of the most common pathogens of the breast to treat cancer in the breast, or alone or in combination with other of the most common pathogens of the bone to treat cancer in the bone.

EXAMPLE 1C

Metastases to the Bone

Figure 7:
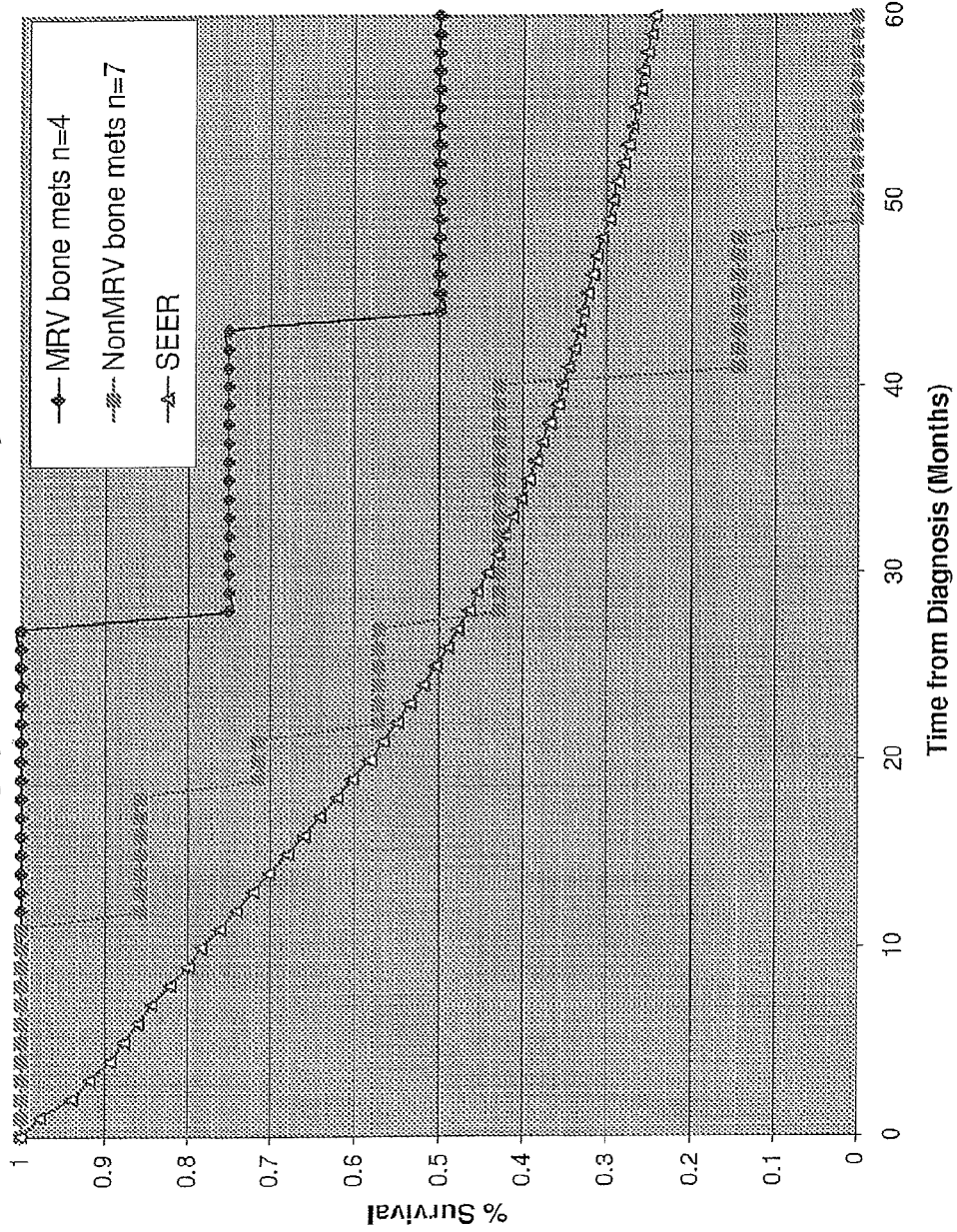
FIG. 7 is a comparison of survival of a cumulative series of metastatic prostate cancer patients who had surgery or radiation to destroy their prostate gland (and thus, the primary tumour) and who had detectable cancer limited to bone metastases, comparing patients treated with MRV, patients not treated with the MRV, and a standard SEER survival curve.

One of the most common sites for metastases in patients with prostate cancer is bone. In one aspect of the invention, the MRV composition, which contains antigenic determinants of *S. aureus*, the most common cause of bone infection, may be used for the treatment of metastases to the bone, for example in patients who have, or who have had, a primary prostate cancer. The graph of FIG. 7 is a comparison of survival of a cumulative series of metastatic prostate cancer patients who had surgery or radiation to destroy their prostate gland (and thus, the primary tumour) and who had detectable cancer limited to bone metastases. As illustrated, the survival of patients treated with MRV (n=4) is substantially better than that of patients not treated with MRV (n=7):

|  | % survival MRV patients | % survival non-MRV patients |
|---|---|---|
| 2 years | 100% | 57% |
| 3 years | 75% | 43% |
| 5 years | 50% | 0% |

In accordance with the foregoing results, one aspect of the invention involves the treatment of primary bone cancers or metastases to the bone with antigenic compositions that comprise antigenic determinants of microbial pathogens that are known to cause bone infection, such as exogenous bone pathogens or pathogens that are members of the endogenous flora of the skin, mouth or colon. For example, in selected embodiments, antigenic determinants of one or more of the following microbial species from the list of common bone pathogens may be used to treat primary and metastatic cancers situated in the bone: *Staphylococcus aureus*, coagulase-negative staphylococci, *Streptococcus pyogenes*, *Streptococcus pneumoniae*, *Streptococcus agalactiae*, other streptococci spp., *Escherichia coli*, *Pseudomonas* spp., *Enterobacter* spp., *Proteus* spp., *Serratia* spp., parvovirus B19, rubella, hepatitis B. In further selected embodiments, *Staphylococcus aureus*, the most common cause of bone infection, may be used alone or with other of the most common pathogens of the bone to treat cancer of the bone.

EXAMPLE 1D

Cancer Situated in the Colon

Treatment with the PVF composition has been shown to improve the survival of colon cancer patients (see FIG. 8), as illustrated by a comparison of the following four colon cancer patient groups:
Stage 4 colon cancer patients who were treated with MRV.
Stage 4 colon cancer patients who were not treated with a vaccine.
Stage 4 colon cancer patients who were treated with PVF vaccine.
Stage 4 colon cancer patients from the SEER (Surveillance, Epidemiology and End Results) database.

This example illustrates that patients with colon cancer treated with PVF, which contains *E. coli* the most common cause of bacterial infection of the colon, have substantially improved survival.

Patients qualified for the first two groups of this study if they presented with stage 4 colon cancer. Patients were excluded from this analysis for the following reasons:
incorrect diagnosis
incorrect stage
missing essential data (e.g., date of death)
no chart
chart did not reach us in time for the data analysis.

Figure 8:
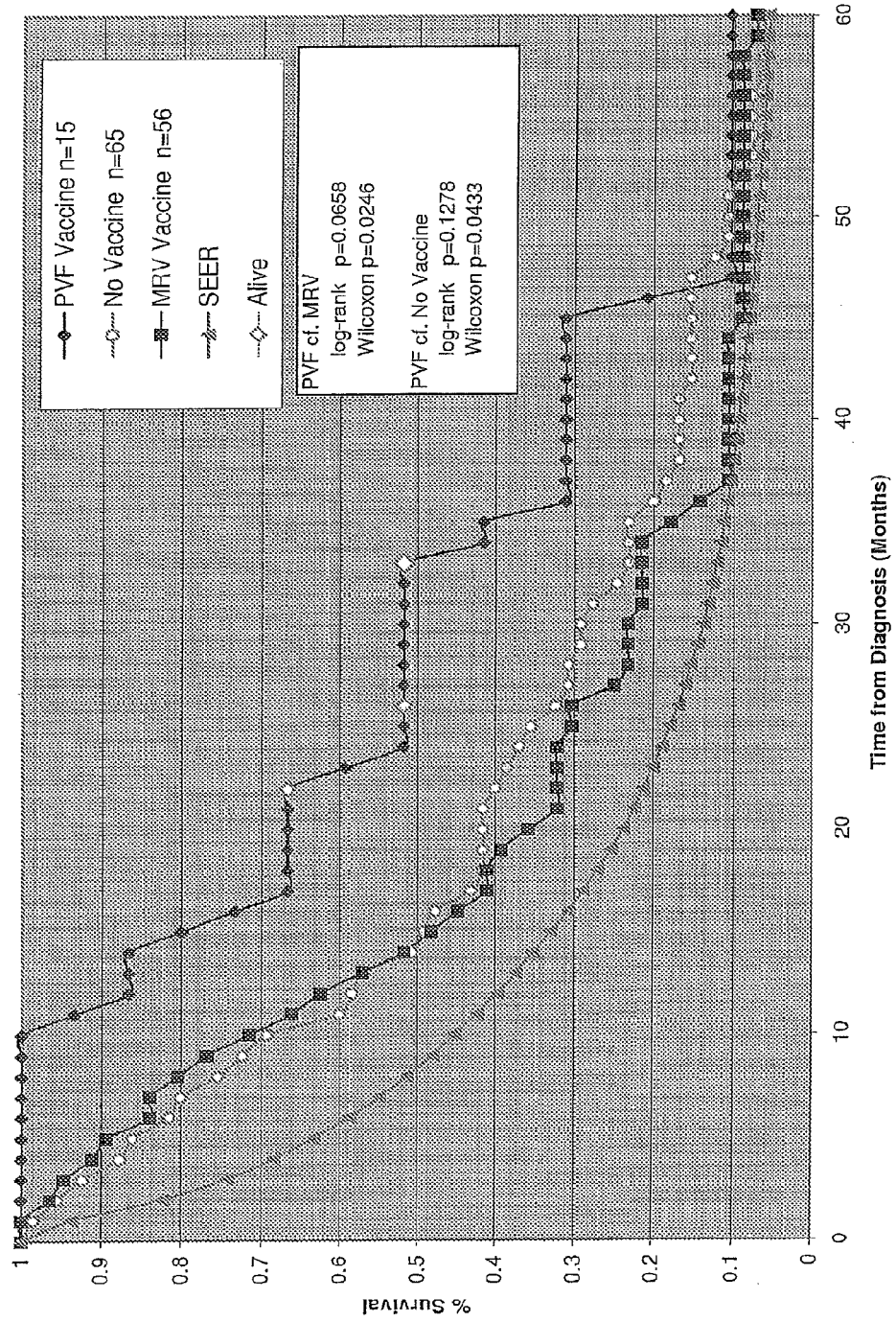
FIG. 8 shows a survival curve for a cumulative series of patients initially diagnosed with Stage 4 colorectal cancer, comparing patients treated with PVF, patients treated with MRV, patients not treated with an antigenic composition and a standard SEER survival curve.

The patient group included a total of 136 stage 4 colon cancer patients: 15 who took the PVF vaccine, 56 who took the MRV vaccine, and 65 who did not take a vaccine. Results are illustrated in FIG. 8, as follows:

|  | SEER | no vaccine | MRV | PVF |
|---|---|---|---|---|
| median survival: | 8.4 mo. | 15.1 mo. | 15.0 mo. | 33.6 mo. |
| at 10 months | 45% | 69% | 71% | 100% |
| at 20 months | 24% | 42% | 36% | 67% |
| at 30 months | 14% | 29% | 23% | 52% |
| at 5 years | 5% | 6% | 7% | 10% |

The median survival of patients with stage 4 colon cancer treated with PVF (which contains *E. coli*, one of the most common colonic pathogens) was more than double that of patients treated with MRV (which does not contain colonic pathogens) or patients not treated with a vaccine, and four times that of the SEER registry. All 15 patients treated with PVF were still alive 10 months after diagnosis, compared to only 71% for the MRV group, 69% for the no-vaccine group and only 45% for the SEER registry. Survival at 30 months for the PVF group was double that of both the MRV group and the no-vaccine group and almost 4 times that of the SEER registry.

The wilcoxon test shows a statistically significant survival difference between patients treated with PVF vaccine and both the MRV group (p=0.0246) and the no vaccine group (p=0.0433). This is remarkable considering the small size of the PVF group (n=15), indicative of substantial therapeutic effect. As evidenced by these results, the PVF composition, which contains *E. coli* the most common cause of bacterial infection of the colon, is an effective treatment for colon cancer.

Figure 9:
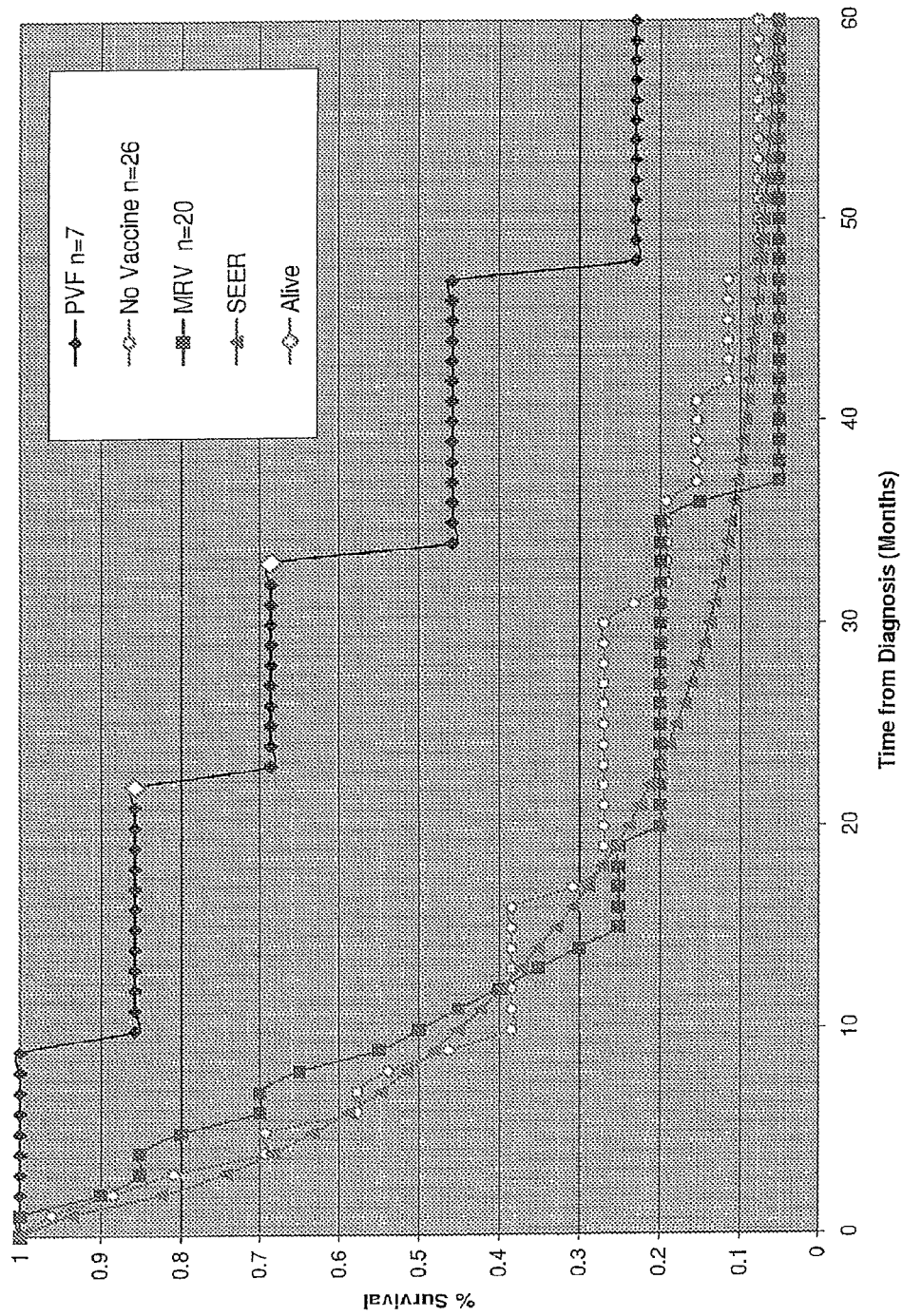
FIG. 9 shows a survival curve for a cumulative series of patients initially diagnosed with Stage 4 Colorectal Cancer, with date from patients receiving treatment within 3 months of diagnosis, comparing patients treated with PVF, patients treated with MRV, patients not treated with an antigenic composition and a standard SEER survival curve.

Survival of those patients who presented for immunological treatment in accordance with the invention within 3 months of diagnosis (i.e., excluding those patients who were long-term survivors before presenting for treatment) has also been analyzed. The results of this analysis are presented in FIG. 9. As illustrated, the 'MRV' and 'No Vaccine' survival curves in FIG. 9 are shifted substantially to the left (indicating that a selection bias towards 'long-term' survivors may have artifactually shifted these curves to the right in FIG. 8), whereas, remarkably, the PVF curve in FIG. 9 is actually further to the right than the curve in FIG. 8, indicating that the benefit of earlier treatment with PVF (i.e., within 3 months of diagnosis) more than outweighed any long-term survivor bias excluded in FIG. 9. This analysis provides compelling evidence that the benefit of PVF treatment for stage 4 colon cancer may be even greater than that illustrated in FIG. 8, and that the earlier the treatment with the compositions of the invention is begun following diagnosis, the greater the benefit.

In accordance with the foregoing results, one aspect of the invention involves the treatment of colon cancers with antigenic compositions that comprise antigenic determinants of microbial pathogens that are known to be colon pathogens, such as pathogens that are members of the endogenous flora of the colon or exogenous colonic pathogens. For example, antigenic determinants of the following microbial species may be used to treat primary and metastatic cancers situated in the colon: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica, Shigella flexneri*; adenoviruses, astroviruses, caliciviruses, noroviruses, rotaviruses, or cytomegalovirus. For example, cancers situated in the colon may be treated with the PVF composition, which contains *E. coli*, or alternative formulations that include only antigenic determinants of colonic pathogens. In selected embodiments, antigenic determinants of *E. coli*, the most common bacterial cause of colon infection, may be used alone or with antigenic determinants of other common pathogens of the colon to treat cancer of the colon.

EXAMPLE 1E

Use of Respivax, an Oral Vaccine to Treat Lung Cancer

Oral Respivax vaccine was administered as described above, with a dose of one 50 mg tablet per day, providing the equivalent of $1.25 \times 10^9$ cells of each species per dose. Patients were advised to continue the above dose for at least 6 months.

Figure 10:
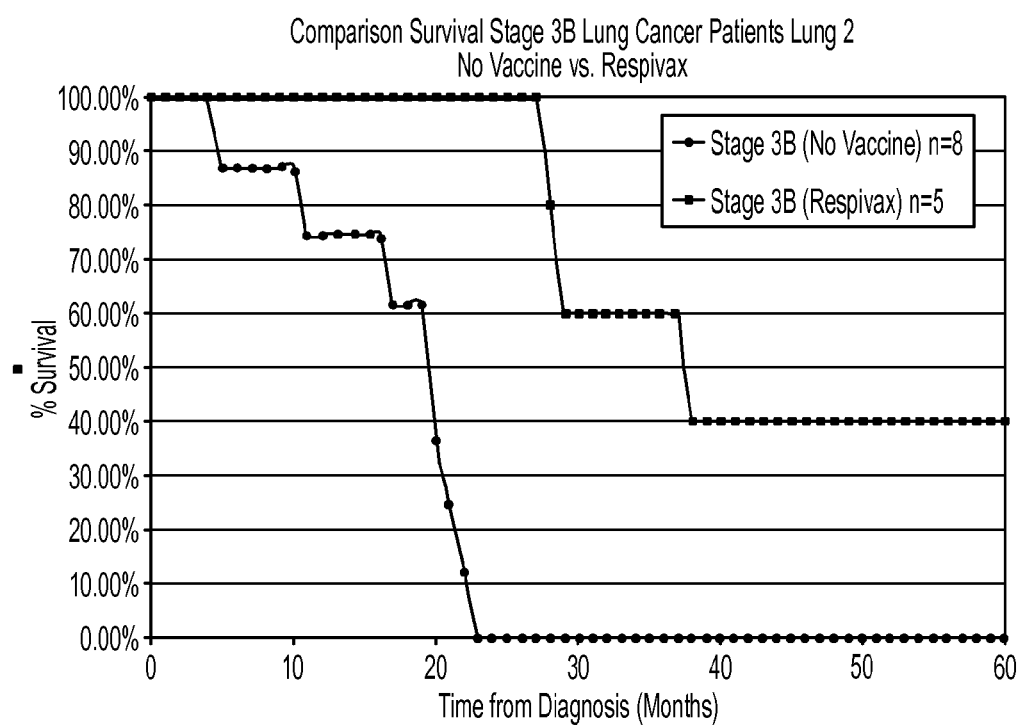
FIG. 10 shows a survival curve for a cumulative series of stage 3B lung cancer patients who were treated with an oral antigen therapy, Respivax, compared to patients who did not use an antigenic composition.

As illustrated in FIG. 10, survival of stage 3B lung cancer patients who were treated with the oral Respivax antigens was substantially better than patients who were not treated with the antigenic composition. Median survival was 37 months for the patients treated with Respivax, compared to only 20 months for those patients not treated with an antigenic composition vaccine. 40% of patients treated with Respivax were alive 5 years after diagnosis, whereas none of the untreated patients survived for more than 2 years.

In accordance with the foregoing results, one aspect of the invention involves the treatment of primary of the lung or metastases to the lung with oral administration of antigenic compositions that comprise antigenic determinants of microbial pathogens that commonly cause lung infection.

EXAMPLE 2

Case Reports

These case reports are indicative of the patients that make up the patient populations reflected in the foregoing cumulative studies, as well as illustrating additional aspects of the invention. In particular, the individual case reports of Patients A-N are illustrative of surprising results in some patients being treated with anti-inflammatories, while the case reports of Patients O-AA are representative of the general patient population that includes many examples of vaccine treatment that was effective in the absence of anti-inflammatory therapy.
MRV for Cancer of the Lund with and without Anti-Inflammatories Patient A (PtA): In September year 0, PtA developed right upper chest pain with an associated wheeze. These symptoms persisted and in January, year 1, she had a chest x-ray that revealed a large 7 cm×8 cm mass in the apex of the right lung. A fine needle aspiration was positive for non-small cell lung cancer. On January 27, year 1, an MRI showed invasion of the subclavian arteries, making surgical resection impossible and thus, PtA was diagnosed with stage 3B inoperable terminal lung cancer. She underwent a short course of palliative radiation and declined chemotherapy. She was told that she had terminal cancer with a 3 to 6 months life expectancy.

On April 29, year 1, PtA began therapy with MRV vaccine three times per week. On that same date she also began treatment with the non-steroidal anti-inflammatory agent (NSAID) indomethicin 50 mg four times per day and a regime of antioxidant supplements and vitamin D. 18 months later, by October, year 2, the tumour had markedly reduced in size to 3 cm in diameter and, by May 19, year 5, four years after starting treatment with the combined regime of MRV vaccine, indomethicin, antioxidants vitamins and vitamin D, only residual scarring remained. PtA continued treatment with this combination of MRV vaccine and adjuvant anti-inflammatory therapies for more than 4 years until the end of May, year 5 at which time there was no evidence of residual cancer, in spite of a diagnosis of terminal inoperable lung cancer more than 4 years previously. More than 14 years since diagnosis with terminal lung cancer, PtA continues to feel well with no evidence of residual cancer.

In accordance with the foregoing results, one aspect of the invention involves the treatment of cancers in the lung with administration of antigenic compositions that comprise antigenic determinants of microbial pathogens that commonly cause lung infection.

In accordance with the forgoing results, another aspect of the invention involves the administration of the immunogenic compositions repeatedly relatively frequently over a relatively long period of time.

The concomitant use of anti-inflammatory agents, such as antioxidants, vitamin D and indomethicin, in conjunction with targeted MRV therapy, was associated with substantially improved survival, which was greater than that of otherwise similar cases, in which these adjuvant anti-inflammatory modalities were not used in conjunction with the compositions of the invention. For example, Patient B, an otherwise similar case in which anti-inflammatories were not administered, was diagnosed with inoperable stage 3B non-small cell lung cancer, which was fatal within 3 months of diagnosis. These cases provide evidence of a synergistic effect between the antigenic compositions of the invention and anti-inflammatory treatments.

In accordance with the foregoing results, one aspect of the invention involves the treatment of cancers with both the administration of antigenic compositions that comprise antigenic determinants of microbial pathogens that are pathogenic to the organ or tissue targeted, as well as adjuvant anti-inflammatory treatments, for synergistic effect.
MRV for Cancer of the Lung with and without Anti-Inflammatories Patient C (PtC): In the spring of year 0, PtC began having pain in his right upper chest area. This pain persisted and on October 5, year 0 he had a chest x-ray that revealed a large 12 cm×11 cm mass occupying virtually the entire right upper lobe. A fine needle aspiration was positive for poorly differentiated non-small cell lung cancer. Exploratory thoracotomy was performed on December 7, year 0, which revealed tumour invasion of the chest wall and superior vena cava and therefore, PtC's tumour was inoperable (i.e., stage 3B).

PtC underwent a short course of palliative radiation and declined chemotherapy. He was told that he had terminal cancer with a 3 to 6 months life expectancy. By January 27, year 1, the rapidly growing tumour had increased in size to 14 cm×11.5 cm.

On February 9, year 1, PtC began treatment with indomethicin 50 mg four times per day, antioxidant vitamins, and vitamin D. Three weeks later, on March 1, year 1, PtC began treatment with MRV vaccine three times per week. By June, year 1, PtC was feeling well and was running 8 km 3-4 times per week. On June 4, year 1, a chest x-ray revealed that the tumour had reduced in size to 11 cm diameter. PtC continued to feel very well, leading a full and active life with return to full employment and continued full physical activity. PtC continued treatment with a combination of the MRV vaccine and adjuvant anti-inflammatory therapies (indomethicin, antioxidants and vitamin D) for more than 16 months until July 24, year 2, at which time indomethicin treatment was discontinued (as a result of decreased kidney function, a known potential side-effect of long-term indomethicin use). 6 months later, in December, year 2, after 22 months of targeted vaccine therapy, MRV treatment was discontinued (since MRV was no longer available past that date). PtC continued to feel well until June, year 6, at which time he was diagnosed with a recurrence of cancer in both lungs, which lead to his death on May 26, year 7, more than 6.5 years after he was diagnosed with terminal lung cancer and told he had 3-6 months to live.

In this case, the use of adjuvant anti-inflammatory agents, including antioxidants, vitamin D and indomethicin, used in conjunction with targeted MRV therapy for more than 16 months, was associated with substantially improved survival in the face of a diagnosis that is usually fatal within 1 year, which was greater than that of an otherwise similar case, Patient D, in which these adjuvant anti-inflammatory modalities were not used in conjunction with the compositions of the invention, and an inoperable lung cancer was fatal within 8 months of diagnosis. These cases provide evidence of a synergistic effect between the antigenic compositions of the invention and anti-inflammatory treatments.

PVF for Cancer of the Colon with Metastases to the Liver and Lung, and without Anti-Inflammatories Patient E (PtE): PtE had a surgical resection of colon cancer on June 17, year 0, followed by chemotherapy. On August 15, year 0, he was diagnosed stage 4 cancer with metastases to the liver and lungs, a diagnosis with a very poor prognosis. On October 20, year 0, PtE began treatment with an antioxidant and vitamin D regime and, on December 10, year 0, he began treatment with the PVF composition three times per week, which he has continued in combination with the antioxidants and vitamin D. In September, year 1, he began treatment with Celebrex™ 100 mg twice per day. In spite of a very poor initial prognosis, PtE was still and feeling well at last contact, more than 3 years after diagnosis with terminal metastatic colon cancer.

In accordance with the foregoing results, one aspect of the invention involves the treatment of cancers of the colon, liver and lung with administration of antigenic compositions that comprise antigenic determinants of microbial pathogens that are known to be pathogenic in the colon, liver and lung.

In contrast to PtE, of the 15 patients diagnosed with stage 4 colon cancer and treated with PVF, the patient with the shortest survival, Patient F, was not treated with anti-inflammatories. These cases provide compelling evidence that anti-inflammatory modalities (i.e., Celebrex™, anti-oxidants and vitamin D) taken in conjunction with targeted PVF therapy has a synergistic effect, contributing to PtE's prolonged survival, which was greater than that of otherwise similar cases in which these adjuvant anti-inflammatory modalities were not used in conjunction with the compositions of the invention.

PVF for Cancer of the Colon with Metastases to Lung, with Anti-Inflammatories

Patient G (PtG): PtG developed rectal bleeding in May, year 0, and was diagnosed with colon cancer. He underwent surgery, chemotherapy and radiation, but developed metastases to his lungs (stage 4 cancer) on 16 August, year 1, a terminal diagnosis with a poor prognosis. He had begun a regime of antioxidant vitamins and vitamin D in June, year 0, and, on September 23, year 1, he began taking the NSAID Celebrex 100 mg twice per day. In March, year 3, he began PVF vaccine three times per week, which he continued till April, year 4 at which time he developed brain metastases, which lead to his death on June 2, year 4, almost 3 years after a diagnosis of stage 4 terminal colon cancer. PtG lived substantially longer than would normally be expected with a diagnosis of stage 4 colon cancer with metastases to the lungs. In this context, the invention provides for the use of anti-inflammatory modalities in conjunction with immunogenic compositions, such as PVF, for synergistic effect.

Patient H (PtH): PtH was diagnosed with colon cancer with metastases to the liver and lungs on February 13, year 0. On January 11, year 1, he was prescribed an antioxidant and vitamin D regime. However, in March, year 1, he entered a chemotherapy research study and discontinued these supplements at that time at the request of the study coordinators. He was not treated with any NSAIDs. On May 12, year 1, he began treatment with PVF, which he took three times per week until his death just 2.5 months later. When contrasted to similar cases that involved the use of anti-infammatories, this case illustrates that, if adjuvant anti-inflammatory modalities are not given concomitantly with the targeted antigenic activation therapy, there is a lack of a synergistic effect that would otherwise occur with concomitant use of adjuvant anti-inflammatory modalities.

In summary, in cases of stage 4 colon cancer treated with targeted PVF vaccine therapy, the use of adjuvant anti-inflammatory agents, including antioxidants, vitamin D and Celebrex, used in conjunction with targeted antigenic activation therapy, was associated with substantially improved survival, much greater than that of the two cases in which these adjuvant anti-inflammatory modalities were not used in conjunction with the vaccine, providing evidence suggestive of a synergistic effect.

PVF with and without Anti-Inflammatories for Cancer of the Pancreas with Metastases to the Lungs, Liver and Abdominal Lymph Nodes Patient I (PtI): PtI was diagnosed with pancreatic cancer in August, year 1, at which time he had surgery to remove his pancreas (i.e., Whipple's procedure). However, in July year 2, he developed metastases to the lungs bilaterally and in February year 4 he developed recurrence of cancer in the pancreatic area with abdominal and liver metastases. This is a terminal diagnosis with a very poor prognosis. PtI began a regime of antioxidant vitamins, vitamin D, large doses of turmeric (curcumin), fish oil (9 gm per day), resveratrol and green tea (equivalent of 36 cups per day) on September 27, year 2, all of which are anti-inflammatory modalities, all of which he continued to take. In March year 3, he began treatment with Celebrex 100 mg twice per day, which he took for more than 20 months. PtI began treatment with PVF three times per week in May year 4, which he has continued to use regularly for more than 3 years. PtI survived for 5 years after a diagnosis of terminal metastatic pancreatic cancer, a remarkably prolonged survival in the context of a diagnosis that has an extremely poor prognosis. This case provides evidence that high doses of multiple anti-inflammatory modalities (i.e., Celebrex, antioxidants, vitamin D, turmeric, fish oil, resveratrol, green tea) taken in conjunction with the PVF compositions, resulted in a synergistic effect which has contributed to PtI's remarkable survival for 5 years after developing metastatic pancreatic cancer, a diagnosis that is usually fatal within 6 months.

In accordance with the foregoing results, one aspect of the invention involves the treatment of cancer of the pancreas, abdominal lymph nodes, liver and lung with administration of antigenic compositions that comprise antigenic determinants of microbial pathogens that are known to cause infection in the pancreas, abdominal lymph nodes, liver and lungs.

Patient J (PtJ) had an essentially identical diagnoses to PtI (i.e., pancreatic cancer with metastases to abdominal lymph nodes, lungs and liver). PtJ, who did not take any other anti-inflammatories along with the PVF vaccine except antioxidants and vitamin D, died within 4 months of diagnosis, whereas PtI, who took large doses of numerous other anti-inflammatories modalities (i.e., Celebrex, turmeric, fish oil, resveratrol and green tea) in conjunction with PVF vaccine, survived for 5 years after diagnosis. These cases provide evidence of a synergistic effect of high dose multiple anti-inflammatory modalities and targeted vaccine therapy.

MRV for Cancer of the Breast with Metastases to the Bone

Patient K (PtK): In March, year 0, PtK developed neck and back pain, which persisted. On July 28, year 0, she was diagnosed with stage 4 breast cancer with metastases to the cervical spine, an incurable diagnosis. She underwent surgery to remove two breast lumps (axillary lymph nodes positive) and palliative radiation to the metastases in her spine. On January 18, year 1, PtK began treatment with doses of anti-oxidants and vitamin D, as well as the NSAID indomethicin 50 mg four times per day. Three days later, on January 21, year 1, she began treatment with the MRV composition, which contains *Staphylococcus aureus* the most common pathogen of both the breast and bone. Although there was no documentation of the exact length of time that treatment with this combination of MRV/indomethicin/antioxidant/vitamin D was continued, the patient was given sufficient vaccine (20 ml) for approximately 2 years of treatment at the usual dose and frequency (i.e., three times per week) and PtK stated that she completed the recommended treatment course at home. Remarkably, PtK was still alive at last contact, 13 years after diagnosis with stage 4 metastatic breast cancer with metastases to bone.

In accordance with the foregoing results, one aspect of the invention involves the treatment of cancers of the breast and bone with administration of antigenic compositions that comprise antigenic determinants of microbial pathogens that are known to be pathogenic in the breast and bone infection.

In contrast to Patient K, Patient L (PtL) was diagnosed with breast cancer with metastases to bone on October 11, year 0. She was not prescribed an NSAID or other anti-inflammatories. PtL began treatment with MRV on February 27, year 1. She died 9 months later on November 4, year 1, just over one year after diagnosis with stage 4 breast cancer with metastases to bone. The contrast between the otherwise similar cases of PtK and PtL illustrates the potential for synergistic treatment with anti-inflammatories and the antigenic compositions of the invention.

MRV with and without Anti-Inflammatories for Cancer of the Breast with Metastases to the Bone Patient M (PtM): PtM was diagnosed with stage 4 breast cancer with metastases to bone on June 15, year 0. She began on the NSAID Naprosyn 250 mg twice per day on an ongoing basis for pain relief and, in October, year 3, she began doses of antioxidants and vitamin D. Three months later, on January 15, year 4, she began treatment with MRV vaccine (which contains *Staphylococcus aureus*, the most common breast and bone pathogen) in combination with these anti-inflammatory therapies (i.e., Naprosyn, antioxidants and vitamin D). PtM lived for more than 9 years after being first diagnosed with stage 4 metastatic breast cancer with metastases to bone, an unusually long survival considering the usual poor prognosis associated with this diagnosis.

In accordance with the foregoing results, one aspect of the invention involves the treatment of cancers of the breast and bone with administration of antigenic compositions that comprise antigenic determinants of microbial pathogens that are known to be common causes of breast and bone infection.

In contrast to PtM, Patient N (PtN): PtN was diagnosed with stage 4 cancer with metastases to bone on April 8, year 0. She began doses of antioxidants and vitamin D on April 24, year 0. However, prior to starting MRV, she was prescribed the blood thinner warfarin, limiting supplementation with vitamin E and vitamin C, two important antioxidants that can lead to potential complications if used in conjunction with warfarin. In addition, NSAIDs could not be prescribed in this case since they are contraindicated with warfarin use. On June 2, year 1 PtN began treatment with MRV. She died 14 months later in August, year 2. In this context, it is possible that the use of targeted vaccine therapy without the synergistic effect of adjuvant anti-inflammatories (i.e., NSAID, vitamin E and therapeutic doses of vitamin C) limited its potential benefit.

In summary, in the cases of stage 4 breast cancer with metastases to the bone treated with targeted MRV therapy detailed above, the use of adjuvant anti-inflammatory agents in conjunction with MRV was associated with substantially improved survival, much greater than that of the two cases in which these adjuvant anti-inflammatory modalities were not used in conjunction with the vaccine, providing evidence suggestive of a synergistic effect.

MRV for Metastases to the Lungs

Patient O (PtO) was diagnosed in June, year 0 with kidney cancer with metastases to the lungs bilaterally and to the bone (left femur). This is generally considered to be an incurable terminal diagnosis with a poor prognosis. He began treatment with the MRV on August 10, year 0 and continued regular treatment (three times per week) for 16 months (after which MRV was no longer available). In September, year 0, he began 7 months of treatment with an experimental drug, pegylated interferon alpha-2a. His left femur was 'pinned' due to the risk of fracture as a result of the metastasis but, due to surgical complications, amputation of the left leg below the mid-thigh was required. In September, year 2, his cancerous right kidney was removed. In October, year 2, a PET scan found no evidence of cancer in the lungs and no further evidence of bone metastases. PtO is alive with no evidence of cancer in his lungs, more than 9 years after a diagnosis of bilateral pulmonary metastases, a remarkable result.

In accordance with the foregoing results, one aspect of the invention involves the treatment of metastases to the lung with administration of antigenic compositions that comprise antigenic determinants of microbial pathogens that are known to be lung pathogens.

MRV for Metastases to the Bone and Lungs

Patient P (PtP) was diagnosed with kidney cancer in July, year 0, and underwent excision of this right kidney. In December, year 4, he developed metastases to the bone (femurs bilaterally) and lungs (bilaterally). PtP declined conventional treatment and began treatment with MRV in April, year 5, which he continued regularly, three times per week, for 18 months. PtP's health improved and he returned to normal daily activities. X-rays and imaging of the chest and femurs showed no progression, with stable disease in the lungs and femurs during the 18 months that PtP was on MRV treatment.

In accordance with the foregoing results, one aspect of the invention involves the treatment of metastases to the lung and bone with administration of antigenic compositions that comprise antigenic determinants of microbial pathogens that are common causes of lung and bone infection.

MRV for Metastases to the Lungs

Patient Q (PtQ) was diagnosed with colon cancer with probable metastases to the lungs in June, year 0. At that time, the primary colon tumour was fully excised, leaving only several lung metastases. PtQ started treatment with MRV on December 11, year 0 which she continued three times per week for 4 months. On April 19, year 1, after 6 months treatment with chemotherapy, she had surgery to excise the only visible lung lesion remaining, which was confirmed to be a metastatic lesion. A diagnosis of colon cancer with lung metastases has a poor prognosis, even in the context of chemotherapy followed by surgery to excise visible metastases. In spite of her original poor prognosis, PtQ remains in excellent health, with no evidence of cancer more than 10 years after her initial diagnosis with metastases to the lung and treatment with MRV.

S. aureus Antigens for Breast Cancer with Metastasis to the Bone

Patient R (PtR): In May, year 0, PtR was diagnosed with breast cancer with metastases to her sternum, femur and cervical spine, an incurable cancer with a poor prognosis. She was treated with radiation and Tamoxefen. In May, year 4, she developed an additional area of metastasis in her lumbar spine and she began on treatment with Megace. In November, year 4, she began treatment with a vaccine (Staphage Lystate vaccine) containing only Staphylococcus aureus, the most common cause of infection of both the breast and bone and thus, a selected formulation for the treatment of breast and bone cancer. She continued regular therapy with this vaccine for 5 years. In spite of a diagnosis of metastatic breast cancer with multiple bone metastases, PtR survived for more than 17 years, a remarkable survival in the context of incurable metastatic breast cancer and a testament to the promise of targeted vaccine therapy for the treatment of breast cancer.

In accordance with the foregoing results, one aspect of the invention involves the treatment of cancers of the breast and bone with administration of antigenic compositions that comprise antigenic determinants of microbial pathogens that are known to be the most common cause of the breast and bone infection.

This embodiment illustates that a formulation that includes antigenic determinants of only the most frequently pathogenic organism or organisms for a tissue may provide particular advantages, as is also illustrated in the mouse model data set out below. In keeping with this, we have found enhanced effectiveness of Respivax as opposed to MRV in treating cancers situated in the lung, reflecting the fact that the Respivax formulation is somewhat more optimal because it includes higher relative concentrations of the pathogenic species which most commonly cause lung infection (i.e., 67% of the bacterial cell count of Respivax is comprised of species that most commonly cause lung infection, whereas only 30% of the MRV vaccines are comprised of species that most commonly cause lung infection).

In accordance with the foregoing results, one aspect of the invention involves formulating the antigenic compositions such that antigenic determinants of microbial pathogens that are known to be the common causes of infection are given preferential priority in the proportions of the formulation, with the most common cause of infection receiving the greatest preferential priority. For example, the proportion of antigenic determinants that are derived from pathogens that are known to be a common cause of infection may be 10, 20, 30, 40, 50, 60, 70, 80, 90, 95 or 100%.

Accordingly, in some embodiments, the invention provides antigenic compositions in which a threshold proportion of antigenic determinants selected in accordance with the invention are used, relative to any other antigenic determinants in the composition. For example, antigenic compositions may have greater than X % of the antigenic determinants therein derived from pathogenic (or commonly pathogenic, or most commonly pathogenic) species, where X may for example be 10, 20, 30, 40, 50, 60, 70, 80, 90, 95 or 100 (or any integer value between 10 and 100). For example, at least X % of the antigenic determinants in the antigenic composition may be specific for microbial pathogens that are pathogenic (or commonly pathogenic, or most commonly pathogenic) in the specific organ or tissue of the patient within which the cancer is situated. Using an alternative measure, of the total number of microbial pathogens in the antigenic composition, at least X % may be selected to be microbial pathogens that are pathogenic (or commonly pathogenic, or most commonly pathogenic) in the specific organ or tissue of the patient within which the cancer is situated. In some embodiments, the antigenic composition may accordingly consist essentially of antigenic determinants of one or more microbial pathogens that are each pathogenic in the specific organ or tissue within which the cancer is situated. In selected embodiments, the antigenic composition may consist essentially or entirely of antigenic determinants of microbial pathogens that are commonly pathogenic in the specific organ or tissue of the patients with which the cancer is situated. In further selected embodiments, the antigenic antigenic composition may consist essentially or entirely of antigenic determinants of a microbial pathogen (or pathogens) that are most commonly pathogenic in the specific organ or tissue of the patients with which the cancer is situated.

In the context of various aspects of the invention, organisms are characterized by the frequency with which they are pathogenic. In this context, the invention also relates to the frequency with which endogenous flora are pathogenic. For clarity, in this regard, the characterizations herein of the frequency of pathogenicity, such as the designation "commonly pathogenic" relate, in general, to the proportion of infections in a particular organ or tissue that are commonly attributed to a particular organism, and not to the frequency with which microbial colonization of a tissue is converted to a pathogenic infection. In North America, the majority of human infections are understood to be caused by endogenous organisms, even though these organisms commonly are present as part of the endogenous flora without causing infection. For example, while S. pneumonia is a common cause of lung infection (i.e., pneumonia) in humans (and thus, is designated "commonly pathogenic" in the lung), it is nevertheless also true that S. pneumonia is commonly present as part of the endogenous flora of the respiratory tract without causing infection and thus, in the nature of an endogenous colonization, is not normally pathogenic.

MRV for Multiple Myeloma

Patient S (PtS) was diagnosed with multiple myeloma (stage 3A) in the fall of year 0, with multiple lesions on bone scan, including skull, humeri and pelvis. He was treated with standard chemotherapy (melphalan and prednisone) for 6 months. However, in December year 3, he developed a pathological fracture of his right femur as a result of his disease, which required pinning and local radiation. On April 28, year 4, PtS began treatment with MRV, which contains Staphylo-

*coccus aureus* a common cause of septicemia, which he continued for more than 13 years until this vaccine was no longer available in December year 17. Remarkably, PtS is still alive almost 25 years after being diagnosed with multiple myeloma, a truly extraordinary outcome considering his 'terminal' diagnosis.

In accordance with the foregoing results, one aspect of the invention involves the treatment of hematological cancers with administration of antigenic compositions that comprise antigenic determinants of microbial pathogens that are known to cause septicemia.

In accordance with the forgoing results, and as illustrated in other patient case reports detailed herein, another aspect of the invention involves the administration of the immunogenic compositions repeatedly relatively frequently over a relatively long period of time, as described elsewhere herein.

PVF for Colon Cancer with Metastases of the Liver and Abdominal Lymph Nodes

Patient T (PtT) was diagnosed with colon cancer and was treated with excision of the primary tumour (and subsequent chemotherapy) in September year 0. Ten months later, she developed a liver metastasis, which was surgically excised in July year 1. PtT remained well until June year 7, when she was diagnosed with recurrent disease—an inoperable mass of abdominal lymph nodes in close proximity to the aorta and spine, obstructing her left ureter, requiring insertion of a nephrostomy tube. PtT was considered terminal and treated with palliative radiation in October year 7. She began treatment with PVF on November 17, year 7, which she continued every second day. PtT survived for almost 4 years after being diagnosed with terminal recurrent metastatic colon cancer.

In accordance with the foregoing results, one aspect of the invention involves the treatment of cancer in abdominal lymph nodes with administration of antigenic compositions that comprise antigenic determinants of microbial pathogens that are known to cause infection in abdominal lymph nodes.

MRV for Metastasis to the Skin and Perineum

Patient U (PtU) was diagnosed with colon cancer and was treated with excision of the primary tumour in November year 0. He was diagnosed with stage 4 cancer in July year 2 with metastases to the perineum (i.e., peri-anal/genital soft tissue area) and skin. He had further surgery to remove as much of the cancer as possible in the perineum (cancer extended past surgical margins) with follow-up radiation and chemotherapy. The only known cancer sites remaining were in the skin and perineum. PtU started treatment with MRV, which contains *Staphylococcus aureus* a common cause of skin and perineal infection, on May 25, year 3, which he continued three times per week for 5 months. In spite of his original poor prognosis, PtU is in excellent health more than 10 years after his diagnosis with stage 4 cancer with metastases to the perineum and skin.

In accordance with the foregoing results, one aspect of the invention involves the treatment of cancer of the skin and perineum with administration of antigenic compositions that comprise antigenic determinants of microbial pathogens that are known to be common causes infection in the skin and perineum.

PVF for Metastases to the Peritoneum

Patient V (PtV) was diagnosed with breast cancer in May, year 0, at which time she had a masectomy with adjuvant chemotherapy. In January, year 12, she developed abdominal pain and ascites and was diagnosed with peritoneal metastases, a diagnosis with a poor prognosis. On August 5, year 12, PtV began treatment with PVF, which contains *E. coli* a common cause of peritoneal infection, which she continued regularly for 1 year. Her tumour markers and ascites decreased and, in August year 13, after one year of PVF treatment, she had abdominal surgery for an unrelated medical condition, at which time the surgeon could not find any evidence of the previous peritoneal cancer. PtV discontinued use of the vaccine. PtV was still alive at last contact, 3 years and 9 months after being diagnosed with terminal peritoneal metastases.

In accordance with the foregoing results, one aspect of the invention involves the treatment of peritoneal metastases with administration of antigenic compositions that comprise antigenic determinants of microbial pathogens that are known to cause peritoneal infection.

PVF for Ovarian and Pelvic Cancer

Patient W (PtW) was diagnosed with stage 3B poorly differentiated ovarian cancer in the fall of year 0. She had surgery in November year 0, with removal of the left ovary, but the cancer could not be completely excised and thus, she was at extreme risk for recurrence. She had a full course of postoperative chemotherapy. However, in year 2 her tumour markers began to rise and in January year 3 she was diagnosed with a recurrence in her right ovary area. She had surgery to remove this right ovarian mass in February year 3, but again the cancer could not be completely excised and she had follow-up chemotherapy. However, once again in December year 3 she developed a further recurrence in the pelvic area and retroperitoneal lymphadenopathy. She began treatment with PVF vaccine, which contains *E. coli* a cause of ovarian and pelvic infection, on January 5, year 4, which she continued for 6 months. Her tumour markers, which had risen to 2600, fell to the 300 range. PtW was alive and feeling very well at last contact, 2 years and 9 months after being diagnosed with recurrent ovarian cancer. Of note is the fall in her tumour markers following PVF treatment.

In accordance with the foregoing results, one aspect of the invention involves the treatment of ovarian and pelvic cancer with administration of antigenic compositions that comprise antigenic determinants of microbial pathogens that are known to cause infection in the ovary and pelvic areas.

MRV for Follicular Non-Hodgkin's Lymphoma

Patient Y (PtY): was diagnosed with stage 4A Follicular Non-Hodgkin's lymphoma, with extensive marked lymphadenopathy (i.e., enlarged lymph glands). He declined all conventional treatment. PtY began treatment with the MRV composition, which contains many of the pathogens which commonly cause infection of the lymph nodes of the head and neck, axillae, mediastinum and inguinal areas. In addition, he began treatment with a multiple vitamin/supplement regime, healthful diet and other immune enhancement treatments. He continued regular use of this vaccine for more than 3 years, at which time his lymph glands had begun to greatly reduce in size and he was feeling well. This resolution of lymphadenopathy continued, and imaging showed almost complete resolution of previous extensive lymphadenopathy. PtY was feeling well and there was no lymphadenopathy palpable: a clearly remarkable recovery. Five years after his initial diagnosis with Stage 4A Follicular Non-Hodgkin's lymphoma, PtY had no evidence of recurrence and was leading an active and healthy life. Treatment with MRV vaccine resulted in complete remission of his stage 4A follicular non-Hodgkins' lymphoma.

In accordance with the foregoing results, one aspect of the invention involves the treatment of lymphoma with administration of antigenic compositions that comprise antigenic determinants of microbial pathogens that are known to be common causes of lymph node infection in the region the lymphoma is located.

PVF for Colon Cancer with Metastases to the Liver and Kidneys

Patient Z (PtZ) was diagnosed with metastatic spread of previously treated colon cancer, with a metastasis to the liver and probable other metastases to both kidneys. The liver metastasis was excised. The prognosis for this stage (i.e., stage 4) of colon cancer is poor and the benefit of further conventional treatment (i.e., chemotherapy) is limited. PtZ declined chemotherapy initially. Three months after diagnosis with metastatic colon cancer, PtZ began treatment with Polyvaccinum Forte (PVF), which contains E. coli, a common cause of infection of the colon, liver and kidneys. In addition PtZ began treatment with a multiple vitamin/supplement regime and healthful diet. He continued regular use of this vaccine and the vitamin and supplement regime, and began chemotherapy. Although the overall course of his disease was slowly progressive, with development of lung metastases and recurrence of liver metastases, 28 months after his initial diagnosis of metastatic disease, his weight was stable and his energy levels were good. Three years (36 months) after diagnosis of stage 4 colon cancer, PtZ was feeling well except for nausea and mild weight loss related to chemotherapy.

In accordance with the foregoing results, one aspect of the invention involves the treatment of cancer of the colon, liver and kidneys with administration of antigenic compositions that comprise antigenic determinants of microbial pathogens that are known to be pathogenic in the colon, liver and kidneys.

PVF for Colon Cancer with Metastases to the Liver, Porta Hepatic Lymph Nodes and Lung Patient AA (PtAA) was diagnosed with metastatic colon cancer with metastases to the liver, portahepatic lymph nodes and lungs. The prognosis for this stage (i.e., stage 4) of colon cancer is very poor (i.e., 'terminal' cancer) and the benefit of conventional treatment (i.e., chemotherapy) is limited. PtAA began chemotherapy, but discontinued treatment approximately 5 months after his diagnosis due to side effects, at which time he began treatment with Polyvaccinum Forte (containing bacterial species which cause infection in the colon, liver, abdominal lymph nodes and lungs) every second day as well as a multiple vitamin/supplement regime and a healthy diet. PtAA's subsequent CT Scans demonstrated necrotic porta hepatic lymph nodes unchanged in size from the time of his diagnosis and no change in size of the lung metastases, although the two liver metastases grew moderately in size (3.4 cm to 4.5 cm and 1.2 cm to 3.0 cm). In spite of the very poor prognosis, PtAA continued to feel quite well almost one year after a diagnosis of terminal cancer.

In accordance with the foregoing results, one aspect of the invention involves the treatment of cancer of the colon, liver, abdominal lymph nodes and lungs with administration of antigenic compositions that comprise antigenic determinants of microbial pathogens that are known to be pathogenic in the colon, liver, abdominal lymph nodes and lungs.

EXAMPLE 3

Microbial Pathogens

In alternative aspects, the invention utilizes microbial antigens, such as bacterial or viral antigens, to formulate antigenic compositions, where the microbial species is selected on the basis of the tissue or organ within which the microbe is known to cause infections. Bacterial resident flora are the most common bacterial pathogens, accounting for the vast majority of bacterial infections in most animals, including humans. Resident flora can for example infect through primary attachment, or attachment and invasion following mucosa damage, resulting for example from vascular, trauma, chemical insult, or damage resulting from primary infection.

For microbial pathogens, virulence and infection potential is a combination of the ability of the microbe to adhere, to produce enzymes, to survive immunoproducts (complement, antibody) and to survive the microbiocidal activity of macrophage and neutrophils. Some bacteria, including endogenous bacteria, may be sufficiently virulent as to cause monomicrobial infections, while others are more effective with the synergy of polymicrobial infection. In general, it is often not possible to be precise about the specific role of individual microbes within the milieu of mixed infection. As acute infection may, in some cases, provide more optimal immune stimulation, accordingly, in some embodiments, the invention utilizes microbial species that are involved in acute infection.

In some embodiments, bacteria that are members of the endogenous flora of a particular region may be used to formulate antigenic compositions of the invention. The rows of Table 1 list a number of bacterial species, together with the biological regions in which each species may form a part of the endogenous flora. For example, *Abiotrophia* spp. are typically members of the endogenous flora of the respiratory tract and the mouth.

TABLE 1

Human Bacterial Normal Flora (Endogenous Bacterial Human Pathogens)

| Bacterial species | Respiratory | Mouth | Stomach | Duodenum/Jejunum | Ileum | Colon | GU System | Genital | Skin |
|---|---|---|---|---|---|---|---|---|---|
| CFL/mL | | $10^5$ | $10^2$ | $10^5$ | $10^8$ | $10^{11}$ | | | |
| *Abiotrophia* spp | + | + | | | | | | | |
| *Acholeplasma laidlawii* | + | + | | | | | | | |
| *Acidaminococcus fermentans* | + | + | | | + | + | + | | |
| *Acinetobacter* spp. | + | + | | | + | + | + | + | + |
| *Actinobacillus* spp. | + | + | | | | | | | |
| *Actinobaculum* spp. | + | + | | | + | + | + | | |
| *Actinomyces* spp. | + | + | | | + | + | + | + | |
| *Aerococcus christensenii* | | | | | | | + | | |
| *Aerococcus viridans* | | | | | | | | | + |
| *Aerococcus urinae* | | | | | | | + | | |
| *Aeromonas* spp. | | | | + | + | + | | | |

TABLE 1-continued

Human Bacterial Normal Flora (Endogenous Bacterial Human Pathogens)

| Bacterial species | Respiratory | Mouth | Stomach | Duodenum/Jejunum | Ileum | Colon | GU System | Genital | Skin |
|---|---|---|---|---|---|---|---|---|---|
| *Alloiococcus otitis* | | | | | | | | | + |
| *Anaerorhabdus furcosus* | | | | | + | + | | | |
| *Anaerococcus hydrogenalis* | | | | | + | + | + | | + |
| *Anaerococcus lactolyticus* | | | | | + | + | + | | |
| *Anaerococcus prevotii* | | | | | + | + | + | | |
| *Arcanobacterium* spp. | + | | | | | | | | + |
| *Atopobium* spp. | + | + | | + | + | + | | | |
| *Bacillus* spp. | | | | | + | + | | | + |
| *Bacteroides caccae* | | | | | + | + | | | |
| *Bacteroides distasonis* | | | | | + | + | | | |
| *Bacteroides eggerthii* | | | | | + | + | | | |
| *Bacteroides fragilis* | | | | | + | + | + | + | |
| *Bacteroides merdae* | | | | | + | + | | | |
| *Bacteroides ovatus* | | | | | + | + | | | |
| *Bacteroides splanchnicus* | | | | | + | + | | | |
| *Bacteroides thetaiotaomicron* | | | | | + | + | | | |
| *Bacteroides vulgatus* | | | | | + | + | | | |
| *Bifidobacterium adolescentis* | | | | + | + | + | | | |
| *Bifidobacterium bifidum* | | | | + | + | + | + | + | |
| *Bifidobacterium breve* | | | | + | + | + | + | + | |
| *Bifidobacterium catenulatum* | | | | + | + | + | + | + | |
| *Bifidobacterium dentium* | + | + | | + | + | + | + | + | |
| *Bifidobacterium longum* | | | | + | + | + | + | + | |
| *Bilophila wadsworthia* | + | + | | + | + | + | + | + | |
| *Brevibacterium casei* | | | | | | | | | + |
| *Brevibacterium epidermidis* | | | | | | | | | + |
| *Burkholderia cepacia* | + | | | + | + | + | | | |
| *Butyrivibrio fibrisolvens* | | | | + | + | + | | | |
| *Campylobacter concisus* | + | | | + | + | + | | | |
| *Campylobacter curvus* | + | | | + | + | + | | | |
| *Campylobacter gracilis* | + | | | + | + | + | | | |
| *Campylobacter jejuni* | | | | + | + | + | | | |
| *Campylobacter rectus* | | | | + | + | + | | | |
| *Campylobacter showae* | + | + | | + | + | + | | | |
| *Campylobacter sputorum* | + | + | | | | | | | |
| *Capnocytophaga granulosum* | + | + | | | | | | | |
| *Capnocytophaga gingivalis* | + | + | | | | | | | |
| *Campylobacter haemolytica* | + | + | | | | | | | |
| *Capnocytophaga ochracea* | + | + | | + | + | + | + | + | |
| *Capnocytophaga sputigena* | + | + | | | | | | | |
| *Cardiobacterium hominis* | + | + | | | | | | | |
| *Cedecea* spp | | | | | | + | | | |
| *Centipeda periodontii* | + | + | | | | | | | |
| *Citrobacter freundii* | | | | + | + | + | | | |
| *Citrobacter koseri* | | | | + | + | + | | | |
| *Clostridium* spp. | | | | + | + | + | | | |

TABLE 1-continued

Human Bacterial Normal Flora (Endogenous Bacterial Human Pathogens)

| Bacterial species | Respiratory | Mouth | Stomach | Duodenum/Jejunum | Ileum | Colon | GU System | Genital | Skin |
|---|---|---|---|---|---|---|---|---|---|
| *Corynebacterium accolens* | + | + | | | | | | | + |
| *Corynebacterium afermentans* | + | + | | | | | | | + |
| *Corynebacterium amycolatum* | | | | | | | | | + |
| *Corynebacterium auris* | | | | | | | | | + |
| *Corynebacterium diphtheriae* | + | | | | | | | | + |
| *Corynebacterium durum* | | + | | | | | | | |
| *Corynebacterium glucuronolyticum* | | | | | | | + | | |
| *Corynebacterium jeikeium* | | | | | | | | | + |
| *Corynebacterium macginleyi* | | | | | | | | | + |
| *Corynebacterium matruchotii* | | + | | | | | | | |
| *Corynebacterium minutissimum* | | | | | | | | | + |
| *Corynebacterium propinquum* | | + | | | | | | | |
| *Corynebacterium pseudodiphtheriticum* | | + | | | | | | | |
| *Corynebacterium riegelii* | | | | | | | + | | |
| *Corynebacterium simulans* | | | | | | | | | + |
| *Corynebacterium striatum* | | + | | | | | | | + |
| *Corynebacterium ulcerans* | | + | | | | | | | |
| *Corynebacterium urealyticum* | | | | | | | + | | + |
| *Dermabacter hominis* | | | | | | | | | + |
| *Dermacoccus nishinomiyaensis* | | | | | | | | | + |
| *Desulfomonas pigra* | | | | + | + | + | | | |
| *Dysgonomonas* spp. | | | | + | + | + | | | |
| *Eikenella corrodens* | + | + | | + | + | + | | | |
| *Enterobacter aerogenes* | | | | + | + | + | | | |
| *Enterobacter cloacae* | | | | + | + | + | | | |
| *Enterobacter gergoviae* | | | | + | + | + | | | |
| *Enterobacter sakazakii* | | | | + | + | + | | | |
| *Enterobacter taylorae* | | | | + | + | + | | | |
| *Enterococcus* spp. | | | | + | + | + | | | |
| *Escherichia coli* | | | | + | + | + | + | + | |
| *Escherichia fergusonii* | | | | + | + | + | | | |
| *Escherichia hermannii* | | | | + | + | + | | | |
| *Escherichia vulneris* | | | | + | + | + | | | |
| *Eubacterium* spp. | + | + | | + | + | + | | | |
| *Ewingella americana* | + | + | | | | | | | |
| *Finegoldia magnus* | | | | + | + | + | + | | + |
| *Fusobacterium alocis* | + | + | | | | | | | |
| *Fusobacterium gonidiaformans* | | | | + | + | + | + | + | |
| *Fusobacterium mortiferum* | | | | + | + | + | | | |
| *Fusobacterium naviforme* | | | | + | + | + | + | + | |
| *Fusobacterium necrophorum* | + | + | | + | + | + | | | |
| *Fusobacterium nucleatum* | + | + | | | | | | | |
| *Fusobacterium sulci* | + | + | | | | | | | |
| *Fusobacterium russii* | | | | + | + | + | | | |

TABLE 1-continued

Human Bacterial Normal Flora (Endogenous Bacterial Human Pathogens)

| Bacterial species | Respiratory | Mouth | Stomach | Duodenum/ Jejunum | Ileum | Colon | GU System | Genital | Skin |
|---|---|---|---|---|---|---|---|---|---|
| *Fusobacterium varium* | | | | + | + | + | | | |
| *Gardnerella vaginalis* | | | | + | + | + | + | + | |
| *Gemella haemolysans* | + | + | | | | | | | |
| *Gemella morbillorum* | + | + | | + | + | + | | | |
| *Globicatella* spp. | | + | | | | + | | | |
| *Granulicatella* spp. | + | + | | | | | | | |
| *Haemophilus* spp. | + | + | | | | | | + | |
| *Hafnia alvei* | | | | + | + | + | | | |
| *Helcococcus kunzii* | | | | | | | | | + |
| *Helicobacter* spp. | | | | + | + | + | | | |
| *Kingella* spp. | + | + | | | | | | | |
| *Klebsiella* spp. | + | + | | + | + | + | | | |
| *Kocuria* spp. | | | | | | | | | + |
| *Kytococcus sedentarius* | | | | | | | | | + |
| *Lactobacillus acidophilus* | + | + | + | + | + | + | + | + | |
| *Lactobacillus breve* | + | + | | | | | | | |
| *Lactobacillus casei* | + | + | | | | | + | + | |
| *Lactobacillus cellobiosus* | | | | | | | + | + | |
| *Lactobacillus fermentum* | + | + | + | + | + | + | + | + | |
| *Lactobacillus reuteri* | | | | + | + | + | + | | |
| *Lactobacillus salivarius* | + | + | + | + | + | + | | | |
| *Lactococcus* spp. | | | | | | | + | + | |
| *Leclercia adecarboxylata* | | | | + | + | + | | | |
| *Leminorella* spp. | | | | + | + | + | | | |
| *Leptotrichia buccalis* | + | + | | | | | + | + | |
| *Leuconostoc* spp. | | | | | | | + | + | |
| *Megasphaera elsdenii* | | | | + | + | + | | | |
| *Micrococcus luteus* | + | + | | | | | | | + |
| *Micrococcus lylae* | + | + | | | | | | | + |
| *Micromonas micros* | + | + | | | | | | | |
| *Mitsuokella multiacidus* | | | | + | + | + | | | |
| *Mobiluncus curisii* | | | | + | + | + | | + | |
| *Mobiluncus mulieris* | | | | + | + | + | | + | |
| *Moellerella wisconsensis* | | | | + | + | + | | | |
| *Moraxella catarrhalis* | + | + | | | | | | | |
| other *Moraxella* spp. | + | + | | | | | + | | + |
| *Morganella morganii* | | | | + | + | + | | | |
| *Mycoplasma buccale* | + | + | | | | | | | |
| *Mycoplasma faucium* | + | | | | | | | | |
| *Mycoplasma fermentans* | + | + | | | | | + | | |
| *Mycoplasma genitalium* | + | | | | | | + | | |
| *Mycoplasma hominis* | + | + | | | | | + | | |
| *Mycoplasma lipophilum* | + | + | | | | | | | |
| *Mycoplasma orale* | + | + | | | | | | | |
| *Mycoplasma penetrans* | | | | | | | + | | |
| *Mycoplasma pneumoniae* | + | + | | | | | | | |
| *Mycoplasma primatum* | | | | | | | + | | |
| *Mycoplasma salivarium* | + | + | | | | | | | |
| *Mycoplasma spermatophilum* | | | | | | | + | | |
| *Neisseria cinerea* | + | | | | | | | | |
| *Neisseria flavescens* | + | | | | | | | | |
| *Neisseria lactamica* | + | | | | | | | | |
| *Neisseria meningitidis* | + | | | | | | | + | |

TABLE 1-continued

Human Bacterial Normal Flora (Endogenous Bacterial Human Pathogens)

| Bacterial species | Respiratory | Mouth | Stomach | Duodenum/Jejunum | Ileum | Colon | GU System | Genital | Skin |
|---|---|---|---|---|---|---|---|---|---|
| *Neisseria mucosa* | + | | | | | | | | |
| *Neisseria polysaccharea* | + | | | | | | | | |
| *Neisseria sicca* | + | | | | | | | | |
| *Neisseria subflava* | + | | | | | | | | |
| *Oligella ureolytica* | | | | | | | + | + | |
| *Oligella urethralis* | | | | | | | + | + | |
| *Pantoea agglomerans* | | | | + | + | + | | | |
| *Pasteurella bettyae* | | | | | | | + | + | |
| *Pasteurella multocida* | + | + | | | | | | | |
| *Pediococcus* spp. | | + | | | | + | | | |
| *Peptococcus niger* | | | | | | | + | + | + |
| *Peptoniphilus asaccharolyticus* | | | | + | + | + | + | + | + |
| *Peptoniphilus lacrimalis* | + | | | | | | | | |
| *Peptostreptococcus anaerobus* | + | + | | + | + | + | | | |
| *Peptostreptococcus productus* | | | | + | + | + | | | |
| *Peptostreptococcus vaginalis* | | | | | | | + | + | + |
| *Porphyromonas asaccharolytica* | | + | | + | + | + | + | + | |
| *Porphyromonas catoniae* | + | + | | + | | | | | |
| *Porphyromonas endodontalis* | + | + | | + | | | | | |
| *Porphyromonas gingivalis* | + | + | | + | | | | | |
| *Prevotella bivia* | | | | | | | + | + | |
| *Prevotella buccae* | + | + | | + | | | | | |
| *Prevotella buccalis* | + | + | | + | | | + | + | |
| *Prevotella corporis* | + | + | | + | | | | | |
| *Prevotella dentalis* | + | + | | + | | | | | |
| *Prevotella denticola* | + | + | | + | | | | | |
| *Prevotella disiens* | | | | | | | + | + | |
| *Prevotella enoeca* | + | + | | + | | | | | |
| *Prevotella heparinolytica* | + | + | | + | | | | | |
| *Prevotella intermedia* | + | + | | + | | | | | |
| *Prevotella loescheii* | + | + | | + | | | + | + | |
| *Prevotella melaninogenica* | + | + | | + | | | + | + | |
| *Prevotella nigrescens* | + | + | | + | | | | | |
| *Prevotella oralis* | + | + | | + | | | + | + | |
| *Prevotella oris* | + | + | | + | | | | | |
| *Prevotella oulorum* | + | + | | + | | | | | |
| *Prevotella tannerae* | + | + | | + | | | | | |
| *Prevotella veroralis* | + | + | | + | | | + | + | |
| *Prevotella zoogleoformans* | + | + | | + | | | | | |
| *Propionibacterium acnes* | | | | | | | | | + |
| *Propionibacterium avidum* | | | | | | | | | + |
| *Propionibacterium granulosum* | | | | | | | | | + |
| *Propionibacterium propionicum* | + | + | | | | | | | |
| *Propionferax innocuum* | | | | | | | | | + |
| *Proteus mirabilis* | | | | | + | + | + | | |
| *Proteus penneri* | | | | | + | + | + | | |
| *Proteus vulgaris* | | | | | + | + | + | | |
| *Providencia rettgeri* | | | | | + | + | | | |
| *Providencia stuartii* | | | | + | + | + | | | |
| *Pseudomonas aeruginosa* | | | | + | + | + | | | |
| *Retortamonas intestinalis* | | | | + | + | + | | | |
| *Rothia dentocariosa* | + | + | | | | | | | |
| *Rothia mucilaginosa* | + | + | | | | | | | |

TABLE 1-continued

Human Bacterial Normal Flora (Endogenous Bacterial Human Pathogens)

| Bacterial species | Respiratory | Mouth | Stomach | Duodenum/ Jejunum | Ileum | Colon | GU System | Genital | Skin |
|---|---|---|---|---|---|---|---|---|---|
| *Ruminococcus productus* | | | | + | + | + | | | |
| *Selenomonas* spp. | + | + | | | | | | | |
| *Serratia liquefaciens* | | | | | + | + | | | |
| *Serratia marcescens* | | | | | + | + | | | |
| *Serratia odorifera* | | | | | + | + | | | |
| *Staphylococcus aureus* | + | + | | | | | + | + | + |
| *Staphylococcus auricularis* | | | | | | | | | + |
| *Staphylococcus capitis* | | | | | | | | | + |
| *Staphylococcus caprae* | | | | | | | | | + |
| *Staphylococcus cohnii* | | | | | | | | | + |
| *Staphylococcus epidermidis* | + | + | | | | | + | + | + |
| *Staphylococcus haemolyticus* | | | | | | | | | + |
| *Staphylococcus hominis* | | | | | | | | | + |
| *Staphylococcus lugdunensis* | | | | | | | | | + |
| *Staphylococcus pasteuri* | | | | | | | | | + |
| *Staphylococcus saccharolyticus* | | | | | | | | | + |
| *Staphylococcus saprophyticus* | | | | | | | | + | + |
| *Staphylococcus schleiferia* | | | | | | | | | + |
| *Staphylococcus simulans* | | | | | | | | | + |
| *Staphylococcus xylosus* | | | | | | | | | + |
| *Staphylococcus warneri* | | | | | | | | | + |
| *Streptococcus agalactiae* | | | | + | + | + | + | + | |
| *Streptococcus anginosus* | + | + | | + | + | + | + | + | |
| *Streptococcus bovis* | | | | + | + | + | | | |
| *Streptococcus constellatus* | + | + | | + | + | + | + | + | |
| *Streptococcus criceti* | + | + | | | | | | | |
| *Streptococcus crista* | + | + | | | | | | | |
| *Streptococcus equisimilis* | + | + | | | | | | | |
| *Streptococcus gordonii* | + | + | | | | | | | |
| *Streptococcus intermedius* | + | + | | | + | + | + | + | |
| *Streptococcus mitis* | + | + | + | | | | | | |
| *Streptococcus mutans* | + | + | | | | | | | |
| *Streptococcus oralis* | + | + | | | | | | | |
| *Streptococcus parasanguis* | + | + | | | | | | | |
| *Streptococcus pneumoniae* | + | | | | | | | | |
| *Streptococcus pyogenes* | + | + | + | | | | | | + |
| *Streptococcus salivarius* | + | + | + | | | | | | |
| *Streptococcus sanguis* | + | + | + | | | | | | |
| *Streptococcus sobrinus* | + | + | | | | | | | |
| *Streptococcus vestibularis* | + | + | | | | | | | |
| Group C + G *Streptococci* | | + | | | | + | | | |
| *Succinivibrio dextrinosolvens* | | | | + | + | + | | | |

TABLE 1-continued

Human Bacterial Normal Flora (Endogenous Bacterial Human Pathogens)

| Bacterial species | Respiratory | Mouth | Stomach | Duodenum/ Jejunum | Ileum | Colon | GU System | Genital | Skin |
|---|---|---|---|---|---|---|---|---|---|
| *Sutterella* spp. | + | + | | | + | + | + | | |
| *Suttonella indologenes* | + | + | | | | | | | |
| *Tissierella praeacuta* | | | | + | + | + | | | |
| *Treponema denticola* | + | + | | | | | | | |
| *Treponema maltophilum* | + | + | | | | | | | |
| *Treponema minutum* | | | | | | | + | | |
| *Treponema phagedenis* | | | | | | | + | | |
| *Treponema refringens* | | | | | | | + | | |
| *Treponema socranskii* | + | + | | | | | | | |
| *Treponema vincentii* | + | + | | | | | | | |
| *Turicella otitidis* | | | | | | | | | + |
| *Ureaplasma urealyticum* | + | + | | | | | + | | |
| *Veillonella* spp. | + | + | | + | + | + | | | |
| *Weeksella virosa* | | | | | | | + | + | |

Endogenous microbial flora, such as bacteria, have access to tissues for pathogenesis either through contiguous spread or bacteremic spread. Under favorable conditions, all endogenous organisms can become pathogenic and invade locally and spread by contiguous spread to adjacent tissues and organs. Endogenous bacterial flora of the skin, mouth and colon are the species that are understood to also be amenable to bacteremic spread. Bacteria that are members of a particular endogenous flora domain may therefore cause infection in tissues or organs to which these bacteria may spread. Accordingly, one aspect of the invention involves the use of endogenous microbial pathogens to treat a cancer of a tissue or organ to which the endogenous bacteria may spread to cause infection. The columns of Table 2 list 9 domains for endogenous flora, the: skin, respiratory system, genitals, GU system, mouth, stomach, duodenum/jejunum, ileum and colon. The rows of Table 2 list organs or tissues within which cancers may be situated. Accordingly, one aspect of the invention involves the use of endogenous microbial pathogens to formulate antigenic compositions, or the selection of existing formulations having the pathogens, for treating cancers situated in tissues or organs to which the pathogen may spread to cause an infection. Accordingly, in alternative embodiments, tumors situated in the tissues or organs listed in the first column of Table 2 may be treated with antigenic compositions comprising antigenic determinants that are specific for microbial pathogens that are members of the endogenous flora of one or more of the endogenous flora domains listed in the first row of Table 2 and indicated with an X or a check mark in the appropriate row. For example, tumors situated in the prostate may be treated with an antigenic composition having antigenic determinants specific for a microbial pathogen or pathogens endogenous to the GU system and/or genital system. A number of the bacterial species that are endogenous to the endogenous flora domains listed in Table 2 are listed, with the corresponding endogenous flora domains, in Table 1. Accordingly, one aspect of the invention involves the treatment of a cancer situated in a tissue listed in Table 2 with an antigenic composition comprising antigenic determinants of the bacterial species that are listed in Table 1, where the regions of endogenous flora linked to the site of the tumor in Table 2 match the regions of endogenous flora linked to the bacterial species in Table 1.

TABLE 2

Tissue/Organ Pathogenicity of Endogenous Flora

| Tissue/organ site | Skin | Respiratory | Genital | GU System | Mouth | Stomach | Duodenum/ Jejunum | Ileum | Colon |
|---|---|---|---|---|---|---|---|---|---|
| Skin | X | | | | X | | | | |
| Soft tissue (i.e. fat and muscle) (e.g., sarcoma) | X | | | | | | | | |
| Breast | X | | | | X | | | | |
| Lymph nodes: head and neck | X | X | | | X | | | | |
| Lymph nodes: axillae/arm | X | | | | ✓ | | | | ✓ |
| Lymph nodes: mediastinal | | X | | | ✓ | | | | ✓ |

TABLE 2-continued

Tissue/Organ Pathogenicity of Endogenous Flora

| Tissue/organ site | Skin | Respiratory | Genital | GU System | Mouth | Stomach | Duodenum/Jejunum | Ileum | Colon |
|---|---|---|---|---|---|---|---|---|---|
| Lymph nodes: pulmonary hilum | | X | | | | | | | |
| Lymph nodes: intra-abdominal | | | | X | ✓ | X | X | X | X |
| Lymph nodes: inguinal/leg | X | | X | | ✓ | | | | ✓ |
| Hematological (e.g. leukemias, multiple myeloma) | ✓ | | | | ✓ | | | | ✓ |
| Bone | X | | | | ✓ | | | | ✓ |
| Meninges | | X | | | X | | | | |
| Brain | ✓ | | | | ✓ | | | | ✓ |
| Spinal cord | ✓ | | | | ✓ | | | | ✓ |
| Eye/Orbit | X | X | X | | X | | | | |
| Salivary glands | | | | | X | | | | |
| Oral | | | | | X | | | | |
| Tonsil | | X | | | X | | | | |
| Nasopharynx/Sinus | | X | | | X | | | | |
| Thyroid | ✓ | | | | ✓ | | | | ✓ |
| Larynx | | X | | | X | | | | |
| Lung/Trachea/Bronchi | | X | | | | | | | |
| Pleura | ✓ | X | | | ✓ | | | | ✓ |
| Mediastinum | | X | | | | | | | |
| Heart | ✓ | | | | ✓ | | | | ✓ |
| Esophagus | | | | | | X | | | |
| Stomach | | | | | | X | | | |
| Small bowel | | | | | | | X | X | |
| Colon/Rectum | | | | | | | | | X |
| Anus | X | | | | | | | | X |
| Perineum | X | | | | | | | | X |
| Liver | ✓ | | | | ✓ | | | | ✓ |
| Gallbladder | | | | | | | X | | |
| Biliary tract | | | | | | | X | | |
| Pancreas | | | | | | | X | | |
| Spleen | ✓ | | | | ✓ | | | | ✓ |
| Adrenal gland | ✓ | | | | ✓ | | | | ✓ |
| Kidney | ✓ | | | X | ✓ | | | | ✓ |
| Ureter | | | | X | | | | | |
| Bladder | ✓ | | X | X | | | | | |
| Peritoneum | | | | | | X | X | X | X |
| Retroperitoneal area | | | X | | | X | X | X | X |
| Prostate | | | X | X | | | | | |
| Testicle | | | X | X | | | | | |
| Penis | X | | X | X | | | | | |
| Ovary/Adnexae | | | X | X | | | | | X |
| Uterus | | | X | X | | | | | X |
| Cervix | | | X | X | | | | | X |
| Vagina | | | X | | | | | | X |
| Vulva | | | X | | | | | | X |

*Bacteria have access to tissues/organs either through: Contiguous spread (X) or Bacteremic spread (✓).

In accordance with the combined information in Tables 1 and 2, cancers located in the tissues or organs set out in column 1 of Table 2 may be treated with antigenic compositions comprising antigenic determinants of the corresponding bacterial species of Table 1, so that the column headings in Table 2 are in effect replaced with the bacterial species of Table 1.

In some embodiments, microbial pathogens for use in the invention may be exogenous bacterial pathogens. For example, the organisms listed in Table 3 may be used as microbial pathogens to formulate antigenic compositions, or antigenic compositions having those pathogens may selected, for use to treat cancers situated in the tissues or organs listed with the relevant organism in Table 3. In some embodiments, antigenic determinants of both endogenous and exogenous bacterial species targeted to a specific tissue or organ may be used in combination. For example, an antigenic composition derived from, or specific for, *Clostridium difficile*, may be used to treat a cancer situated in the colon.

TABLE 3

Exogenous Bacterial Human Pathogens, and their Sites of Infection

| bacterial species | tissue/organ sites |
|---|---|
| *Achromobacter* spp. | hematological, skin, soft tissue, lung/trachea/bronchi, peritoneum, meninges, bile duct, gallbladder, kidney, bladder, ureter |
| *Actinomadura* spp. | skin, soft tissue, lung/trachea/bronchi, mediastinum, brain, spinal cord, hematological, meninges |
| *Aerobacter* spp. | small bowel, colon, hematological, peritoneum |
| *Aerococcus* spp. | hematological, heart, bone, kidney, bladder, ureter, meninges |
| *Alcaligenes* spp. | lung/trachea/bronchi |
| *Anaplasma* spp. | meninges, hematological, liver, spleen, bone, lung/trachea/bronchi |
| *Bacillus anthracis* | lung/trachea/bronchi, lymph nodes pulmonary hilum, mediastinum, meninges, skin, nasopharynx, tonsil, oral, small bowel, colon, hematological |
| *Bacillus cereus* | colon, eye, hematological |
| other *Bacillus* spp. | hematological, bone, meninges, brain, heart, lung/trachea/bronchi, mediastinum, skin, soft tissue, colon, stomach, small bowel, eye |
| *Balneatrix* spp. | lung/trachea/bronchi, meninges, hematological |
| *Bartonella bacilliformis* | skin, hematological, liver, muscle, lymph nodes |
| *Bartonella henselae* | brain, spinal cord, hematological, skin, liver, bone, pleura, lung/trachea/bronchi, mediastinum, axillary and inguinal lymph nodes, eye |
| *Bartonella quintana* | skin, hematological, liver, spleen |
| *Bergeyella zoohelcum* | skin, soft tissue, meninges, hematological, lung/trachea/bronchi |
| *Bordetella holmesii* | lung/trachea/bronchi, hematological |
| *Bordetella parapertussis* | nasopharynx, tonsil, lung/trachea/bronchi |
| *Bordetella pertussis* | nasopharynx, tonsil, lung/trachea/bronchi |
| *Borrelia burgdorferi* | meninges, brain, spinal cord, skin, eye, hematological, inguinal/axillary/cervical lymph nodes, muscle, liver, spleen, nasopharynx, lung/trachea/bronchi, testes |
| *Borrelia recurrentis* | brain, spinal cord, hematological, small bowel, liver, spleen, salivary glands, lung/trachea/bronchi, lymph nodes, eye, skin |
| *Brevundimonas* spp. | peritoneum, hematological, skin, soft tissue |
| *Brucella* spp. | lung/trachea/bronchi, lymph nodes pulmonary hilum, meninges, brain, spinal cord, lymph nodes, mediastinum, bone, eye, small bowel, colon, liver, biliary tract, kidney, ureter, bladder, hematological, skin, testes, spleen, prostate |
| *Burkholderia gladioli* | hematological, meninges, lung/trachea/bronchi |
| *Burkholderia mallei* | lung/trachea/bronchi, skin, soft tissue, liver, spleen, muscle, lymph nodes pulmonary hilum, mediastinal lymph nodes, mediastinum, head and neck lymph nodes, hematological |
| *Burkholderia pseudomallei* | lung/trachea/bronchi, skin, kidney, bladder, ureter, soft tissue, bone, brain, spinal cord, muscle, hematological, prostate, kidney, ureter, meninges |
| *Calymmatobacterium granulomatis* | skin, penis, vulva, soft tissue, vagina, cervix, bone, hematological, inguinal lymph nodes |
| *Campylobacter coli* | small bowel, colon |
| *Campylobacter fetus* | lung/trachea/bronchi, small bowel, colon, meninges, brain, peritoneum, bone, gallbladder, ovaries, hematological, heart, kidney, bladder, ureter |
| *Campylobacter jejuni* | colon, hematological, gallbladder, pancreas, bladder, bone, meninges |
| *Campylobacter sputorum* | small bowel, colon |
| *Capnoctyophaga canimorsus* | skin, soft tissue, meninges, hematological, bone, lung/trachea/bronchi, eye |
| *Capnoctyophaga cynodegmi* | skin, soft tissue, meninges, hematological, bone, lung/trachea/bronchi, eye |
| CDC groups EF-4a and EF-4b | hematological, eye, skin, soft tissue |
| *Chlamydia pneumoniae* | lung/trachea/bronchi, lymph nodes pulmonary hilum, liver, brain, meninges, skin, thyroid, pancreas, hematological |
| *Chlamydia psittaci* | lung/trachea/bronchi, lymph nodes pulmonary hilum, mediastinum, liver, brain, meninges, hematological, skin, thyroid, pancreas |
| *Chlamydia trachomatis* | inguinal lymph nodes, penis, vulva, vagina, cervix, uterus, ovaries and adnexae, peritoneum, prostate, eye |
| *Chlamydophila pneumoniae* | laryngx, trachea/bronchi, hematological |
| *Chromobacterium violaceum* | hematological, liver, spleen, lung/trachea/bronchi, kidney, bladder, ureter, eye/orbit, bone, brain, meninges, spinal cord |
| *Chlamydophila psittaci* | lung/trachea/bronchi |
| *Chryseobacterium* spp. | meninges, lung/trachea/bronchi, hematological |
| *Clostridium bifermentans* | small bowel, colon, stomach, skin, soft tissue, hematological |

TABLE 3-continued

Exogenous Bacterial Human Pathogens, and their Sites of Infection

| bacterial species | tissue/organ sites |
|---|---|
| *Clostridium botulinum* | colon, small bowel, skin |
| *Clostridium difficile* | colon |
| *Clostridium indolis* | small bowel, colon, stomach, skin, soft tissue, hematological |
| *Clostridium mangenolii* | small bowel, colon, stomach, skin, soft tissue, hematological |
| *Clostridium perfringens* | small bowel, colon, stomach, skin, soft tissue, hematological, heart |
| *Clostridium sordellii* | small bowel, colon, stomach, skin, soft tissue, hematological |
| *Clostridium sporogenes* | small bowel, colon, stomach, skin, soft tissue, hematological |
| *Clostridium subterminale* | small bowel, colon, stomach, skin, soft tissue, hematological |
| *Clostridium tetani* | skin, soft tissue |
| *Comamonas* spp. | hematological, peritoneum, eye |
| *Corynebacterium pseudotuberculosis* | neck/axillary/inguinal/mediastinal lymph nodes, lymph nodes pulmonary hilum, lung/trachea/bronchi, mediastinum |
| *Coxiella burnetii* | lung/bronchi/trachea, brain, spinal cord, liver, bone |
| *Edwarsiella tarda* | skin, soft tissue, liver, meninges, small bowel, colon, bone, uterus, ovaries |
| *Ehrlichia* spp. | meninges, brain, spinal cord, hematological, bone, liver, kidney, spleen, lymph nodes |
| *Erysipelothrix rhusiopathiae* | skin, hematological, bone, brain, peritoneum |
| *Francisella tularensis* | nasopharynx, oral, tonsil, lung/trachea/bronchi, skin, axillary/head and neck/inguinal lymph nodes, hematological, eye, small bowel |
| *Fusobacterium* spp. | skin, soft tissue, hematological |
| *Gordonia* spp. | skin, soft tissue, lung/trachea/bronchi, mediastinum, brain, spinal cord, hematological, meninges, eye |
| *Haemophilus ducreyi* | skin, inguinal lymph nodes, penis, vulva, vagina |
| *Helicobacter pylori* | stomach |
| *Legionella* spp. | lung/trachea/bronchi, lymph nodes pulmonary hilum, hematological, brain, spinal cord, muscle, pancreas |
| *Leptospirosis* spp. | lung/trachea/bronchi, pancreas, meninges, brain, spinal cord, skin, lymph nodes, eye, hematological, nasopharynx, oral, tonsil, kidney, liver, spleen |
| *Listeria monocytogenes* | hematological, brain, meninges, spinal cord, small bowel, colon |
| *Methylobacterium* spp. | hematological, peritoneum, skin, soft tissue, bone |
| *Mycobacterium avium* | lung/bronchi/trachea, lymph nodes pulmonary hilum, prostate, pancreas, spleen, skin, neck lymph nodes, esophagus, bone, hematological |
| *Mycobacterium bovis* | colon, small bowel |
| *Mycobacterium kansasii* | lung/bronchi/trachea, lymph nodes pulmonary hilum, prostate, bone |
| *Mycobacterium leprae* | skin, soft tissues, testes, eye |
| *Mycobacterium marinum* | skin, soft tissue, bone |
| *Mycobacterium scrofulaceum* | head and neck lymph nodes |
| *Mycobacterium tuberculosis* | lung/bronchi/trachea, lymph nodes pulmonary hilum, prostate, peritoneum, pancreas, spleen, lymph nodes, small bowel, meninges, brain, spinal cord, kidney, ureter, bladder, muscle, esophagus, colon, testes, eye, ovaries, cervix, vagina, uterus, mediastinum, larynx, skin, hematological, pleura |
| *Mycobacterium ulcerans* | skin, soft tissue |
| other *Mycobacterium* spp. | lung/bronchi/trachea, lymph nodes pulmonary hilum, skin, soft tissues, bone, head and neck lymph nodes |
| *Myroides* spp. | kidney, bladder, ureter, skin, soft tissue, hematological |
| *Neisseria gonorrhoeae* | nasopharynx, oral, tonsil, prostate, penis, vagina, cervix, uterus, ovary/adnexae, peritoneum, skin, muscle, bone, liver, hematological, head and neck and inguinal and intra-abdominal lymph nodes, anus |
| *Neorickettsia sennetsu* | hematological, bone, lymph nodes, liver, spleen |
| *Nocardia* spp. | lung/bronchi/trachea, pancreas, meninges, spinal cord, brain, skin, soft tissue, eye, bone, kidney, heart, hematological |
| *Orientia tsutsugamushi* | meninges, brain, spinal cord, hematological, skin, inguinal and axillary lymph nodes, spleen, lung/bronchi/trachea |
| *Pandoraea* spp. | lung/trachea/bronchi, hematological |
| *Pasteurella canis* | skin, soft tissue, hematological |
| *Pasteurella dagmatis* | skin, soft tissue, hematological |
| *Pasteurella stomatis* | skin, soft tissue, hematological |
| *Pediococcus* spp. | hematological, liver, colon |
| *Pityrosporum ovale* | skin |

TABLE 3-continued

Exogenous Bacterial Human Pathogens, and their Sites of Infection

| bacterial species | tissue/organ sites |
|---|---|
| *Plesiomonas shigelloides* | small bowel, colon, hematological, meninges, bone, gall bladder, skin, soft tissue |
| *Pseudomonas aeruginosa* | lung/trachea/bronchi, hemaotogical, skin, soft tissue, bone, meninges, brain, eye, kidney, bladder, ureter, heart |
| other *Pseudomonas* spp. | skin, soft tissue, lung/trachea/bronchi, mediastinum, hematological |
| *Ralstonia* spp. | hematological, meninges, bone |
| *Rhizobium* spp. | hematological, peritoneum, eye, kidney, bladder, ureter |
| *Rhodococcus* spp. | lung/trachea/bronchi, hematological, brain, skin, lymph nodes, bone, mediastinum, liver, spleen, soft tissue, spinal cord, meninges |
| *Rickettsia akari* | skin |
| *Rickettsia conorii* | lung/bronchi/trachea, lymph nodes pulmonary hilum, meninges, brain, spinal cord, hematolofical, skin, kidney, liver, spleen, pancreas |
| *Rickettsia felis* | skin, brain, spinal cord |
| *Rickettsia prowazekii* | meninges, brain, spincal cord, hematological, lung/bronchi/trachea, skin, spleen |
| *Rickettsia rickettsiae* | lung/bronchi/trachea, lymph nodes pulmonary hilum, meninges, brain, spinal cord, hematological, muscle, small bowel, liver, skin |
| *Rickettsia slovaca* | skin, head and neck lymph nodes |
| *Rickettsia typhi* | meninges, hematological, liver, kidney, brain, lung/bronchi/trachea, spleen |
| *Roseomonas* spp. | hematological, peritoneum, skin, soft tissue, bladder, kidney, ureter |
| *Salmonella* spp. | lung/bronchi/trachea, pancreas, spleen, intra-abdominal lymph nodes, stomach, small bowel, colon, meninges, skin, muscle, bone, hematological, heart |
| *Shewanella* spp. | skin, soft tissue, eye, bone, hematological, peritoneum |
| *Shigella boydii* | colon |
| *Shigella dysenteriae* | colon |
| *Shigella flexneri* | colon |
| *Shigella sonnei* | colon |
| *Sphingobacterium* spp. | brain, meninges, spinal cord, eye, skin, soft tissue |
| *Sphingomonas* spp. | hematological, meninges, peritoneum, skin, soft tissue, kidney, bladder, ureter |
| *Spirillum minus* | skin, axillary/inguinal/neck lymph nodes, hematological, liver, spleen |
| other *Spirillum* spp. | colon |
| *Stenotrophomonas maltophilia* | meninges, hematological, peritoneum, lung/trachea/bronchi, eye, kidney, bladder, ureter, skin, soft tissue |
| *Streptobacillus moniliformis* | skin, bone, hematological, lung/trachea/bronchi, meninges, brain, liver, spleen |
| *Streptococcus iniae* | skin, hematological, soft tissue |
| *Streptococcus zooepidemicus* | small bowel, nasopharynx, bone, meninges, hematological, head and neck lymph nodes |
| *Streptomices* spp. | skin, soft tissue, lung/trachea/bronchi, mediastinum, brain, spinal cord, hematological, meninges |
| *Treponema pallidum* | nasopharynx, tonsil, oral, meninges, brain, spinal cord, penis, vulva, vagina, anus, cervix, eye, hematological, inguinal and head and neck lymph nodes |
| *Tropheryma whipplei* | brain, spinal cord, hematological, small bowel, colon, heart, lung/trachea/bronchi, eye |
| *Tsukamurella* spp. | skin, soft tissue, lung/trachea/bronchi, mediastinum, brain, spinal cord, hematological, meninges |
| *Vibrio cholerae* | colon, small bowel |
| *Vibrio cincinnatiensis* | hematological, meninges |
| *Vibrio damsela* | skin, soft tissue |
| *Vibrio fluvialis* | small bowel, colon |
| *Vibrio furnissii* | small bowel, colon |
| *Vibrio hollisae* | small bowel, colon, skin, soft tissue |
| *Vibrio metschnikovii* | hematological |
| *Vibrio parahaemolyticus* | colon, small bowel |
| *Vibrio vulnificus* | soft tissue, blood, skin |
| *Yersinia enterocolitica* | nasopharynx, tonsil, small bowel, intra-abdominal lymph nodes, colon, muscle, lung/trachea/bronchi, liver, spleen, hematological |
| *Yersinia pestis* | lung/trachea/bronchi, lymph nodes pulmonary hilum, inguinal/axillary/neck lymph nodes, oral, tonsil, hematological, skin |
| *Yersinia pseudotuberculosis* | small bowel, colon, abdominal lymph nodes |

In some embodiments, microbial pathogens for use in the invention may be viral pathogens. Table 4 provides an exemplary list of viral pathogens together with the tissue and organ sites for which each viral species is reportedly a pathogen. Accordingly, one aspect of the invention involves utilizing immunogenic compositions that are specific for the named viruses to treat a cancer situated in the organs or tissues that are identified adjacent to the name of the virus in Table 4. For example, an antigenic composition derived from, or specific for, a vaccinia virus, may be used to treat a cancer situated in the skin, hematological tissues, lymph nodes, brain, spinal cord, eye or heart.

TABLE 4

Viral Human Pathogens and Their Sites of Infection

| virus | tissue/organ sites |
|---|---|
| Vaccinia | skin, hematological, lymph nodes, brain, spinal cord, eye, heart |
| Variola (smallpox) | skin, hematological, lymph nodes, brain |
| Monkeypox | skin, hematological, head and neck lymph nodes, brain, eye, lung/trachea/bronchi, pulmonary hilar lymph nodes, mediastinum, nasopharynx |
| Cowpox | skin, hematological, lymph nodes |
| Parapoxviruses | skin |
| Molluscum contagiosum | skin |
| Tanapox | skin, hematological, axillary and inguinal lymph nodes |
| Herpes Simplex virus (1 and 2) | nasopharynx, oral, tonsil, hematological, lung/bronchi/trachea, pancreas, meninges, brain, spinal cord, inguinal and head/neck lymph nodes, penis, vulva, perineum, esophagus, liver, eye, skin, rectum, tonsil, mediastinum, anus, vagina, cervix |
| Varicella-zoster | nasopharynx, sinus, lung/trachea/bronchi, pulmonary hilar lymph nodes, hematological, pancreas, meninges, brain, spinal cord, esophagus, liver, eye, skin, heart, mediastinum |
| Cytomegalovirus | nasopharynx, lymph nodes, tonsil, hematological, lung/trachea/bronchi, pancreas, abdominal lymph nodes, brain, spinal cord, esophagus, small bowel, colon/rectum, eye, liver, heart, skin, mediastinum, esophagus |
| Epstein-Barr virus | nasopharynx, tonsil, oral, lymph nodes, hematological, lung, abdominal lymph nodes, brain, spinal cord, muscles, esophagus, liver, heart, skin, spleen, kidney, muscle, heart, lung/trachea/bronchi, pulmonary hilar lymph nodes, mediastinum |
| Human herpesvirus 6 | skin, hematological, lung/trachea/bronchi, pulmonary hilar lymph nodes, brain, meninges, liver |
| Human herpesvirus 7 | skin, brain, liver |
| Human herpesvirus 8 | nasopharynx, tonsil, hematological, skin, spleen, head and neck lymph nodes |
| Simian herpes B virus | brain, spinal cord, skin, hematological, lymph nodes |
| Adenovirus | nasopharynx, oral, larynx, trachea, bronchi, lung, lymph nodes, meninges, brain, spinal cord, small bowel, colon, liver, intra-abdominal lymph nodes, mediastinum, bladder, sinus, hematological, ureter, kidney, bladder, thyroid, heart |
| BK virus | kidney |
| Human papillomavirus | skin, anus, penis, vulva, cervix, vagina, oral |
| Hepatitis B virus | liver, pancreas, hematological |
| Hepatitis D virus | liver |
| Parvovirus B19 | skin, hematological, nasopharynx, bone, kidney, heart, liver, brain, meninges |
| Orthoreoviruses | nasopharynx, small bowel, colon, oral, sinus, lymph nodes, skin, lung/trachea/bronchi, meninges, brain, spinal cord, liver |
| Orbiviruses | brain, muscle, hematological, |
| Coltiviruses | hematological, skin, muscle, oral, spleen, lymph nodes, meninges, brain |
| Rotaviruses | small bowel, colon, liver, hematological, pancreas, nasopharynx, billiary tract, meninges, brain |
| Alphaviruses | brain, spinal cord, small bowel, colon, hematological, skin, bone |
| Rubella | skin, hematological, head and neck lymph nodes, spleen, nasopharynx, bone, brain, tonsil, bronchi, liver, heart |
| Yellow fever virus | hematological, liver, lung/trachea/bronchi, kidney, adrenal gland, spleen, lymph nodes, stomach, kidney |
| Dengue fever virus | hematological, lymph nodes, skin, spleen, muscle, liver, brain, nasopharynx |
| Japanese encephalitis virus | brain, hematological, spinal cord |
| West Nile encephalitis virus | brain, hematological, spinal cord, muscle, lymph nodes, liver, spleen, pancreas, meninges |
| St. Louis encephalitis virus | brain, hematological, spinal cord, meninges, muscle, nasopharynx |
| Tick-borne encephalitis virus | brain, hematological, spinal cord, muscle, meninges |

TABLE 4-continued

Viral Human Pathogens and Their Sites of Infection

| virus | tissue/organ sites |
|---|---|
| other Flaviviruses | hematological, brain, meninges, bone, muscles, skin, lymph nodes |
| Hepatitis C virus | hematological, liver |
| Hepatitis G virus | liver |
| Coronaviruses | nasopharynx, sinus, oral, tonsil, larynx, lung/trachea/bronchi, pulmonary hilar lymph nodes, small bowel, colon, tonsil, hematological |
| Toroviruses | small bowel, colon, hematological |
| Parainfluenza viruses | nasopharynx, sinus, tonsil, oral, larynx, lung/trachea/bronchi, pulmonary hilar lymph nodes, meninges, hematological, mediastinum |
| Mumps virus | salivary glands, pancreas, brain, spinal cord, liver, testes, hematological, meninges, ovaries, bone, heart, kidney, thyroid, prostate, breast |
| Respiratory syncytial virus | nasopharynx, tonsil, sinus, lung/trachea/bronchi, pulmonary hilar lymph nodes, mediastinum, hematological, oral, pleura |
| Human metapneumovirus | nasopharynx, lung/trachea/bronchi, pulmonary hilar lymph nodes, tonsil, sinus, mediastinum, hematological, oral, pleura, larynx, eye, skin, small bowel, colon |
| Rubeola | nasopharynx, sinus, hematological, lung/trachea/bronchi, pulmonary hilar lymph nodes, intra-abdominal lymph nodes, meninges, brain, spinal cord, liver, spleen, lymph nodes, skin, thymus, eye, oral, heart |
| Hendra virus | brain, meninges, lung/trachea/bronchi, kidney, hematological, muscle, |
| Nipah virus | brain, meninges, spleen, lymph nodes, thymus, lung/trachea/bronchi, kidneys, brain, spinal cord, meninges, hematological |
| Vesicular stomatitis virus | hematological, muscle, oral, tonsil, nasopharyngeal, lymph nodes, small bowel, colon |
| Rabies virus | skin, meninges, brain, spinal cord, oral, nasopharynx, salivary glands, hematological |
| Lyssaviruses | brain, spinal cord |
| Influenza virus | nasopharynx, laryngx, lung/trachea/bronchi, pulmonary hilar lymph nodes, meninges, muscle, hematological, mediastinum, muscle, sinus, tonsil, oral, eye, pleura, brain, spinal cord, salivary glands, thyroid, heart |
| California encephalitis virus | hematological, brain, meninges |
| Hantaviruses | hematological, kidney, eye, skin, oral, muscle, lung/trachea/bronchi |
| other Bunyaviruses | brain, hematological, muscle, meninges, spinal cord |
| Lymphocytic choriomeningitis virus | hematological, muscle, lymph nodes, skin, brain, meninges, testes, bone |
| Lassa virus | nasopharynx, brain, spinal cord, lung/trachea/bronchi, pulmonary hilar lymph nodes, mediastinum, muscle, testes, eye, heart, |
| Machupo virus | brain, meninges, hematological, muscle, eye, skin, lymph nodes, nasopharynx, small bowel, colon |
| Junin virus | brain, meninges, hematological, muscle, eye, skin, lymph nodes, nasopharynx, small bowel, colon |
| Human T-Cell Lymphotropic viruses | hematological, skin, lymph nodes, muscle, eye, bone, lung, pulmonary hilar lymph nodes, spinal cord, brain |
| Poliovirus | nasopharynx, lung/trachea/bronchi, pulmonary hilar lymph nodes, small bowel, neck and intra-abdominal lymph nodes, colon, hematological, liver, spleen, skin, brain, spinal cord, meninges, heart |
| Coxsackieviruses | nasopharynx, larynx, oral, tonsil, lung/trachea/bronchi, pulmonary hilar lymph nodes, mediastinum, pancreas, muscle, brain, meninges, small bowel, neck and intra-abdominal lymph nodes, colon, hematological, spleen, skin, eye, sinus, liver, testes, bone, pleura, salivary glands, heart |
| Echoviruses | nasopharynx, oral, tonsil, lung/trachea/bronchi, pulmonary hilar lymph nodes, muscle, brain, meninges, small bowel, neck and intra-abdominal lymph nodes, colon, hematological, mediastinum, spleen, skin, eye, sinus, liver, pancreas, testes, bone, salivary glands, heart |
| other Enteroviruses | lung/trachea/bronchi, pulmonary hilar lymph nodes, meninges, brain, skin, heart |
| Hepatitis A virus | small bowel, colon, hematological, liver, spleen, brain, spinal cord, gallbladder, pancreas, kidney |
| Rhinoviruses | nasopharynx, sinus, oral, tonsil, larynx, lung/trachea/bronchi, pulmonary hilar lymph nodes |
| Noroviruses and other Caliciviruses | small bowel, colon |

TABLE 4-continued

Viral Human Pathogens and Their Sites of Infection

| virus | tissue/organ sites |
| --- | --- |
| Astroviruses | small bowel, colon |
| Picobirnaviruses | small bowel, colon |
| Hepatitis E virus | liver, small bowel, colon, hematological |

The cumulative information in Tables 1 through 4 provides an extensive identification of microbial pathogens that may be used in the formulation of antigenic compositions of the invention, together with an identification of the tissues or organs in which these organisms are pathogenic, and accordingly identifies the tissues or organs in which a cancer is situated that may be treated with the antigenic formulation.

In some embodiments, the microbial pathogen selected for use in antigenic compositions of the invention may be one that is a common cause of acute infection in the tissue or organ in which the cancer to be treated is situated. Table 5 identifies bacterial and viral pathogens of this kind, together with the tissues and organs in which they commonly cause infection.

Accordingly, in selected embodiments, a cancer residing in a tissue identified in the first column of Table 5 may be treated with an antigenic composition that comprises antigenic determinants for one or more of the pathogenic organisms listed in the second column of Table 5. For example, a cancer residing in the skin may be treated with an antigenic composition comprising antigenic determinants of one or more of the following organisms: *Staphylococcus aureus*, Beta hemolytic streptococci group A, B, C and G, *Corynebacterium diptheriae*, *Corynebacterium ulcerans*, *Pseudomonas aeruginosa*, rubeola, rubella, varicella-zoster, echoviruses, coxsackieviruses, adenovirus, vaccinia, herpes simplex, or parvo B19.

TABLE 5

Common Causes of Acute Infection (Bacterial and Viruses) For Each Tissue/Organ Site

| Tissue/organ site | Common Bacterial or Viral Pathogens of specific tissue/organ site |
| --- | --- |
| Skin | *Staphylococcus aureus*, Beta hemolytic *streptococci* group A, B, C and G, *Corynebacterium diptheriae*, *Corynebacterium ulcerans*, *Pseudomonas aeruginosa* rubeola, rubella, varicella-zoster, echoviruses, coxsackieviruses, adenovirus, vaccinia, herpes simplex, parvo B19 |
| Soft tissue (i.e. fat and muscle) (e.g., sarcoma) | *Streptococcus pyogenes*, *Staphylococcus aureus*, *Clostridium perfringens*, other *Clostridium* spp. influenza, coxsackieviruses |
| Breast | *Staphylococcus aureus*, *Streptococcus pyogenes* |
| Lymph nodes: head and neck | *Staphylococcus aureus*, *Streptococcus pyogenes* Epstein-Barr, cytomegalovirus, adenovirus, measles, rubella, herpes simplex, coxsackieviruses, varicella-zoster |
| Lymph nodes: axillae/arm | *Staphylococcus aureus*, *Streptococcus pyogenes* measles, rubella, Epstein-Barr, cytomegalovirus, adenovirus, varicella-zoster |
| Lymph nodes: mediastinal | *viridans streptococci*, *Peptococcus* spp., *Peptostreptococcus* spp., *Bacteroides* spp., *Fusobacterium* spp., *Mycobacterium tuberculosis* measles, rubella, Epstein-Barr, cytomegalovirus, varicella-zoster, adenovirus |
| Lymph nodes: pulmonary hilum | *Streptococcus pneumoniae*, *Moraxella catarrhalis*, *Mycoplasma pneumoniae*, *Klebsiella pneumoniae*, *Haemophilus influenza*, *Chlamydophila pneumoniae*, *Bordetella pertussis*, *Mycobacterium tuberculosis* influenza, adenovirus, rhinovirus, coronavirus, parainfluenza, respiratory syncytial virus, human metapneumovirus, coxsackievirus |
| Lymph nodes: intra-abdominal | *Yersinia enterocolitica*, *Yersinia pseudotuberculosis*, *Salmonella* spp., *Streptococcus pyogenes*, *Escherichia coli*, *Staphylococcus aureus*, *Mycobacterium tuberculosis* measles, rubella, Epstein-Barr, cytomegalovirus, varicella-zoster, adenovirus, influenza, coxsackieviruses |
| Lymph nodes: inguinal/leg | *Staphylococcus aureus*, *Streptococcus pyogenes* measles, rubella, Epstein-Barr, cytomegalovirus, herpes simplex |
| Hematological (e.g. leukemias, multiple myeloma) | *Staphylococcus aureus*, *Streptococcus pyogenes*, coagulase-negative *staphylococci*, *Enterococcus* spp., *Escherichia coli*, *Klebsiella* spp., *Enterobacter* spp., *Proteus* spp., *Pseudomonas aeruginosa*, *Bacteroides fragilis*, *Streptococcus pneumoniae*, group B *streptococci* rubeola, rubella, varicella-zoster, echoviruses, coxsackieviruses, adenovirus, Epstein-Barr, cytomegalovirus, herpes simplex |

TABLE 5-continued

Common Causes of Acute Infection (Bacterial and Viruses) For Each Tissue/Organ Site

| Tissue/organ site | Common Bacterial or Viral Pathogens of specific tissue/organ site |
|---|---|
| Bone | *Staphylococcus aureus*, coagulase-negative *staphylococci*, *Streptococcus pyogenes*, *Streptococcus pneumoniae*, *Streptococcus agalactiae*, other *streptococci* spp., *Escherichia coli*, *Pseudomonas* spp., *Enterobacter* spp., *Proteus* spp., *Serratia* spp. parvovirus B19, rubella, hepatitis B |
| Meninges | *Haemophilus influenzae*, *Neisseria meningitidis*, *Streptococcus pneumoniae*, *Streptococcus agalactiae*, *Listeria monocytogenes* echoviruses, coxsackieviruses, other enteroviruses, mumps |
| Brain | *Streptococcus* spp. (including *S. anginosus*, *S. constellatus*, *S. intermedius*), *Staphylococcus aureus*, *Bacteroides* spp., *Prevotella* spp., *Proteus* spp., *Escherichia coli*, *Klebsiella* spp., *Pseudomonas* spp., *Enterobacter* spp., *Borrelia burgdorferi* coxsackieviruses, echoviruses, poliovirus, other enteroviruses, mumps, herpes simplex, varicella-zoster, flaviviruses, bunyaviruses |
| Spinal cord | *Haemophilus influenzae*, *Neisseria meningitidis*, *Streptococcus pneumoniae*, *Streptococcus agalactiae*, *Listeria monocytogenes*, *Borrelia burgdorferi* coxsackieviruses, echoviruses, poliovirus, other enteroviruses, mumps, herpes simplex, varicella-zoster, flaviviruses, bunyaviruses |
| Eye/Orbit | *Staphylococcus aureus*, *Streptococcus pyogenes*, *Streptococcus pneumoniae*, *Streptococcus milleri*, *Escherichia coli*, *Bacillus cereus*, *Chlamydia trachomatis*, *Haemophilus influenza*, *Pseudomonas* spp., *Klebsiella* spp., *Treponema pallidum* adenoviruses, herpes simplex, varicella-zoster, cytomegalovirus |
| Salivary glands | *Staphylococcus aureus*, viridans streptococci (e.g., *Streptococcus salivarius*, *Streptococcus sanguis*, *Streptococcus mutans*), *Peptostreptococcus* spp., *Bacteroides* spp., and other oral anaerobes mumps, influenza, enteroviruses, rabies |
| Oral | *Prevotella melaninogenicus*, anaerobic *streptococci*, viridans *streptococci*, *Actinomyces* spp., *Peptostreptococcus* spp., *Bacteroides* spp., and other oral anaerobes herpes simplex, coxsackieviruses, Epstein-Barr |
| Tonsil | *Streptococcus pyogenes*, Group C and G B-hemolytic *streptococci* rhinoviruses, influenza, coronavirus, adenovirus, parainfluenza, respiratory syncytial virus, herpes simplex |
| Sinus | *Streptococcus pneumoniae*, *Haemophilus influenza*, *Moraxella catarrhalis*, α-*streptococci*, anaerobic bacteria (e.g., *Prevotella* spp.), *Staphylococcus aureus* rhinoviruses, influenza, adenovirus, parainfluenza |
| Nasopharynx | *Streptococcus pyogenes*, Group C and G B-hemolytic *streptococci* rhinoviruses, influenza, coronavirus, adenovirus, parainfluenza, respiratory syncytial virus, herpes simplex |
| Thyroid | *Staphylococcus aureus*, *Streptococcus pyogenes*, *Streptococcus pneumoniae* mumps, influenza |
| Larynx | *Mycoplasma pneumoniae*, *Chlamydophila pneumoniae*, *Streptococcus pyogenes* rhinovirus, influenza, parainfluenza, adenovirus, corona virus, human metapneumovirus |
| Trachea | *Mycoplasma pneumoniae* parainfluenza, influenza, respiratory syncytial virus, adenovirus |
| Bronchi | *Mycoplasma pneumoniae*, *Chlamydophila pneumoniae*, *Bordetella pertussis*, *Streptococcus pneumoniae*, *Haemophilus influenzae* influenza, adenovirus, rhinovirus, coronavirus, parainfluenza, respiratory syncytial virus, human metapneumovirus, coxsackievirus |
| Lung | *Streptococcus pneumoniae*, *Moraxella catarrhalis*, *Mycoplasma pneumoniae*, *Klebsiella pneumoniae*, *Haemophilus influenza* influenza, adenovirus, respiratory syncytial virus, parainfluenza |
| Pleura | *Staphylococcus aureus*, *Streptococcus pyogenes*, *Streptococcus pneumoniae*, *Haemophilus influenzae*, *Bacteroides fragilis*, *Prevotella* spp., *Fusobacterium* |

TABLE 5-continued

Common Causes of Acute Infection (Bacterial and Viruses) For Each Tissue/Organ Site

| Tissue/organ site | Common Bacterial or Viral Pathogens of specific tissue/organ site |
|---|---|
| | *nucleatum, peptostreptococcus* spp., *Mycobacterium tuberculosis* |
| | influenza, adenovirus, respiratory syncytial virus, parainfluenza |
| Mediastinum | *viridans streptococci, Peptococcus* spp., *Peptostreptococcus* spp., *Bacteroides* spp., *Fusobacterium* spp. |
| | measles, rubella, Epstein-Barr, cytomegalovirus |
| Heart | *Streptococcus* spp. (including *S. mitior, S. bovis, S. sanguis, S. mutans, S. anginosus), Enterococcus* spp., *Staphylococcus* spp., *Corynebacterium diptheriae, Clostridium perfringens, Neisseria meningitidis, Salmonella* spp. |
| | enteroviruses, coxsackieviruses, echoviruses, poliovirus, adenovirus, mumps, rubeola, influenza |
| Esophagus | *Actinomyces* spp., *Mycobacterium avium, Mycobacterium tuberculosis, Streptococcus* spp. |
| | cytomegalovirus, herpes simplex, varicella-zoster |
| Stomach | *Streptococcus pyogenes, Helicobacter pylori* |
| | cytomegalovirus, herpes simplex, Epstein-Barr, rotaviruses, noroviruses, adenoviruses |
| Small bowel | *Escherichia coli, Clostridium difficile, Bacteroides fragilis, Bacteroides vulgatus, Bacteroides thetaiotaomicron, Clostridium perfringens, Salmonella enteriditis, Yersinia enterocolitica, Shigella flexneri* |
| | adenoviruses, astroviruses, caliciviruses, noroviruses, rotaviruses, cytomegalovirus |
| Colon/Rectum | *Escherichia coli, Clostridium difficile, Bacteroides fragilis, Bacteroides vulgatus, Bacteroides thetaiotaomicron, Clostridium perfringens, Salmonella enteriditis, Yersinia enterocolitica, Shigella flexneri* |
| | adenoviruses, astroviruses, caliciviruses, noroviruses, rotaviruses, cytomegalovirus |
| Anus | *Streptococcus pyogenes, Bacteroides* spp., *Fusobacterium* spp., anaerobic *streptococci, Clostridium* spp., *E. coli, Enterobacter* spp., *Pseudomonas aeruginosa, Treponema pallidum* |
| | herpes simplex |
| Perineum | *Escherichia coli, Klebsiella* spp., *Enterococcus* spp., *Bacteroides* spp., *Fusobacterium* spp., *Clostridium* spp., *Pseudomonas aeruginosa*, anaerobic *streptococci, Clostridium* spp., *E. coli, Enterobacter* spp. |
| | herpes simplex |
| Liver | *Escherichia coli, Klebsiella* spp., *Streptococcus (anginosus* group), *Enterococcus* spp., other *viridans streptococci, Bacteroides* spp. |
| | hepatitis A, Epstein-Barr, herpes simplex, mumps, rubella, rubeola, varicella-zoster, coxsackieviruses, adenovirus |
| Gallbladder | *Escherichia coli, Klebsiella* spp., *Enterobacter* spp., *enterococci, Bacteroides* spp., *Fusobacterium* spp., *Clostridium* spp., *Salmonella enteriditis, Yersinia enterocolitica, Shigella flexneri* |
| Biliary tract | *Escherichia coli, Klebsiella* spp., *Enterobacter* spp., *Enterococci* spp., *Bacteroides* spp., *Fusobacterium* spp., *Clostridium* spp., *Salmonella enteriditis, Yersinia enterocolitica, Shigella flexneri* |
| | hepatitis A, Epstein-Barr, herpes simplex, mumps, rubella, rubeola, varicella-zoster, cocsackieviruses, adenovirus |
| Pancreas | *Escherichia coli, Klebsiella* spp., *Enterococcus* spp., *Pseudomonas* spp., *Staphylococcal* spp., *Mycoplasma* spp., *Salmonella typhi, Leptospirosis* spp., *Legionella* spp. |
| | mumps, coxsackievirus, hepatitis B, cytomegalovirus, herpes simplex 2, varicella-zoster |
| Spleen | *Streptococcus* spp., *Staphylococcus* spp., *Salmonella* spp., *Pseudomonas* spp., *Escherichia coli, Enterococcus* spp. |
| | Epstein-Barr, cytomegalovirus, adenovirus, measles, rubella, coxsackieviruses, varicella-zoster |
| Adrenal gland | *Streptococcus* spp., *Staphylococcus* spp., *Salmonella* spp., *Pseudomonas* spp., *Escherichia coli, Enterococcus* spp. |
| | varicella-zoster |
| Kidney | *Escherichia coli, Proteus mirabilis, Proteus vulgatus, Providentia* spp., *Morganella* spp., *Enterococcus faecalis, Pseudomonas aeruginosa* |
| | BK virus, mumps |

TABLE 5-continued

Common Causes of Acute Infection (Bacterial and Viruses) For Each Tissue/Organ Site

| Tissue/organ site | Common Bacterial or Viral Pathogens of specific tissue/organ site |
|---|---|
| Ureter | *Escherichia coli, Proteus mirabilis, Proteus vulgatus, Providentia* spp., *Morganella* spp., *Enterococcus* spp. |
| Bladder | *Escherichia coli, Proteus mirabilis, Proteus vulgatus, Providentia* spp., *Morganella* spp., *Enterococcus faecalis, Corynebacterium jekeum*<br>adenovirus, cytomegalovirus |
| Peritoneum | *Staphylococcus aureus, Streptococcus pyogenes, Streptococcus pneumonia, Escherichia coli, Klebsiella* spp., *Proteus* spp., *Enterococci* spp., *Bacteroides fragilis, Prevotella melaninogenica, Peptococcus* spp., *Peptostreptococcus* spp., *Fusobacterium* spp., *Clostridium* spp. |
| Retroperitoneal area | *Escherichia coli, Staphylococcus aureus* |
| Prostate | *Escherichia coli, Klebsiella* spp., *Enterobacter* spp., *Proteus mirabilis, Enterococci* spp., *Pseudomonas* spp., *Corynebacterium* spp., *Neisseria gonorrhoeae*<br>herpes simplex |
| Testicle | *Escherichia coli, Klebsiella pneumoniae, Pseudomonas aeruginosa, Staphylococcus* spp., *Streptococcus* spp., *Salmonella enteriditis*<br>mumps, coxsackievirus, lymphocytic choriomeningitis virus |
| Penis | *Staphylococcus aureus, Streptococcus pyogenes, Neisseria gonorrhoeae, Treponema pallidum*<br>herpes simplex, human papillomavirus |
| Ovary/Adnexae | *Neisseria gonorrhoeae, Chlamydia trachomatis, Gardenerella vaginalis, Prevotella* spp., *Bacteroides* spp., *Peptococcus* spp. *Streptococcus* spp., *Escherichia coli* |
| Uterus | *Neisseria gonorrhoeae, Chlamydia trachomatis, Gardenerella vaginalis, Prevotella* spp., *Bacteroides* spp., *Peptococcus* spp., *Streptococcus* spp., *Escherichia coli* |
| Cervix | *Neisseria gonorrhoeae, Chlamydia trachomatis, Treponema pallidum*<br>herpes simplex |
| Vagina | *Gardenerella vaginalis, Prevotella* spp., *Bacteroides* spp., *peptococci* spp., *Escherichia coli, Neisseria gonorrhoeae, Chlamydia Trachomatis, Treponema pallidum,*<br>herpes simplex |
| Vulva | *Staphylococcus aureus, Streptococcus pyogenes, Treponema pallidum*<br>herpes simplex |

In selected embodiments, particular microbial pathogens may be suited for treatment of particular cancers, examples of selected embodiments are set out in Table 5. These are exemplary embodiments, and not an exhaustive list of the alternative formulations for use in accordance with the invention.

The specific microbes which commonly cause infection in a specific tissue or organ may vary by geographical location. For example, *Mycobacterium tuberculosis* is a more common cause of lung infection in some geographical locations and populations than in others and therefore, while *M. tuberculosis* may not be a common lung pathogen in some geographic and population groups it may be a common lung pathogen in others. Table 5 is thus not an exhaustive list of common pathogens for all geographic locations and population groups. It is understood that a clinical microbiologist skilled in the art could determine the common pathogenic species in a particular geographic area or population group for a specific tissue or organ site in accordance with the invention. For veterinary use, there will of course be specific pathogens that are common in selected tissues of selected species, and this may also vary geographically.

In selected embodiments, the invention involves diagnostic steps to assess a patient's previous exposure to microbial pathogens. For example, the diagnostic steps may include taking a medical history of exposure to selected pathogens, and/or evaluating a patient's immune response to a selected pathogen. For example, a serology test may be conducted to detect antibodies to selected pathogens in a patient's sera. In connection with this aspect of the invention, antigenic determinants of a selected microbial pathogen may be chosen for use in an immunogenic composition on a selected patient based on a diagnostic indication that the patient has had one or more prior exposure(s) to the pathogen, for example by virtue of the presence of antibodies to antigenic determinants of that pathogen in the patient's sera.

In further selected embodiments, the invention involves diagnostic steps to assess a patient's immunological response to treatment with a selected immunogenic composition. For example, the diagnostic steps may include evaluating a patient's immune response to the antigenic determinants of that immunogenic composition, for example using a serological test to detect antibodies to those antigenic determinants. In connection with this aspect of the invention a treatment with a selected immunogenic composition may be continued if the evaluation indicates that there is an active immunological response to the antigenic determinants of that composition, and the vaccine treatment may be discontinued, and an alternative treatment with a different immunogenic composition may be initiated, if the evaluation indicates that there is not a sufficiently active immunological response to the antigenic determinants of the immunogenic composition.

As discussed in the context of Patient R, in selected embodiments, the microbial pathogen selected for use in antigenic compositions of the invention may be one that is the most common cause of acute infection in the tissue or organ in which the cancer to be treated is situated, which may provide particular benefit as illustrated by the case of Patient R. For example, for the treatment of bone cancer, *Staphylococcus aureus* would be the bacterial species selected; for the treatment of cancer in lung tissue, *Streptococcus pneumoniae* would be selected; for the treatment of breast cancer, *Staphylococcus aureus* would be selected; for the treatment of kidney or bladder cancer, *Escherichia coli* would be selected; and for the treatment of colon cancer, *Escherichia coli* would be the bacterial species selected. It is understood that a clinical microbiologist skilled in the art could determine the most frequently pathogenic species, bacterial or viral, for each specific tissue or organ in accordance with the invention. In selected embodiments, only antigenic determinants of the most common pathogen for the particular tissue or organ could be used to treat cancers of that tissue or organ. In alternative embodiments, antigenic determinants of the most common pathogen for the particular tissue or organ could be used in combination with antigenic determinants of other pathogens that are known to be pathogenic in the of that particular tissue or organ, preferentially selecting from the more common pathogens.

In some embodiments, the invention provides antigenic compositions in which a threshold proportion of antigenic determinants selected in accordance with the invention are used, relative to any other antigenic determinants in the composition. For example, antigenic compositions may have greater than X % of the antigenic determinants therein derived from pathogenic (or commonly pathogenic, or most commonly pathogenic) species, where X may for example be 10, 30, 40, 50, 60, 70, 80, 90, 95 or 100 (or any integer value between 10 and 100). For example, at least X % of the antigenic determinants in the antigenic composition may be specific for microbial pathogens that are pathogenic (or commonly pathogenic or most commonly pathogenic) in the specific organ or tissue of the patient within which the cancer is situated. Using an alternative measure, of the total number of microbial pathogens in the antigenic composition, at least X % may be selected to be microbial pathogens that are pathogenic (or commonly pathogenic or most commonly pathogenic) in the specific organ or tissue of the patient within which the cancer is situated. In some embodiments, the antigenic composition may accordingly consist essentially of antigenic determinants of one or more microbial pathogens that are each pathogenic (or commonly pathogenic or most commonly pathogenic) in the specific organ or tissue of the patient within which the cancer is situated. The following data illustrates the surprising effectiveness of these selected formulations:

(1) The use of MRV (which contains many common respiratory tract pathogens and *Staphylococcus aureus*, the most common pathogen of both breast and bone) was found to be helpful for the treatment of breast cancer with metastases to the bone (see FIG. 6). However, survival benefit (survival of patients who were treated with MRV compared to those who were not) was modest (i.e., median survival of 31 months for patients treated with the vaccine compared to 26 months for patients not treated with the vaccine). On the other hand, the one patient (Patient R) who was treated with a vaccine specifically targeted for breast cancer and bone cancer (i.e., containing only *Staphylococcus aureus*, by far the most common cause of both breast and bone infection) had a remarkable survival benefit, surviving for more than 17 years. The inclusion, in MRV, of other bacterial species that do not (or far less commonly) cause bone infection and commonly cause infection elsewhere (i.e., respiratory tract) appears to substantially reduce the benefit of this vaccine for the treatment of cancer of the breast and bone.

(2) The survival of stage 3B lung cancer patients treated with Respivax™ (i.e., median survival of 38 months and 40% 5-year survival) was substantially greater than the survival of stage 3B lung cancer patients treated with MRV (i.e., median survival of 18 months and 14% 5-year survival). Respivax™ contains substantially greater relative concentrations of the bacterial species that commonly cause lung infection than MRV does. 67% of the bacterial cell count of Respivax™ is comprised of bacterial species that are the common causes of lung infection, whereas only 30% of the bacterial cell count of MRV is comprised of bacterial species that are the common causes of lung infection. Thus, the composition having the greater proportion of bacteria that most commonly cause lung infections, Respivax™, is shown to be more effective for the treatment of lung cancer than the MRV formulation.

(3) The survival of stage 4 colon cancer patients treated with MRV (which does not contain any colon pathogens) was poorer than patients not treated with a vaccine. This indicates that treatments that use antigenic determinants that are not derived from microbes that are pathogenic in the organ or tissue in which the cancer is situated may not only be ineffective, but may also be deleterious.

(4) The Murine Studies set out below, and in particular the cancer cell model data involving treatment with *Klebsiella pneumoniae* antigenic determinants alone, compared to treatment with *Klebsiella pneumoniae* antigens in conjunction with additional antigens.

The data herein accordingly provide evidence of an increasing gradation of benefit from pathogenic, to commonly pathogenic, to most commonly pathogenic for the treatment cancer within a specific organ or tissue using targeting antigenic compositions that are derived from microbial pathogens that are pathogenic to that specific organ or tissue.

In some embodiments, the invention comprises the use of bacterial or viral vaccines that are approved for other purposes (e.g., poliomyelitis vaccine, *H. influenza* vaccine, meningococcal vaccine, pneumococcal vaccine, influenza vaccine, hepatitis B vaccine, hepatitis A vaccine, diphtheria vaccine, tetanus vaccine, pertussis vaccine, measles vaccine, mumps vaccine, rubella vaccine, varicella vaccine, BCG vaccine, cholera vaccine, Japanese encephalitis vaccine, rabies vaccine, typhoid vaccine, yellow fever vaccine, small pox vaccine, etc.) for use as cancer treatments by selecting a vaccine containing a pathogen (or antigenic constituent of a pathogen) that is pathogenic in the specific organ or tissue of the patient within which the cancer is situated by consulting Tables 1-5. For example, a *S. pneumoniae* vaccine, either a whole cell vaccine or a vaccine comprised of one or more antigenic components of *S. pneumoniae* (e.g., pneumococcal polysaccharide-23-valent) could be used to treat cancer at any of the following sites in which *S. pneumoniae* is listed as a common pathogen in Table 5: pulmonary hilar lymph nodes, hematological cancers, bone, meninges, spinal cord, eye/orbit, sinus, thyroid, bronchi, lungs, pleura or peritoneum. As a further example, a hepatitis B vaccine could be used to treat cancer at any of the following sites in which hepatitis B virus is listed as a pathogen in Table 4, as follows: liver, pancreas, or hematological cancers.

In some embodiments, selected compositions and methods are specifically excluded from the scope of the invention. For example, the use of the following microbial pathogens in the treatment of the following cancers is excluded from some embodiments, so that the claimed invention may extend to particular embodiments with the exception of one or more of the following:

a) BCG (*Mycobacterium bovis*) for the treatment of stomach cancer and colon cancer, for example by injection;
b) *Mycobacterium w* for the treatment of lung cancer, for example by injection;
c) *Mycobacterium vaccae* for the treatment of non-small-cell lung cancer, for example by injection;
d) *Corynebacterium parvum* for the treatment of melanoma, for example by injection;
e) *Streptococcus pyogenes* for the treatment of stomach cancer, for example by injection;
f) *Nocardia rubra* for the treatment of lung cancer or acute myelogenous leukemia, for example by injection;
g) *Lactobacillus casei* for the treatment of cervical cancer, for example by injection;
h) *Pseudomonas aeruginosa* for the treatment of lymphoma and lung cancer, for example by injection;
i) Vaccinia for the treatment of melanoma, for example by injection;
j) Rabies virus for the treatment of melanoma, for example by injection;
k) A composition consisting of the combined antigens of the following bacterial species for the veterinary (or, alternatively, human) treatment, for example by oral administration, for primary (or, alternatively, metastatic) cancers situated in the lung: *Streptococcus pneumoniae; Neisseria catarrhalis; Streptococcus pyogenes; Haemophilus influenzae; Staphylococcus aureus; Klebsiella pneumoniae.*
l) A composition consisting of the combined antigens of the following bacterial species for the veterinary (or, alternatively, human) treatment, for example by oral administration, for primary (or, alternatively, metastatic) cancers situated in the lung: *Streptococcus pneumoniae; Neisseria catarrhalis; Streptococcus pyogenes; Haemophilus influenzae; Staphylococcus aureus; Klebsiella pneumoniae; Klebsiella ozaenae; Streptococcus viridans.*

EXAMPLE 4

Murine Studies

In the following murine studies, the following common materials were utilized: PBS (Gibco), and mice were 7 week-old female C57BU6.

EXAMPLE 4A

Cancer of the Lung

This section relates to a Lewis lung carcinoma mouse model. The bacterial vaccines used in this experiment were as follows: *Streptococcus pneumoniae* [cells and broth] vaccine (lot #J049-1 [$2\times10^9$]; *Klebsiella pneumoniae* [cells and broth] vaccine (lot #J046-1 [$2\times10^9$]; *Staphylococcus aureus* [cells and broth] vaccine (lot #J041-2 [$10\times10^9$]; *Escherichia coli* (colon isolate) [cells and broth] vaccine (lot #J047-1 [$6\times10^9$]; *Salmonella enterica* [cells and broth] vaccine (lot #J31 [$15\times10^9$]; *Klebsiella pneumoniae* [cells only] vaccine (lot #J048-1 [$2\times10^9$]; and media only (*Klebsiella pneumoniae* media) (lot #J046-1). Mice were treated in accordance with the experimental groupings defined in Table 6.

TABLE 6

Experimental Groupings for Lung Cancer Mouse Model

| Group | Mice | Lewis Lung i.v. 10e5 cells/100 μl Day 0 | Vial # | Vaccine | s.c. injection dose schedule Day: −10, −8, −6, −4, −2, +2, +4, +6, +8, +10, +12, +14, +16, etc. |
|---|---|---|---|---|---|
| 1AB | 8 | ↓ | 1 | *S. pneumoniae* [cells and broth] | 200 × 10e6 CFUs/150 μl/mouse |
| 2AB | 8 | ↓ | 2 | *K. pneumoniae* [cells and broth] | 150 × 10e6 CFUs/75 μl/mouse |
| 3AB | 8 | ↓ | 3 | *S. aureus* [cells and broth] | 1 × 10e9 CFUs/100 μl/mouse |
| 4AB | 8 | ↓ | 4 | *E. coli* (colon) [cells and broth] | 0.9 × 10e9 CFUs/150 μl/mouse |
| 5AB | 8 | ↓ | 5 | *S. enterica* [cells and broth] | 1.5 × 10e9 CFUs/100 μl/mouse |
| 6AB | 8 | ↓ | 1 + 2 | *S. + K. pneumoniae* [cells and broth]* | S. 200 × 10e6 CFUs/75 μl/mouse K. 150 × 10e6 CFUs/75 μl/mouse |
| 7AB | 8 | ↓ | 8 | *K. pneumoniae* [cells only] | 150 × 10e6 CFUs/75 μl/mouse |
| 8ABC | 12 | ↓ | 9 | Media only (*K. pneumoniae* media) (control) | 75 μl/mouse |
| 9AB | 8 | PBS only | | none | none |

Figure 14:
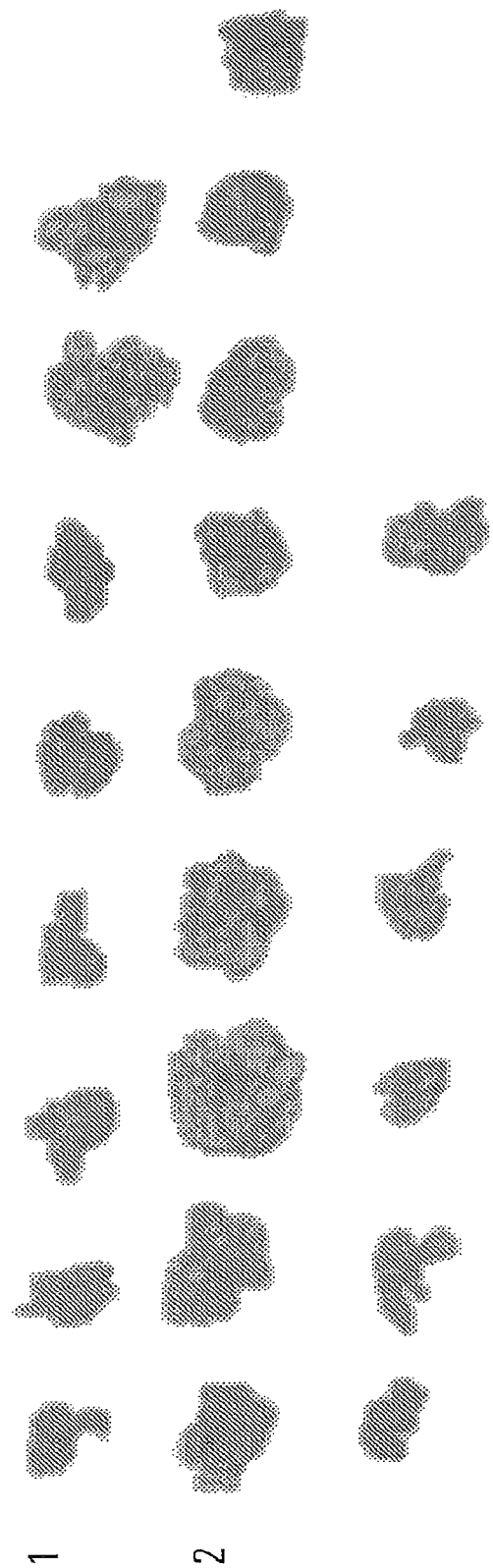
FIG. 14 shows a photograph of lungs from mice treated (row 1) and not-treated (row 2) with *K. pneumoniae* cells-only vaccine following challenge with Lewis lung carcinoma cells, as described in Example 4A herein. The bottom row (not-numbered) depicts lungs from mice that were not exposed to the mouse model of lung cancer.

Specifically, groups of mice were pre-treated sub-cutaneously with bacterial vaccines on days −10, −8, −6, −4, and −2. On day 0, mice were challenged intravenously with a dosage of 10e5 Lewis lung carcinoma cells (Cedarlane lot#508714). Thereafter, the mice were treated sub-cutaneously with vaccine injections every second day for the duration of the experiment as defined in Table 6. A control group was treated with media only. Animal weights were measured and recorded every 4 days. When mice started showing morbidity the experiment was terminated. Thereafter, all mice were humanely sacrificed and the lungs were surgically removed and weighed. Lungs were placed into the vials with Buoin's fluid and the numbers of lung nodules in each group were counted. These results are illustrated in Table 7. Representative examples of these lungs are depicted in FIG. 14.

TABLE 7

Number of visible lung tumours in mice in each group

| Group | Vaccine | Number of visible lung tumours | Average | Median |
|---|---|---|---|---|
| 1 | *S. pneumoniae* | 13, 1, 7, 1, 20, 38, 50, 35 | 20.6 | 16.5 |
| 2 | *K. pneumoniae* | 1, 10, 0, 0, 1, 2, 50 | 9.1 | 1 |
| 3 | *S. aureus* | 1, 5, 3, 15, 10, 57, 43, 38 | 21.5 | 12.5 |
| 4 | *E. coli* | 4, 3, 0, 9, 16, 3, 42, 40 | 14.6 | 6.5 |
| 5 | *S. enterica* | 0, 0, 2, 5, 2, 57, 52 | 16.8 | 2 |
| 6 | *S + K. pneumoniae* | 1, 6, 0, 0, 8, 5, 47, 48 | 14.3 | 5.5 |
| 7 | *K. pneumoniae* (cells only) | 0, 3, 0, 0, 0, 1, 46, 49 | 12.3 | 0.5 |

TABLE 7-continued

Number of visible lung tumours in mice in each group

| Group | Vaccine | Number of visible lung tumours | Average | Median |
|---|---|---|---|---|
| 8 | Control (medium) | 2, 3, 12, 25, 39, 26, 62, 39, 78 | 31.7 | 26 |

The weights of the lungs of mice injected with tumour cells were then compared to the weights of the lungs of mice injected with PBS only, to determine the tumour burden and thus, the therapeutic effect of vaccine treatment. These results are illustrated in Table 8.

TABLE 8

Average lung weight (mg) and tumour weight inhibition (compared to control) in mice immunized with killed bacterial vaccines in intravenously implanted Lewis lung carcinoma model

| Group | Vaccine | Av. Lung weight (mg) | Difference from healthy mice | Tumour Weight Inhibition (%) |
|---|---|---|---|---|
| 1 | S. pneumonia (cells and broth) | 495 | 318 | 30 |
| 2 | K. pneumonia (cells and broth) | 298 | 121 | 73 |
| 3 | S. aureus (cells and broth) | 485 | 308 | 32 |
| 4 | E. coli (cells and broth) | 372 | 195 | 57 |
| 5 | S. enterica (cells and broth) | 331 | 154 | 66 |
| 6 | S + K. pneumonia (cells and broth) | 374 | 197 | 57 |

TABLE 8-continued

Average lung weight (mg) and tumour weight inhibition (compared to control) in mice immunized with killed bacterial vaccines in intravenously implanted Lewis lung carcinoma model

| Group | Vaccine | Av. Lung weight (mg) | Difference from healthy mice | Tumour Weight Inhibition (%) |
|---|---|---|---|---|
| 7 | K. pneumoniae (cells only) | 294 | 117 | 74 |
| 8 | Control (media only) | 633 | 456 | — |
| 9 | Healthy mice | 177 | — | |

EXAMPLE 4B

Cancer of the Skin

This section relates to a mouse model of skin cancer. The bacterial vaccines used in this experiment were as follows: *Streptococcus pneumoniae* [cells and broth] vaccine (lot #J049-1 [$2 \times 10^9$]; *Klebsiella pneumoniae* [cells and broth] vaccine (lot #J046-1 [$2 \times 10^9$]; *Staphylococcus aureus* [cells and broth] vaccine (lot #J041-2 [$10 \times 10^9$]; *Escherichia coli* (colon isolate) [cells and broth] vaccine (lot #J047-1 [$6 \times 10^9$]; *Salmonella enterica* [cells and broth] vaccine (lot #J31 [$15 \times 10^9$]; *Staphylococcus aureus* [cells only] vaccine (lot #J041-2 [$10 \times 10^9$]; and media only (*S. aureus* media) (lot #J041-1). Mice were treated in accordance with the experimental groupings defined in Table 9.

TABLE 9

Experimental Groupings for Skin Cancer Mouse Model

| Group | Mice | B16 melanoma s.c. 2 × 10e5 cells 0.1 mL Day 0 | Vaccine | s.c. injection dose schedule Day: −10, −8, −6, −4, −2, +2, +4, +6, +8, +10, +12, +14, +16, etc. |
|---|---|---|---|---|
| AB1 | 8 | ↓ | S. pneumoniae [cells and broth] | 300 × 10e6 CFUs/150 μl/mouse |
| AB2 | 8 | ↓ | K. pneumoniae [cells and broth] | 150 × 10e6 CFUs/75 μl/mouse |
| AB3 | 8 | ↓ | S. aureus [cells and broth] | 1 × 10e9 CFUs/100 μl/mouse |
| AB4 | 8 | ↓ | E. coli (colon) [cells and broth] | 0.9 × 10e9 CFUs/150 μl/mouse |
| AB5 | 8 | ↓ | S. enterica [cells and broth] | 1.5 × 10e9 CFUs/100 μl/mouse |
| AB6 | 8 | ↓ | S. aureus [cells only] | 1 × 10e9 CFUs/100 μl/mouse |
| ABC7 | 12 | ↓ | Media only (S. aureus media) (control) | 100 μl/mouse |

Figure 15:
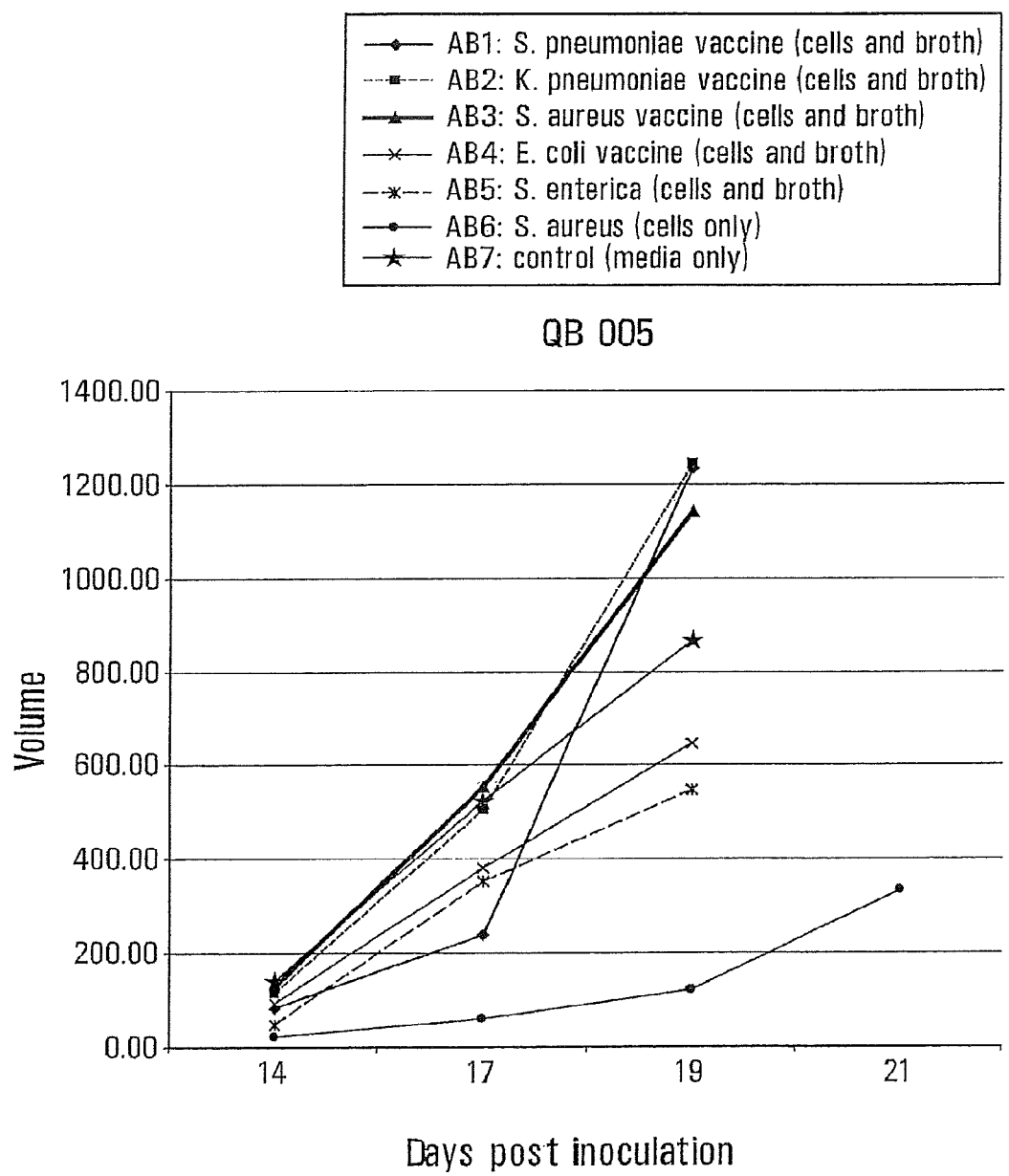
FIG. 15 shows the average tumor volume of mice treated [AB1-AB6] and not-treated [AB-7] with bacterial vaccines following challenge with B16 melanoma cells, as described in Example 4B herein.

Specifically, groups of mice were pre-treated sub-cutaneously with bacterial vaccines on days −10, −8, −6, −4, and −2. On day 0, mice were challenged intravenously with a dosage of 2×10e6 of B16 melanoma cells (lot #3995448; ATCC CRL-6323). Thereafter, the mice were treated sub-cutaneously with vaccine injections every second day for the duration of the experiment as defined in Table 9. A control group was treated with media only. Animal weights were measured and recorded every 4 days. Once tumours were palpable, the tumour diameters were measured every second day using callipers. When mice started showing morbidity, or tumour diameters reached 20 mm in any group, the experiment was terminated. Thereafter, all mice were humanely sacrificed. The average volumes of the tumours present in the groups of mice described herein are illustrated in FIG. 15.

EXAMPLE 4C

Cancer of the Colon

This section relates to a mouse model of colon cancer. The bacterial vaccines used in this experiment were as follows: *Streptococcus pneumoniae* [cells and broth] vaccine (lot #J049-1 [$2\times10^9$]; *Klebsiella pneumoniae* [cells and broth] vaccine (lot #J046-1 [$2\times10^9$]; *Staphylococcus aureus* [cells and broth] vaccine (lot #J041-2 [$10\times10^9$]; *Escherichia coli* (colon isolate) [cells and broth] vaccine (lot #J047-1 [$6\times10^9$]; *Escherichia coli* (prostate isolate) [cells and broth] vaccine (lot #J040-2 [$6\times10^9$]; *Salmonella enterica* [cells and broth] vaccine (lot #J31 [$15\times10^9$]; and media only (*E. coli* media) (lot #J040-1). Mice were treated in accordance with the experimental groupings defined in Table 10.

TABLE 10

Experimental Groupings for Colon Cancer Mouse Model

| Group | Mice | MC-38 colon i.p. $2 \times 10e5$ Day 0 | Vaccine | s.c. injection dose schedule Day: −10, −8, −6, −4, −2, +2, +4, +6, +8, +10, +12, +14, +16, etc. |
|---|---|---|---|---|
| 1AB | 8 | ↓ | *S. pneumoniae* [cells and broth] | $300 \times 10e6$ CFUs/150 μl/mouse |
| 2AB | 8 | ↓ | *K. pneumoniae* [cells and broth] | $150 \times 10e6$ CFUs/75 μl/mouse |
| 3AB | 8 | ↓ | *S. aureus* [cells and broth] | $1 \times 10e9$ CFUs/100 μl/mouse |
| 4AB | 8 | ↓ | *E. coli* (colon) [cells and broth] | $0.9 \times 10e9$ CFUs/150 μl/mouse |
| 5AB | 8 | ↓ | *E. coli* (prostate) [cells and broth] | $0.9 \times 10e9$ CFUs/150 μl/mouse |
| 6AB | 8 | ↓ | *S. enterica* [cells and broth] | $1.5 \times 10e9$ CFUs/100 μl/mouse |
| 7ABC | 12 | ↓ | Media only (*E. coli* media) (control) | 150 μl/mouse |

Figure 16:
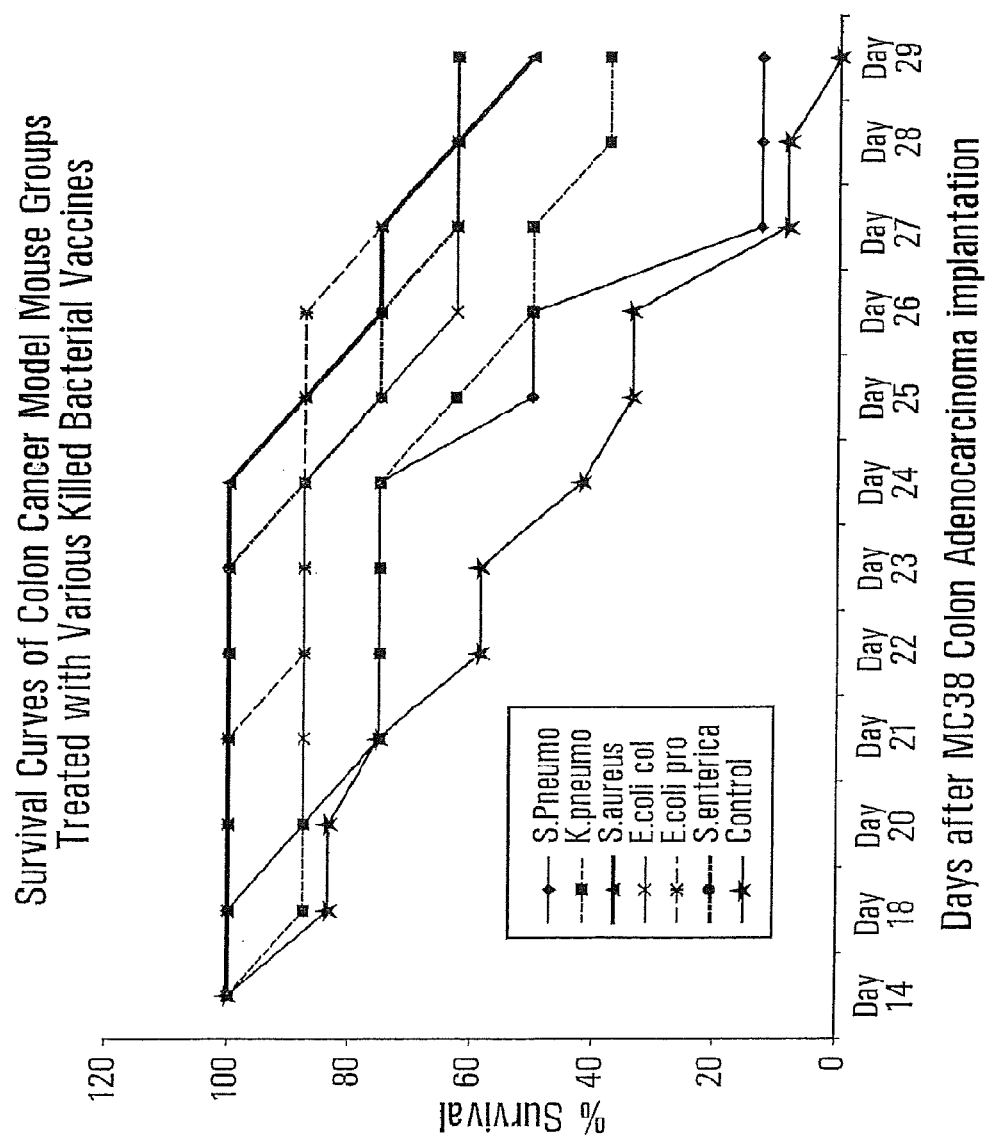
FIG. 16 shows a survival curve of colon cancer model mouse groups treated with or without a variety of bacterial vaccines, as described in Example 4C herein.

Specifically, groups of mice were pre-treated sub-cutaneously with bacterial vaccines on days −10, −8, −6, −4, and −2. On day 0, mice were challenged intraperitoneally with a dosage of $2\times10e5$ MC-38 collo adenocarcinoma cells (gift from Dr. Jeff Schlom Lab, NCI). Thereafter, the mice were treated sub-cutaneously with vaccine injections every second day for the duration of the experiment as defined in Table 10. A control group was treated with media only. The mice were observed for the following clinical factors: weight, cold to touch, diarrhea, rapid respiration, closed eyes, decreased movement, piloerection, and convulsions. When a mouse started to show signs of clinical morbidity, the mouse was humanely sacrificed and that day was defined as the day of death. Survival data for this Example is depicted in FIG. 16.

Further, the health versus morbidity/mortality of the mice involved in this Example was calculated on day 29 of the experiment as defined in Table 11.

TABLE 11

Health v. Morbidity/Mortality Group Score**

| Group | Health Status Day 29 | Vaccine | Group Score |
|---|---|---|---|
| 1 | 7 dead; 1 tumour + ascites | *S. pneumoniae* | 2 |
| 2 | 5 dead; 1 tumour + ascites; 1 tumour only; 1 healthy | *K. pneumoniae* | 17 |
| 3 | 4 dead; 2 tumour + ascites; 2 tumour only | *S. aureus* | 14 |
| 4 | 3 dead; 3 tumour only; 2 healthy | *E. coli* (colon infection isolate) | 35 |
| 5 | 3 dead; 3 tumour only; 2 healthy | *E. coli* (prostate infection isolate) | 35 |
| 6 | 3 dead; 5 healthy | *S. enterica* | 50 |
| 7 | 12 dead | Control (media only) | 0 |

**healthy = 10 points; tumour only = 5 points; tumour + ascites = 2 points; and dead = 0 points.

TABLE 12

Summary of survival for each mouse group from colon cancer experiments

| Vaccine | Mice/ group | MST* (Days) | ILS** (%) | # Cured | P value*** |
|---|---|---|---|---|---|
| *S. pneumoniae* | 8 | 27 | 12 | 0 | 0.29 |
| *K. pneumoniae* | 8 | 36 | 50 | 3 | 0.061 |
| *S. aureus* | 8 | 30 | 25 | 2 | 0.002 |
| *E. coli* (colon) | 8 | 35 | 46 | 3 | 0.008 |
| *E. coli* (prostate) | 8 | >78 | >100 | 4 | 0.001 |
| *S. enterica* | 8 | >78 | >100 | 5 | 0.003 |
| Control | 12 | 24 | 0 | 0 | — |

*MST—Median survival time
**ILS—Increase in life span over control group
***comparison to placebo treated control group
Overall Comparison Survival:
Log Rank (Mantel Cox) p = 0.001
Breslow (Generalized Wilcoxon) p = 0.003
Tarone-Ware p = 0.002

EXAMPLE 4

Summary

Skin Model:

There is a marked therapeutic advantage for the group treated with *Staph aureus* (cells-only). This study demonstrates the effectiveness of a killed *S. aureus* vaccine for the treatment of skin cancer in a mouse model, consistent with the fact that *S. aureus* is the most common cause of skin infection in mice. The data are consistent with the use of immungenic compositions of the invention to slow or inhibit cancer growth. The *S. aureus* cells-only vaccine (in which media and exotoxins were removed by centrifuging the cells and broth to collect only the cells and then reconstituting with normal saline) was more effective than *S. aureus* cells and broth vaccine (which contains media and exotoxins). This may be because *S. aureus* extoxins inhibit immune function, such as leuocidins that can kill white blood cells. The invention accordingly includes embodiments in which antigenic determinants that are to be used in immunogenic compositions are separated from immunomodulatory compounds produced by a microbial pathogen of interest.

Lung Model:

The data presented in this Example indicate that there was substantial tumour inhibition with the immunogenic composition derived from *K. pneumoniae*, consistent with the fact that *K. pnuemoniae* is a common cause of lung infection in mice. In mice (but generally not in humans), *S. enterica* can cause pneumonia, which is consistent with the beneficial effect of this vaccine in the mouse lung model. Unlike humans, for whom *S. pneumoniae* is a common lung pathogen, *S. pneumoniae* is relatively rarely a lung pathogen in mice (although *S. pneumoniae* pneumonia can be induced in mice). *E. coli* and *S. aureus* can uncommonly cause lung infection in mice, which is consistent with their mild benefit illustrated herein. This Example demonstrates that killed *K. pneumoniae* vaccine is remarkablly effective for the treatment of cancer of the lungs in mice, particularly embodiments in which the immunogenic composition includes antigens of only the most commonly pathogenic organism (see Group 2 vs. Group 6).

Colon Model:

*S. enterica* is one of the most common causes of gastrointestinal and intraperitoneal infection in mice, which is consistent with the beneficial effect illustrated herein in the treatment of gastrointestinal and intraperitonal cancer in mice.

Of the immunogenic compositions used in this Example (i.e., *S. enterica*, *E. coli*, *S. aureus*, *K. pneumoniae*, *S. pneumoniae*), *S. enterica* is the most common g.i./abdominal pathogen in mice. *E. coli* is the next most common g.i./abdominal pathogen in mice. *S. aureus* and *K. pneumoniae* can be found as part of the colonic flora and can cause g.i./abdominal infection, although far less commonly. *S. pneumoniae* does not cause g.i./abdominal infection. In accordance with this, the *S. enterica* vaccine is shown to be substantially benefical in this mouse colon tumour model, *E. coli* vaccine is shown to be moderately beneficial, *S. aureus* and *K. pneumoniae* vaccines are shown to be mildly beneficial and *S. pneumoniae* vaccine is shown to be of no benefit. In humans, *Salmonella* species cause g.i. infection and therefore, one would expect *S. enterica* and other *Salmonella* vaccines to be helpful for the treatment of colon cancer in humans.

EXAMPLE 5

Animal Models

EXAMPLE 5A

Illustrating the Influence of a Heat Inactivated *Klebsiella pneumoniae* Antigenic Composition on Monocyte/Macrophage and Dendritic Cell Populations in Mice The following methods and materials were utilized in this Example:

Mice. C57BL/6 female mice 7-8 weeks of age were ordered from Harlan Labs (Livermore, Calif.) for these studies.

Antibodies and Reagents. The following antibodies were used in this Example: anti-I-A/I-E FITC (MHC Class II; M5/114.15.2); anti-Gr-1 PE (RB6-8C5); anti-CD11b PerCP-Cy5 (M1/70); anti-CD11c APC (N418); anti-CD4 FITC (GK1.5); anti-NK1.1 PE (PK136); anti-CD8a eFluor780 (53-6.7); anti-CD44 APC (IM7). All antibodies were acquired from eBioscience (San Diego, Calif.). Liberase TM and DNAse I was acquired from Roche. All media was from HyClone (Fisher).

Treatment with Antigenic Compositions. Heat killed *K. pneumoniae* with phenol (KO12 [5.0 OD600 units]) was diluted 1/10 in PBS containing 0.4% phenol and 100 µl was injected subcutaneously on day 0, 2, 4, and 6 into 4 mice. Control mice (n=5) were injected on day 0, 2, 4, and 6 with PBS.

Brochoalveolar Lavage. On day 7 mice were sacrificed and a bronchoalveolar lavage (BAL) was performed by exposing the trachea followed by insertion of a 22G catheter attached to a 1 ml syringe. 1 ml of PBS was injected into the lungs and removed and placed into a 1.5 ml microcentrifuge tube. The lungs were subsequently washed 3 more times with 1 ml of PBS and the fluid was pooled. The first wash from each mouse was centrifuged at 400×g and the supernatant was frozen for cytokine analysis. The final 3 ml of lavage fluid was centrifuged and the cells were pooled with the cell pellet from the first lavage. The cells were counted and stained with antibodies specific for MHC class II, Ly6G/C, CD11b, and CD11c. After staining the cells were washed and analyzed on a FACS Calibur flow cytometer.

Lung Digestion. After BAL was performed the lungs were placed in 5 ml of RPMI containing 417.5 µg/ml Liberase TL (Roche) and 200 µg/ml DNAse I (Roche). The lungs were then digested at 37° C. for 30 mins. After digestion the lungs were forced through a 70 um cell strainer to create a single cell suspension. The cells were then centrifuged, washed, resuspended in FACS Buffer (PBS with 2% FCS and 5 mM EDTA) and counted. After counting the cells were stained and analyzed by FACS using the same antibodies as for the BAL cells.

Peritoneal Lavage. 1 ml of PBS was injected into the peritoneum of mice using a 1 ml syringe attached to a 25G needle after BAL. The abdomen was massaged for 1 minute and 0.5 ml of PBS was recovered from the peritoneum using a 1 ml pipet. The lavage fluid was put in a 1.5 ml centrifuge tube, centrifuged at 400×g for 5 mins, and resuspended in FACS buffer prior to staining and FACS analysis.

Spleen and Lymph Node Analysis. The spleen and draining lymph node were removed after BAL and peritoneal lavage and placed in PBS. The spleen was disrupted by mashing through a 70 µm cell strainer (Fisher) and the lymph node was disrupted using the rubber end of the plunger from a 1 ml syringe. After disruption, the single cell suspension from the spleen and lymph nodes was centrifuged, washed once with FACS Buffer, and resuspended in FACS Buffer prior to counting, staining, and FACS analysis.

FACS Analysis. Cells were stained on ice for 20 mins in 96 well plates using 50 ul of antibodies diluted in FACS buffer. After 20 mins, 100 µl of FACs buffer was added to the wells and the plates were centrifuged at 400×g for 5 mins. Subsequently the media was removed and the cells were washed 1 more time with FACS buffer. After the final wash the cells were resuspended in 200 µl of FACS buffer and the data was acquired using a FACS Calibur flow cytometer (BD). A minimum of 20,000 live events were collected for all samples except the BAL where a minimum of 5,000 events was collected.

The following results were obtained in this Example.

Normal mice without tumours were treated with a *K. pneumoniae* antigenic composition on day 0, 2, 4, and 6. On day 7 the mice were sacrificed and the bronchoalveolar lavage fluid, lung tissue, peritoneal lavage fluid, lymph nodes, and spleen was analyzed for changes in monocyte and macrophages. An increase in the number of acute inflammatory blood monocytes/macrophages, defined by high expression of CD11b and Gr-1 (same marker as Ly6c), and F4/80 in the lymph node draining the site of injection of the *K. pneumoniae* antigenic composition was observed (see: FIG. 17A). These acute inflammatory monocytes/macrophages also express very high levels of MHC class II molecules suggesting exposure to bacterial antigens. Importantly, treatment of mice with the *K. pneumoniae* antigenic composition for one week led to a marked increase in the frequency of acute inflammatory monocytes in the bronchoalveolar lavage fluid and in the lungs (i.e., the targeted organ) but not in the spleen or peritoneum of treated mice, suggesting that treatment can induce homing of monocytes specifically to the lungs without affecting other organs (see: FIG. 17B). Monocytes can differentiate into dendritic cells (DCs) in the lungs (35) and consistent with our observations of a marked increase in monocyte recruitment it was also observed that there was a marked increase in the frequency of cells displaying markers for mature DCs (see: FIG. 17C).

Figure 17:
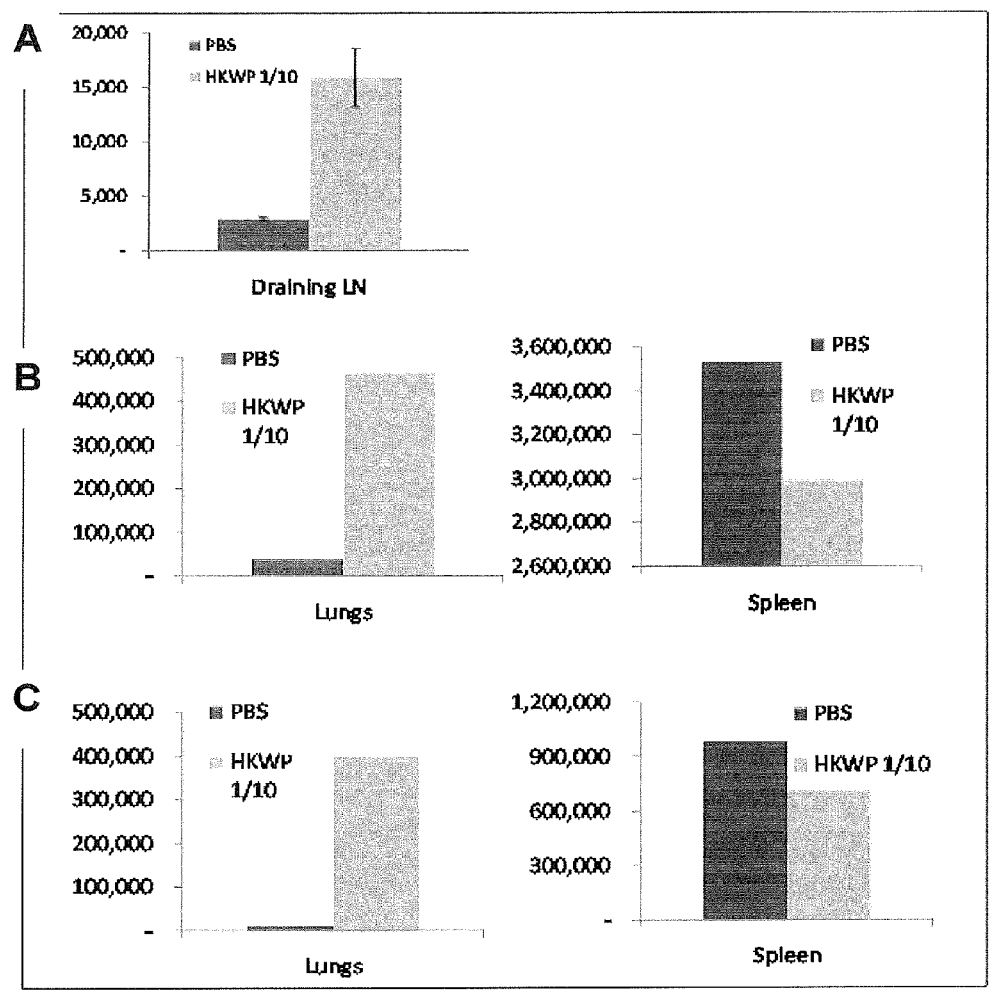
FIG. 17 shows the number of inflammatory monocytes and dendritic cells in the draining lymph node, lungs, and spleen following treatment with either a *K. pneumoniae* antigenic composition or PBS, as described in Example 5A herein.

As illustrated in FIG. 17, treatment with a *K. pneumoniae* antigenic composition for 7 days resulted in a marked increase (compared to treatment with placebo=PBS) in both acute inflammatory monocytes and dendritic cells in the lungs of mice. As illustrated in FIG. 17, mice were treated with either a *K. pneumoniae* antigenic composition for or PBS on day 0, 2, 4, and 6. On day 7, the mice were sacrificed and the total number of A) and B) inflammatory monocytes (CD11b+ Gr-1+ cells) and C) dendritic cells (CD11c+ MHC class II+ cells) were determined by flow cytometry in the lung and spleen. The error bars depicted in A) represent the mean of 4-5 mice per group.

EXAMPLE 5B

Illustrating the Influence of a Heat Inactivated *Klebsiella pneumoniae* Antigenic Composition and a Heat Inactivated *E. coli* Antigenic Composition on Monocyte/Macrophage, Dendritic Cell, and Effector Cell Populations in Mice The following methods and materials were utilized in this Example:

Mice. C57BL/6 female mice 7-8 weeks of age were ordered from Harlan Labs (Livermore, Calif.) for these studies.

Antibodies and Reagents. The following antibodies were used: anti-I-A/I-E FITC (MHC Class II; M5/114.15.2); anti-Gr-1 PE (RB6-8C5); anti-CD11b PerCP-Cy5 (M1/70); anti-CD11c APC(N418); anti-CD4 FITC (GK1.5); anti-NK1.1 PE (PK136); anti-CD8a eFluor780 (53-6.7); anti-CD44 APC (IM7). All antibodies were acquired from eBioscience (San Diego, Calif.). Liberase TM and DNAse I was acquired from Roche. All media was from HyClone (Fisher).

Treatment with Antigenic Compositions. Heat-killed *K. pneumoniae* with phenol (*K. pneumoniae*; lot KO12; 5.0 OD600 units) was diluted 1/10 in PBS containing 0.4% phenol and 100 ul was injected subcutaneously on day 0, 2, 4, and 6 into 5 mice. Heat-killed *E. coli* (lot; 5.0 OD600 units) was diluted 1/10 in containing 0.4% phenol and 100 μl was injected subcutaneously on day 0, 2, 4, and 6 into 5 mice. Control mice (n=5) were injected on day 0, 2, 4, and 6 with PBS.

Brochoalveolar Lavage. On day 7 mice were sacrificed and a bronchoalveolar lavage (BAL) was performed by exposing the trachea followed by insertion of a 22G catheter attached to a 1 ml syringe. 1 ml of PBS was injected into the lungs and removed and placed into a 1.5 ml microcentrifuge tube. The lungs were subsequently washed 3 more times with 1 ml of PBS and the fluid was pooled. The first wash from each mouse was centrifuged at 400×g and the supernatant was frozen for cytokine analysis. The final 3 ml of lavage fluid was centrifuged and the cells were pooled with the cell pellet from the first lavage. The cells were counted and stained with antibodies specific for MHC class II, Ly6G/C, CD11b, and CD11c. After staining the cells were washed and analyzed on a FACS Calibur flow cytometer.

Lung Digestion. After BAL was performed the lungs were placed in 5 ml of RPMI containing 417.5 μg/ml Liberase TL (Roche) and 200 μg/ml DNAse I (Roche). The lungs were then digested at 37° C. for 30 mins. After digestion the lungs were forced through a 70 μm cell strainer to create a single cell suspension. The cells were then centrifuged, washed, resuspended in FACS Buffer (PBS with 2% FCS and 5 mM EDTA) and counted. After counting the cells were stained and analyzed by FACS using the same antibodies as for the BAL cells.

Peritoneal Lavage. 1 ml of PBS was injected into the peritoneum of mice using a 1 ml syringe attached to a 25G needle after BAL. The abdomen was massaged for 1 minute and 0.5 ml of PBS was recovered from the peritoneum using a 1 ml pipet. The lavage fluid was put in a 1.5 ml centrifuge tube, centrifuged at 400×g for 5 mins, and resuspended in FACS buffer prior to staining and FACS analysis.

Spleen and Lymph Node Analysis. The spleen and draining lymph node were removed after BAL and peritoneal lavage and placed in PBS. The spleen was disrupted by mashing through a 70 μm cell strainer (Fisher) and the lymph node was disrupted using the rubber end of the plunger from a 1 ml syringe. After disruption, the single cell suspension from the spleen and lymph nodes was centrifuged, washed once with FACS Buffer, and resuspended in FACS Buffer prior to counting, staining, and FACS analysis.

FACS Analysis. Cells were stained on ice for 20 mins in 96 well plates using 50 μl of antibodies diluted in FACS buffer. After 20 mins, 100 μl of FACs buffer was added to the wells and the plates were centrifuged at 400×g for 5 mins. Subsequently the media was removed and the cells were washed 1 more time with FACS buffer. After the final wash the cells were resuspended in 200 μl of FACS buffer and the data was acquired using a FACS Calibur flow cytometer (BD). A minimum of 20,000 live events were collected for all samples except the BAL where a minimum of 5,000 events was collected.

Figure 18:
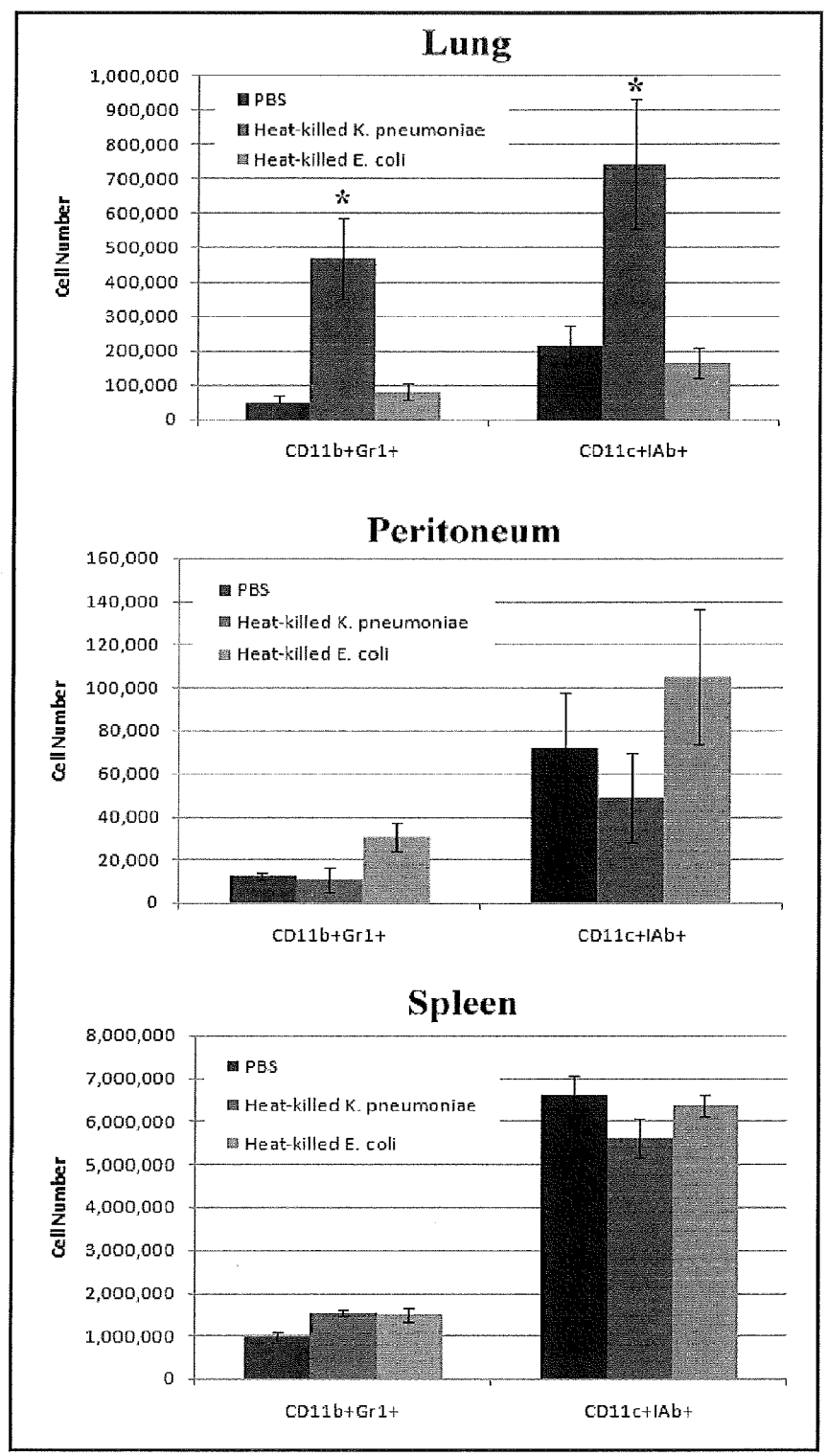
FIG. 18 shows the total number of monocytes and dendritic cells in the lung, peritoneum and spleen of mice following treatment with either a *K. pneumoniae* antigenic composition, an *E. coli* antigenic composition, or PBS, as described in Example 5B herein.

The following results were obtained in this Example:

As illustrated in FIG. 18, mice were treated on day 0, 2, 4, and 6 with either a *K. pneumoniae* antigenic composition, an *E. coli* antigenic composition or PBS. On day 7 the mice were sacrificed and the total number of inflammatory monocytes (CD11b+Gr-1+ cells) and dendritic cells (CD11c+MHC class II+ cells) were determined by flow cytometry in the peritoneal lavage fluid, lungs, lymph node and spleen. Error bars in FIG. 18 represent the standard deviation from 5 mice. *p-value <0.05 using a Student's t-test.

FIG. 18 illustrates that treatment with a *K. pneumoniae* antigenic composition, but not an *E. coli* antigenic composition treatment, markedly increased the number of monocytes and DCs in the lungs of mice. In contrast to the lungs, *K. pneumoniae* did not lead to an increase in monocytes in the peritoneum of the mice whereas *E. coli* did. Importantly, there was only a slight increase in the number of inflammatory monocytes and no increase in DCs in the spleens of mice treated with either *K. pneumoniae* or *E. coli* suggesting that the effects of the therapie are not general and are, in fact, specific for a particular organ site. In addition to looking at the effects of treatment on inflammatory monocytes and DCs in the lungs of mice, we also looked at changes in other leukocytes such as cytotoxic CD8 T cells, CD4 T helper cells, and natural killer (NK) cells all of which can potentially play a role in anti-tumour immunity.

Figure 19:
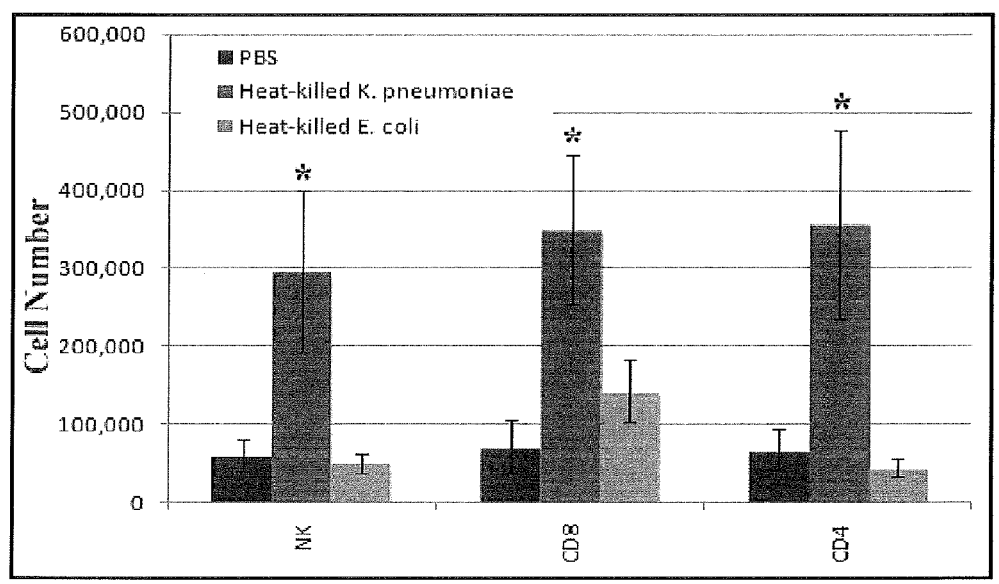
FIG. 19 shows the total number of CD4+ T cells, CD8+ T cells, and NK cells from mice treated with either a *K. pneumoniae* antigenic composition, an *E. coli* antigenic composition, or PBS, as described in Example 5B herein.

FIG. 19 illustrates that a *K. pneumoniae* antigenic composition, but not PBS or an *E. coli* antigenic composition, resulted in a marked increase in the frequency and total numbers of NK cells, CD4 and CD8 T cells in the lungs of treated mice. This Example is the first demonstration to our knowledge that subcutaneous injection of a killed bacterial species which normally causes lung infection can promote the accumulation of leukocytes in the lungs without the presence of any inflammation in that site. In addition, we have demonstrated that this effect is specific to the targeted site and that it is also specific to the bacterial constituents of the treatment used.

As illustrated in FIG. 19, mice were treated on day 0, 2, 4, and 6 with either a *K. pneumoniae* antigenic composition, an *E. coli* antigenic composition, or PBS. On day 7, the mice were sacrificed and the total number of CD4 T cells, CD8 T cells, and natural killer (NK) cells were determined by flow cytometry. Error bars represent the sd of values obtained from 5 mice per group. *p-value <0.05 using a Student's t-test.

EXAMPLE 5C

Illustrating the Effects of Heat and Phenol Inactivated *Klebsiella pneumoniae* (*K. pneumoniae*) Antigenic Compositions on Anti-Tumor Response in Mice, and the Status of Inflammatory Monocytes and Dendritic Cells Following Treatment in Tumor-Bearing Mice The following methods and materials were utilized in this Example:

Tumour Cell Inoculations. The Lewis lung carcinoma cell line derived from the C57BU6 background were acquired from ATCC (Manassas, Va.). The cells were maintained in Dulbecco's Modified Eagles Media (ATCC, Manassas, Va.) containing 10% FCS. The cells were grown in a humidified 37° C. incubator with 5% $CO_2$. Prior to tumour inoculation, cells were detached from culture plates using 0.25% trypsin and 0.53 mM EDTA. The cells were washed in PBS and resuspended at $8 \times 10^6$ cells/ml and 200 ul ($4 \times 10^5$ cells) was injected intravenously into mice.

Treatment with Antigenic Composition. The following antigenic compositions were used in this study: a heat-inactivated *K. pneumoniae* antigenic composition with phenol (lot KO12) and a phenol-inactivated *K. pneumoniae* antigenic composition (lot KO25). Both heat-inactivated *K. pneumoniae* and phenol-inactivated *K. pneumoniae* are concentrated to 5.0 OD600 units. 0.1 ml of *K. pneumoniae* diluted 1/10 in PBS with 0.4% phenol was injected subcutaneously every 2 days starting on day 2 after tumour injection.

Analysis of Inflammatory Monocytes, DCs, T Cells, and NK Cells. All analysis was done according to the methods used in Example 5B above.

TABLE 13

Experimental groupings and dose schedule for Example 5C

| Group | Number of animals/sex | LL/2 Tumor cells and dose | Site of LL/2 Tumor Injection | Treatment | Concentration of *K. Pneumoniae* (OD units) Injections | Schedule of Treatment | Injection Volume (ml) | Date of Sacrifice |
|---|---|---|---|---|---|---|---|---|
| 1A | 5F | $4 \times 10^5$ LL/2 | Intravenous | DPBSWP[1] | None | Once daily on day 2, 4, 6, and 8 | 0.1 | Day 9 |
| 2A | 5F | | | HKWP[2] | 0.05 | | | |
| 3A | 5F | | | PHWP[3] | 0.05 | | | |
| 1B | 5F | | | DPBSWP[1] | None | Once daily on day 2, 4, 6, 8, 10, 12, 14, | | Day 16 |
| 2B | 5F | | | HKWP[2] | 0.05 | | | |
| 3B | 5F | | | PHWP[3] | 0.05 | | | |
| 1C | 5F | | | DPBSNP[1] | None | Once daily on day 2, 4, 6, 8, 10, 12, 14, 16, 18, 20, 22 | | Day 23 |
| 2C | 5F | | | HKWP[2] | 0.05 | | | |
| 3C | 5F | | | PHWP[3] | 0.05 | | | |

[1] Dulbecco's Phosphate Buffered Saline with phenol
[2] Heat killed with phenol
[3] Phenol killed with phenol The following results were obtained in this Example:

This example was designed to determine if the presence of tumour impacted the recruitment of cells to the lungs and whether the treatment effect increases over time resulting in further increases in cell recruitment with ongoing treatment and thus, potentially, more optimal therapeutic effect with prolonged treatment. In addition, we wanted to determine whether a *K. pneumoniae* antigenic composition inactivated by phenol was more effective than a *K. pneumoniae* antigenic composition inactivated by heat.

Figure 20:
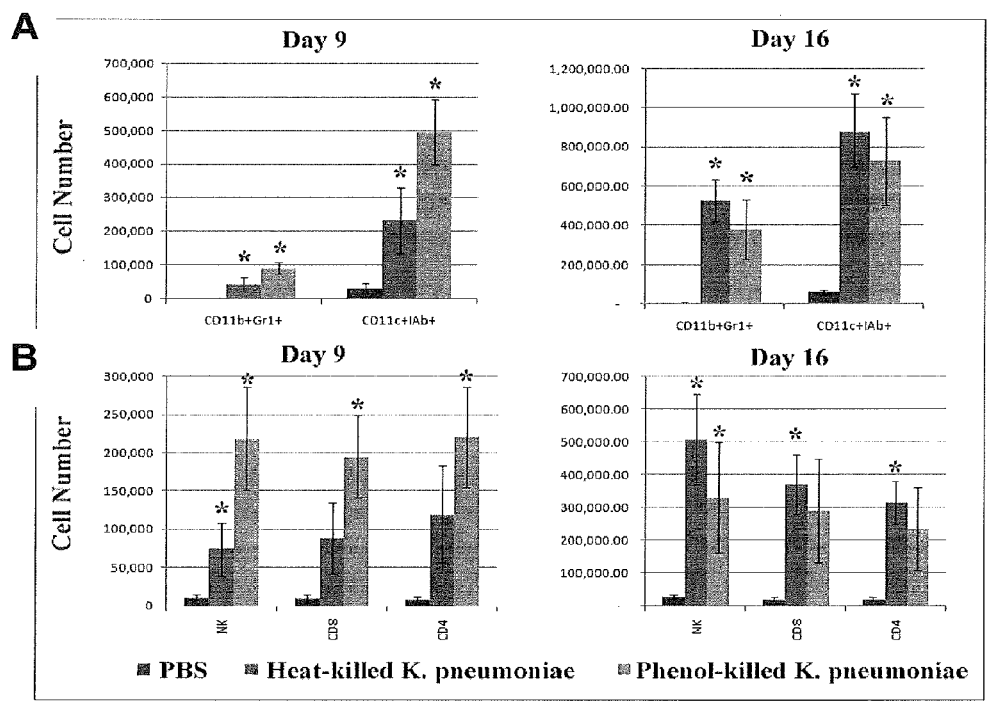
FIG. 20 shows the total number of (A) inflammatory monocytes and (B) CD4+ T cells, CD8+ T cells, and NK cells on either of day 9 or 16 from mice treated with either heat-inactivated a *K. pneumoniae* antigenic composition, a phenol-inactivated *K. pneumoniae* antigenic composition, or PBS, as described in Example 5C herein.

FIG. 20 clearly demonstrates that by day 9 (i.e., 4 treatments with a *K. pneumoniae* antigenic composition) there is already a marked increase in the number of acute inflammatory monocytes, DCs, T cells, and NK cells in the lungs of mice treated with a *K. pneumoniae* antigenic composition inactivated by heat or phenol, many times greater than that of the lungs of mice treated with placebo (normal saline=PBS), again, clearly demonstrating the marked targeted cellular immune response in the lungs triggered by *K. pneumoniae* antigenic composition therapy. On day 9, there was a suggestion that phenol inactivation was more effective than heat inactivation, but this trend reversed by day 16. Importantly, however, with reference to the cell numbers in the lungs on day 9 and day 16, it is evident that there is a cumulative effect of bacterial treatment on the recruitment of cells to the lungs. For example in the group treated with a phenol inactivated *K. pneumoniae* antigenic composition there are about 100,000 acute inflammatory monocytes in the lungs of the mice at day 9 and this number increases substantially to 400,000 by day 16, demonstrating a substantially increasing response with ongoing treatment. The same increased treatment response with ongoing treatment occurred in mice treated with heat inactivated bacteria. Importantly, this cumulative treatment effect is observed for all other cell types analyzed as well. In this study, there was no demonstrable statistically significant difference in immune cell recruitment with heat or phenol inactivated *K. pneumoniae* antigenic compositoins.

As illustrated in FIG. 20, mice were injected with $4 \times 10^5$ lewis lung carcinoma cells intravenously on day 0. The mice were subsequently treated every other day starting on day 2 with a *K. pneumoniae* antigenic composition generated by heat inactivation, or phenol inactivation, or with PBS. On day 9 and day 16 the mice were sacrificed and the total numbers of (A) inflammatory monocytes (CD11b+ Gr-1+) and DCs (CD11c+ Iab+) or (B) CD4 T cells, CD8 T cells, and natural killer (NK) cells were determined by flow cytometry. Bars represent respectively: the PBS treated group, the mice treated with a heat-inactivated *K. pneumoniae* antigenic composition and mice treated with a phenol-inactivated *K. pneumoniae* antigenic composition. Error bars represent the sd of values obtained from 5 mice per group. *p-value <0.05 using a Student's t-test.

The results of this study demonstrate an increasing immune response within the targeted tissue with ongoing treatment.

EXAMPLE 5D

Illustrating the Effects of Heat, Irradiation, and Phenol Inactivation on *K. pneumoniae* Antigenic Compositions, Including Leukocyte Recruitment into the Lungs of Mice, and the Effects of Phenol as a Preservative has any Effects The following methods and materials were utilized in this Example:

Mice. C57BL/6 female mice 7-8 weeks of age were ordered from Harlan Labs (Livermore, Calif.) for these studies.

Antigenic Compositions. Heat killed *K. pneumoniae* antigenic composition with phenol (KO12), heat killed *K. pneumoniae* antigenic composition without phenol (KO25), irradiated *K. pneumoniae* antigenic composition without phenol (KO24), and phenol killed *K. pneumoniae* antigenic composition without phenol (KO25) were used in this study. All bacterial formulations were at a concentration of 5.0 OD units in saline. For 1/10 dilution, 1 ml of bacterial formulation was added to 9 ml of DPBS and mixed immediately and then again prior to injection. For 1/100 dilution, 0.1 ml of bacterial formulation will be added to 9.9 ml of DPBS and mixed immediately and then again prior to injection. For dilutions of heat-killed *Klebsiella pneumoniae* antigenic composition with phenol, the dilutions were carried out as above using a DPBS solution containing 0.4% phenol (w/v). To prepare the 0.4% phenol in DPBS, first a 5% phenol solution was prepared by adding 0.5 g of solid phenol (Sigma Aldrich, St. Louis, Mo.) to 10 ml of DPBS (Hyclone, Logan, Utah) This solution was filtered through a 0.22 um filter (Millipore, Billerica, Mass.) and stored at 4° C. Immediately prior to use the 5% phenol solution was diluted 1 ml in 12.5 ml DPBS and used to prepare the bacterial formulations.

Treatment with Antigenic Compositions. 5 mice per group were treated subcutaneously on day 0, 2, 4, and 6 with 0.1 ml of a heat-killed *K. pneumoniae* antigenic composition diluted 1/10 in PBS or PBS with 0.4% phenol, 0.1 ml of an irradiated *K. pneumoniae* antigenic composition diluted 1/10 in PBS, or a phenol inactivated *K. pneumoniae* antigenic composition diluted 1/10 with PBS or PBS with 0.4% phenol. On day 7 the mice were sacrificed and leukocyte recruitment to the lungs was analyzed as in Example 5B.

Figure 21:
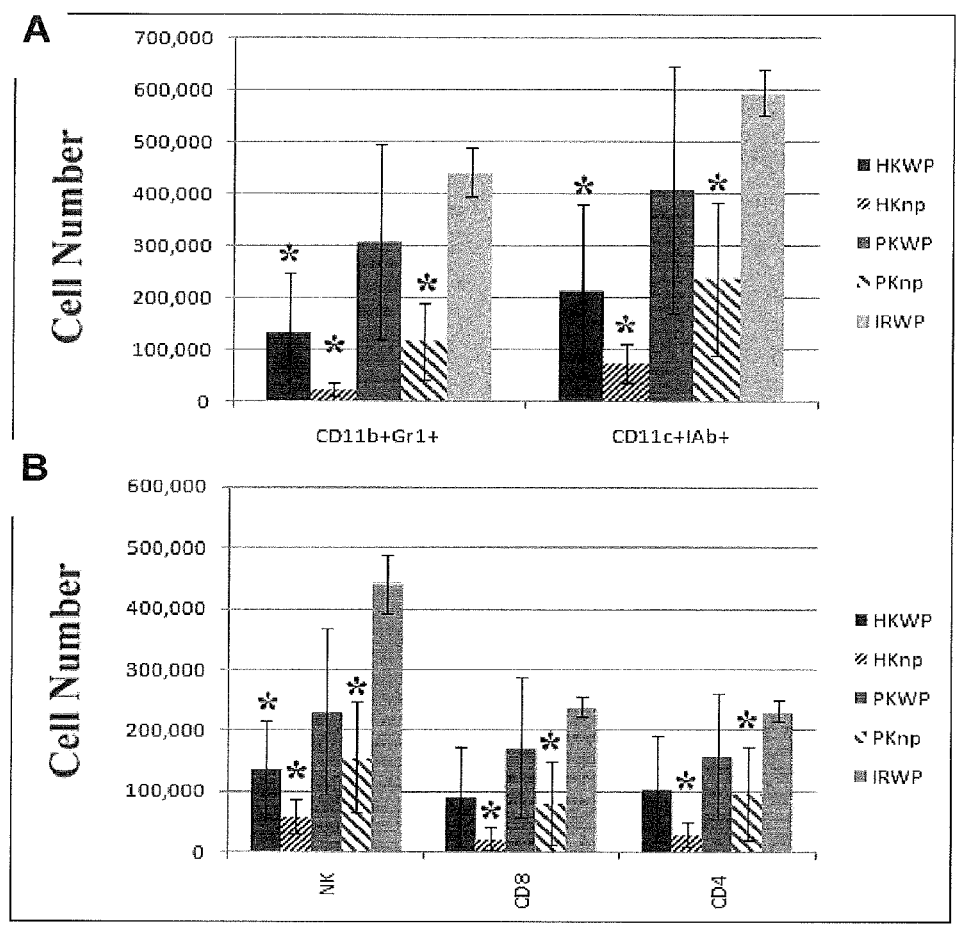
FIG. 21 shows the total number of (A) inflammatory monocytes and dendritic cells and (B) CD4+ T cells, CD8+ T cells, and NK cells from mice treated with either a heat-inactivated *K. pneumoniae* antigenic composition, a phenol-inactivated *K. pneumoniae* antigenic composition, or PBS, as described in Example 5D herein.

The following results were obtained in this Example:

In this example, we used leukocyte recruitment to the lungs as a surrogate of efficacy to compare the efficacy of *K. pneumoniae* antigenic compositions inactivated by various methods. FIG. 21 illustrates that, for both heat killed and phenol killed *K. pneumoniae* antigenic compositions, the addition of phenol (0.4%) as a preservative, increased efficacy, as measured by cellular recruitment. In some embodiments, a small amount of phenol (i.e., 0.4% as a preservative) may stabilize a component of the bacterial cell wall, for example a component that is important in antigen pattern recognition and activating an optimal targeted response. In comparing the 3 formulations containing phenol as a preservative (i.e., heat killed, phenol killed and radiation killed), irradiated *K. pneumoniae* antigenic composition led to the greatest recruitment of acute inflammatory monocytes, DCs, NK cells, and T cells to the lungs, followed by phenol killed *K. pneumoniae* antigenic composition, with heat killed *K. pneumoniae* antigenic composition resulting in the least cellular recruitment.

As illustrated in FIG. 21, mice were treated on day 0, 2, 4, and 6 with *K. pneumoniae* antigenic composition inactivated by heat (HKWP) or without (HKnp) phenol preservative, inactivated with phenol with (PKWP) or without (PKnp) phenol preservative, or *K. pneumoniae* antigenic composition inactivated by irradiation with phenol preservative (IRWP). On day 7 the mice were sacrificed and the total numbers of (A) inflammatory monocytes (CD11b+ Gr-1+) and DCs (CD11c+ Iab+) or (B) CD4 T cells, CD8 T cells, and natural killer (NK) cells were determined by flow cytometry. Error bars represent the sd of values from 5 mice per group. *p-value <0.05 compared to mice treated with IRWP using a Student's t-test.

EXAMPLE 6

Clinical Studies Involving Advanced Epithelial Cancers

Overview of Treatment

The following patients with different advanced cancers have undergone treatment with heat inactivated targeted bacterial antigenic compositions. Fully informed written consent was received for each patient and in every case. The treatment consisted of repeated (3×/week) subcutaneous injections of exact amounts of the vaccine in the abdominal region. The dosage was gradually increased in each patient to achieve a sufficient skin response (3-5 cm redness lasting for ca. 24 h). For each patient a case report form (CRF) documented skin reaction and possible clinical effects and/or side effects related to the treatment. Characteristic and concomitant treatments as well as the response to therapy of the patients are briefly described.

Patient #1:

53 y old male patient with advanced melanoma, ICD10: C43, 1st diagnosed 11/2005 lesion under right big toe nail, histology one year later 12/2006: advanced malignant melanoma; patient refused amputation of the big toe; 5/2008 lymphatic metastasis to the right leg, at the time of first presentation for targeted bacterial antigenic composition treatment (9/2008) leg swollen with 100% increase in circumference: Karnofsky 80%, no pretreatment.

Treatments over 6 month 09/2008-04/2009:
  12× intraperitoneal Ozone (O3) insufflation;
  42× locoregional radiofrequency hyperthermia (13.56 Mhz);
  18× moderate whole body hyperthermia 38.5° C.;
  6 month treatment with *Staph. aureus* antigenic composition s.c.;
  Orthomolecular medicine: high dose vitamin C infusions (0.5 g/kg/BW), Vitamin D3; 2.000 iu/day, Artesunate 200 mg/day, Celebrex 100 mg/day, low dose naltrexone, medical; mushroom (cordyceps, reishi, shitake), selenium 200 uc/day, curcumin 3.000 mg/day, proteolytic enzymes (Wobemugos)
  Epicrisis details:
  PET 7/2008: SUV in right big toe 4.81, knee: 5.01
  PET 12/2008: SUV in right big toe 3.80, knee: 4.02
  We started treatment end of 9/2008.
  At that time (9/2008) there were clinically already lymph nodes in the groin palpable which were not seen on the PET from 7/2008.
  05/2010: good clinical condition, PET confirms complete remission, Karnofsky 100%.

Patient #2:

48 y old female patient with advanced bilateral breast cancer, ICD10: C50.9 1st diagnosed 4/2008; histology ductal infiltrating adenocarcinoma of the breast, ER/PR pos., Her2 not known, T1/T2, N1 (sentinel node axilla), M0 G3; multiple treatments with sodium bicarbonate injections and repeated surgery to both breasts; patient refused the proposed bilateral mastectomy and was never resected "in sano" (e.g., margins of the lumpectomies were never free of tumor cells). Patient also refused Chemotherapy and/or hormone therapy. Karnofsky 90%, no pretreatment.

Treatments over 8 month 03/2009-11/2009:
  3× autologous Dendritic cell therapy in combination with:
  3× long-duration moderate whole body hyperthermia 40° over 8 h
  57× locoregional radiofrequency hyperthermia to both breasts (13.56 Mhz)
  6 month treatment with *Staph. aureus* antigenic composition s.c.
  Orthomolecular medicine: high dose vitamin C infusions (0.5 g/kg/BW), low dose naltrexone, medical mushroom (cordyceps, reishi, shitake), *curcuma* 3.000 mg/day, zinc
  Epicrisis details:
  Treatment started end of 3/2009.
  05/2010: bilateral breast MRI shows no abnormality detected, good clinical condition, Karnofsky 100%

Patient #3:

73 y old female patient with advanced NSCLC cancer FIGO IIc, ICD10: C34, 1st diagnosed 6/2009; histology clear cell adenocarcinoma of the lungs, T4, N1, M0 G3; she underwent neoadjuvant CHT; the restaging after 3 cycles neoadjuvant CHT demonstrated T2 tumor; she then underwent left pneumectomy R0 resection and mediastinal lymphadenectomy; Karnofsky 90%.

Treatments over 7 month 08/2009-03/2010:
  08/2009 Began chemotherapy with Taxan/Cisplatin until 10/2009 in combination with:
  4× long-duration moderate whole body hyperthermia 40° over 8 h (1-2/2009)
  20× locoregional radiofrequency hyperthermia to the thorax (13.56 Mhz) (8-10/2009)
  10/2009 le Pneumectomy R0 resection (Oncology decided against further adjuvant CHT)
  6 month treatment with *Klebsiella pneumoniae* antigenic composition s.c. (08/2009-02/2010)
  Orthomolecular medicine: thymus peptides i.m., indometacin, cimetidine, high dose vitamin C infusions (0.5 g/kg/BW), ALA/N protocol (low dose naltrexone and alpha lipoic acid), medical mushroom (reishi), *curcuma* 3.000 mg/day, zinc, melatonin, inhalation of ionized oxygen
  Epicrisis details:
  Started treatment end of 08/2009.
  05/2010: CT Thorax and Tumor marker CEA, NSE and CYFRA show complete remission, good clinical condition, Karnofsky 100%.

Patient #4:

50 y old female patient with advanced Breast cancer, ICD10: C50, with disseminated hepatic and pulmonary metastasis, 1st diagnosed 8/1990; histology undifferentiated cirrhoses type adenocarcinoma of the breast, pT1c, N1, M0 G3; she underwent multiple chemotherapy courses over 20 years; 11/2004 first scar reoccurrence, 12/2004 ablation left breast, 6×CHT Epitax and radiation of thoracic wall; 9/2005 1st diagnosis of disseminated liver and pulmonary metastases: again 8×CHT with Epitax until 3/2006. Restaging showed progressive disease at which time she began targeted bacterial antigenic composition treatment. Karnofsky 90%.

Treatments over 4 years 03/2006-03/2010:
  03/2006 Began treatment with Polyvaccinum forte vaccine in combination with:
  3× autologous Dendritic cell therapy in combination with (6-8/2006):
  3× long-duration moderate whole body hyperthermia (LD-WBH) 40° over 8 h (1-2/2009)
  25× locoregional radiofrequency hyperthermia to the thorax & liver (13.56 Mhz) (3-6/2006)
  8 month treatment with *Klebsiella pneumoniae* antigenic composition (11/2008-7/2009)
  10/2009 TM CEA and CA15/3 started rising again
  02-03/2009 2× autologous Dendritic cell therapy without LD-WBH
  04/2010 thermal ablation of liver mets (No change of lung metastasis)
  Orthomolecular medicine: thymus peptides i.m., indometacin, cimetidine, high dose vitamin C infusions (0.5 g/kg/BW), *curcuma* 3.000 mg/day, zinc, proteolytic enzymes
  Epicrisis details:
  We started treatment end of 03/2006.

05/2010: CT Thorax show stable disease over 4 years, progressive disease of liver mets, good clinical condition, Karnofsky 100%.

Patient #5:

66 y old male patient with advanced prostate cancer, ICD10: C61, with disseminated bone and lymphatic metastasis, 1st diagnosed 01/1997; histology undifferentiated adenocarcinoma of the prostate, pT3, N1, M1 G3; he underwent multiple Hormone- and CHT over 13 years; patient is in good clinical condition surviving metastatic prostate cancer for 13 years since diagnosis; Karnofsky 90%.

Treatments over 11 years 11/1999-05/2010:
13 years anti-androgen with Suprefact, Zoladex, Casodex, Trenantone, Estracyt, β-Sitosterol
06/2006-12/2007 Began Mixed bacterial vaccine treatment with Polyvaccinum forte vaccine
Since 03/2008 regular chemotherapy with Taxotere 140 mg every 3-4 weeks
50× moderate whole body hyperthermia 39° over 3 h (1999-2009)
18 month treatment with *Staph. aureus* antigenic composition (11/2008-05/2010, ongoing)
05-06/2009 2× autologous Dendritic cell therapy without moderate WBH 39°, 3 h
Orthomolecular medicine: wheat grass, cimetidine, Zometa, high dose vitamin C infusions (0.5 g/kg/BW), *curcuma* 3.000 mg/day, boswellia serrata (Indian) 400 mg 4×4/day, zinc, proteolytic enzymes
Epicrisis details:
We started treatment end of 1999.
05/2010: Bone scan shows stable disease; PSA currently 89 ng/ml, good clinical condition, Karnofsky 90%.

Patient #6:

52 y old female patient with advanced primary cancer of the peritoneum, ICD10: C48.2, with disseminated peritoneal carcinosis, 1st diagnosed 06/2003; histology undifferentiated adenocarcinoma of the peritoneum, pT3, N1, M1 G3; she underwent Debulking OP with ovarectomy bilaterly and hysterectomy and adjuvant chemotherapy with Taxol/Paraplatin: progressive disease and change to Taxol/Paraplatin with SD until 8/2008; progressive disease with disseminated peritoneal LK metastasis and 3rd line CHT with Carboplatin and beginning of treatment with targeted bacterial antigenic composition; patient was in good clinical condition; Karnofsky 100%.

Treatments over 4 month 05-09/2009:
5× Carboplatin chemotherapy (3rd line) followed by:
5× long-duration moderate whole body hyperthermia (LD-WBH) 40° over 8 h (05-09/2009)
20× locoregional radiofrequency hyperthermia to the abdomen (13.56 Mhz) (05-09/2009)
2 month treatment with *E. coli* (colon) antigenic composition (05-07/2009)
Orthomolecular medicine: high dose vitamin C infusions (0.5 g/kg/BW), high dose artichoke and sylimarin extracts (liver)
Epicrisis details:
We started treatment end of 5/2009.
04/2010: CT abdomen and tumour marker demonstrate complete remission; good clinical condition, Karnofsky 100%

Patient #7:

50 y old female patient with inoperable pancreatic cancer, ICD10: C25.9, with the cancer infiltrating the large vessels; Sonographic and CT evidence suggested invasion into superior mesenteric vein. first diagnosed 02/2009; histology undifferentiated adenocarcinoma of the pancreas, pT3, N1, M1 G3 with peritoneal carcinosis; she underwent local radiation and low dose Xeloda as radiation sensitizer; when she began treatment at our clinic the cancer was still unresectable; Karnofsky 100%.

Treatments over 2 month 06-07/2009: (*E. coli* SSI for 11 months)
1× autologous NDV-primed Dendritic cell therapy in combination with:
1× long-duration moderate whole body hyperthermia 40° over 8 h (7-10/2009)
4× moderate whole body hyperthermia 38.5°
15× locoregional radiofrequency hyperthermia to the abdomen (13.56 Mhz) (06-07/2009)
11 months treatment with *E. coli* (colon) antigenic composition (06/2009 until today, ongoing)
Orthomolecular medicine: thymus peptides i.m; medical mushroom (reishi, cordyceps, shitake;) high dose vitamin C infusions (0.5 g/kg/BW), high dose proteolytic enzyme therapy (wobenzym phlogenzym), cimetidine.
Epicrisis details:
We started treatment end of 6/2009.
05/2010: complete remission, NED; PET 02/2010 demonstrated no glucose uptake; tumour marker normal CA19/9: 4; good clinical condition, Karnofsky 100%

Other Embodiments

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method for treating a human patient for a cancer situated in the pancreas or in pancreatic tissue, the method comprising:
administering to the patient at an administration site distant from the site of the cancer a medicament comprising an effective amount of an antigenic composition comprising whole cells of a microbial pathogen that is *Escherichia coli* (*E. coli*), wherein microbial antigenic determinants of the whole cells of *E. coli* are the sole active agents or sole antigens for treatment of the cancer, wherein the treatment results in reduction in cancer cells situated in the pancreas or in the pancreatic tissue, and wherein the human patient has been diagnosed as having a cancer situated in the pancreas or in pancreatic tissue.

2. The method according to claim 1, wherein the method comprises administering the medicament in successive doses given at a dosage interval of between one hour and one month, over a dosage duration of at least two weeks.

3. The method according to claim 2, wherein the method comprises administering the medicament in a dose so that each dose is effective to cause a localized inflammatory immune response at the administration site.

4. The method according to claim 3, wherein the method comprises administering the medicament intradermally or subcutaneously in a manner such that visible localized inflammation at the administration site occurs within 1 to 48 hours.

5. The method according to claim 1, wherein the method further comprises administering to the patient an effective amount of an anti-inflammatory agent.

6. The method of claim 1, wherein the patient is a patient that has been diagnosed as having suffered from a prior pathogenic exposure to the microbial pathogen.

7. The method of claim 1, wherein the antigenic composition comprises whole killed *E. coli* cells and wherein the microbial antigenic determinants of the whole killed cells of *E. coli* are the sole active agents or sole antigens for treatment of the cancer.

8. The method of claim 1, wherein the antigenic composition comprises whole attenuated *E. coli*.

9. The method of claim 1, wherein the microbial antigenic determinants of the whole cells of *E. coli* are the sole active agents in the composition.

10. The method of claim 1, wherein the microbial antigenic determinants of the whole cells of *E. coli* are the sole antigens in the composition.

11. A method for selecting an antigenic composition and treating a human patient for a cancer situated in the pancreas or in pancreatic tissue, the method comprising:
    diagnosing the patient as having a cancer situated in the pancreas or in pancreatic tissue;
    selecting an antigenic composition comprising whole cells of a microbial pathogen that is *Escherichia coli* (*E. coli*), wherein microbial antigenic determinants of the whole cells of *E. coli* are the sole active agents or sole antigens for treatment of the cancer; and,
    administering the antigenic composition to the patient at a site distant from the site of the cancer to elicit an immune reaction to treat the cancer wherein the method comprises administering the antigenic composition by subcutaneous injection or intradermal injection, and the whole cells of *E.coli* are attenuated or killed.

12. The method of claim 11, wherein the method comprises administering the antigenic composition by subcutaneous or intradermal injection to produce a localized skin immune response at a site of administration.

13. The method according to claim 12, wherein the method comprises administering the antigenic composition so that visible localized inflammation at the administration site occurs within 1 to 48 hours.

14. The method of claim 11, wherein the antigenic composition comprises whole killed *E. coli* cells and wherein the microbial antigenic determinants of the whole killed cells of *E. coli* are the sole active agents or sole antigens for treatment of the cancer.

15. The method of claim 11, wherein the microbial antigenic determinants of the whole cells of *E. coli* are the sole active agents in the composition.

16. The method of claim 11, wherein the microbial antigenic determinants of the whole cells of *E. coli* are the sole antigens in the composition.

17. The method of claim 11, wherein the antigenic composition comprises whole attenuated *E. coli*.

* * * * *

UNITED STATES PATENT AND TRADEMARK OFFICE
CERTIFICATE OF CORRECTION

Page 1 of 1

| | |
|---|---|
| PATENT NO. | : 9,320,788 B2 |
| APPLICATION NO. | : 13/923211 |
| DATED | : April 26, 2016 |
| INVENTOR(S) | : Harold David Gunn |

It is certified that error appears in the above-identified patent and that said Letters Patent is hereby corrected as shown below:

In the claims,

Column 98, line 59, at the end of claim 1, add the following phrase -- wherein the method comprises administering the medicament intradermally or subcutaneously, and the whole cells of *E. coli* are attenuated or killed --.

Signed and Sealed this
Ninth Day of August, 2016

Michelle K. Lee
*Director of the United States Patent and Trademark Office*